United States Patent
Reynolds et al.

(10) Patent No.: US 7,262,271 B2
(45) Date of Patent: Aug. 28, 2007

(54) **SYNTHETIC PEPTIDE CONSTRUCTS FOR THE DIAGNOSIS AND TREATMENT OF PERIODONTITIS ASSOCIATED WITH *PORPHYROMONAS GINGIVALIS***

(75) Inventors: Eric C. Reynolds, North Balwyn (AU); Neil Martin O'Brien-Simpson, Brunswick (AU); Nada Slakeski, Kew (AU)

(73) Assignees: CSL Limited, Parkville, Victoria (AU); The University of Melbourne, Parkville, Victoria (AU)

( * ) Notice: Subject to any disclaimer, the term of this patent is extended or adjusted under 35 U.S.C. 154(b) by 293 days.

(21) Appl. No.: 10/387,977

(22) Filed: Mar. 12, 2003

(65) Prior Publication Data

US 2004/0005276 A1   Jan. 8, 2004

Related U.S. Application Data

(63) Continuation of application No. 09/423,056, filed as application No. PCT/AU98/00311 on Apr. 30, 1998, now abandoned.

(30) Foreign Application Priority Data

Apr. 30, 1997   (AU) .................................. PO 6528

(51) Int. Cl.
  *A61K 38/00*   (2006.01)
  *G01N 33/554*   (2006.01)
(52) U.S. Cl. ................. 530/326; 530/300; 435/7.32; 424/185.1; 424/234.1

(58) Field of Classification Search ............ None
  See application file for complete search history.

(56) References Cited

U.S. PATENT DOCUMENTS

| | | | | |
|---|---|---|---|---|
| 5,523,390 | A * | 6/1996 | Travis et al. ............... | 536/23.2 |
| 5,536,497 | A | 7/1996 | Evans et al. | |
| 5,824,791 | A * | 10/1998 | Progulske-Fox et al. ... | 536/23.7 |
| 6,017,532 | A * | 1/2000 | Travis et al. ............. | 424/94.65 |
| 6,129,917 | A | 10/2000 | Potempa et al. | |
| 6,511,666 | B1 * | 1/2003 | Reynolds et al. ......... | 424/184.1 |
| 6,833,262 | B1 * | 12/2004 | Travis et al. ................ | 435/220 |
| 2002/0164759 | A1 * | 11/2002 | Travis et al. ................ | 435/219 |
| 2002/0192206 | A1 * | 12/2002 | Kozarov et al. ......... | 424/94.63 |
| 2005/0019318 | A1 * | 1/2005 | Kozarov et al. ......... | 424/94.63 |

FOREIGN PATENT DOCUMENTS

WO          95/07286       *   3/1995

(Continued)

OTHER PUBLICATIONS

Barkocy-Gallagher, Genevieve A et al, J. Bacteriol., vol. 178(10), pp. 2734-2741, May 1996, Analysis of the prtP Gene encoding porphypain, a cysteine proteinase of *Porphyromonas gingivalis*.*

(Continued)

*Primary Examiner*—Mark Navarro
*Assistant Examiner*—Ginny Allen Portner
(74) *Attorney, Agent, or Firm*—Morrison & Foerster LLP

(57) ABSTRACT

The present invention relates to an oral composition and an immunogenic composition for the suppression of the pathogenic effects of the intra-oral bacterium *Porphyromonas gingivalis* associated with periodontal disease.

14 Claims, 11 Drawing Sheets

FOREIGN PATENT DOCUMENTS

| WO | WO-95/07286 A1 | | 3/1995 |
|---|---|---|---|
| WO | 95/09181 | * | 4/1995 |
| WO | WO95/09181 | | 4/1995 |
| WO | WO97/16542 | | 5/1997 |
| WO | WO97/34629 | | 9/1997 |
| WO | WO97/36923 | | 10/1997 |

OTHER PUBLICATIONS

Slakeski, Nada et al, Biochemical and Biophysical Research Communication, vol. 224, pp. 605-610, 1996, Characterization of a *Porphyromonas gingivalis* gene prtR that encodes an arginine-specific Thiol Proteinase and Multiple Adhesins.*

Kirszbaum, L et al, Biochem Biophys.I Res. Com., vol. 207(1), Feb. 6, 1995, p. 424-431, Complete nucleotide sequence of a gene prtR of *Porphyromonas gingivalis* W50 encoding a 132 kDa protein that contains an argiine specific thiol endopeptiase domain.*

Chen, Z et al, Infection Immunity, Aug. 1991, pp. 2846-2850, vol. 59(8), Stimulation of Proteinase and Amidase activities in *Prophyromonas* (Bacteroides) *gingivalis* by amino acids and dipeptides.*

Bhogal et al. (1997). "A cell-associated protein complex of *Porphyromonas gingivalis* W50 composed of Arg- and Lys-specific cysteine proteinases and adhesins," (abstract) *Microbiol.* 143:2485-2495.

Kelly et al. (1997). "The relationship between colonization and haemagglutination inhibiting and B cell epitopes of *Porphyromonas gingivalis*," *Clin. Exp. Immuno.* 110:285-291.

Discipio, R. G. et al. (1996). "Cleavage of Human Complement Component C5 by Cysteine Proteinases from *Porphyromonas* (Bacteroides) *gingivalis*. Prior Oxidation of C5 Augments Proteinases Digestion of C5," *Immunology* 87:660-667.

Genco, C. A et al. (Sep. 1998). "A Peptide Domain on Gingipain R Which Confers Immunity Against *Porphyromomas gingivalis* Infection in Mice," *Infection and Immunity* 66(9):4108-4114.

Supplemental European Search Report for EP patent application No. 98 91 6667 completed on Oct. 8, 2004, 3 pages.

* cited by examiner

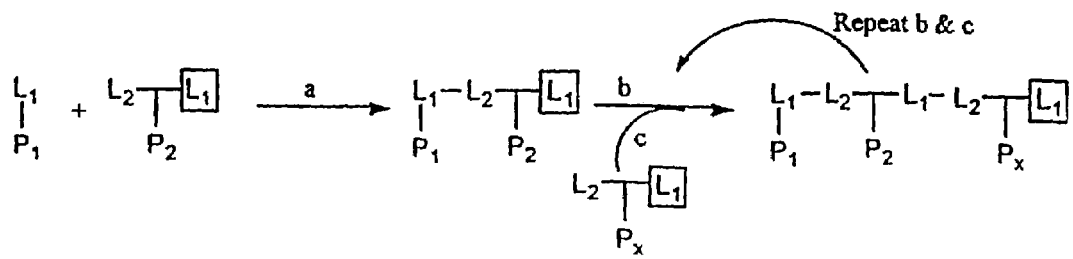
Example
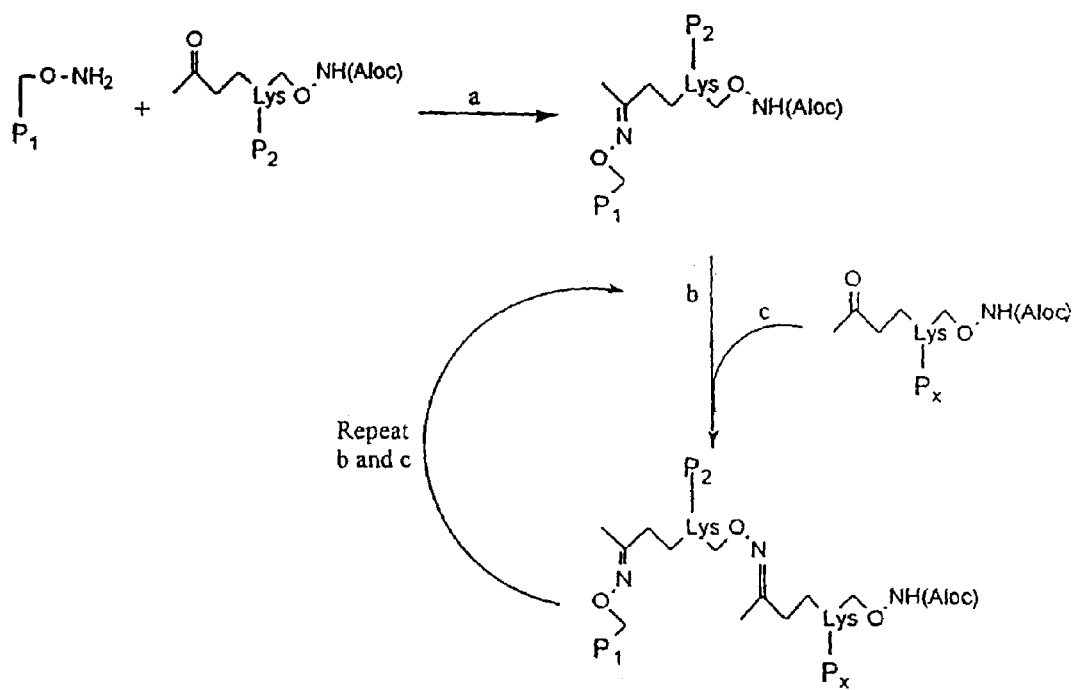
Figure 2

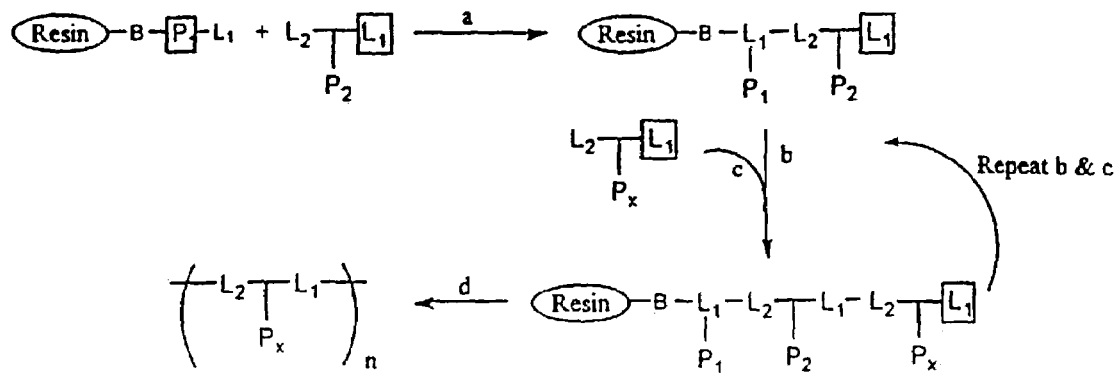
Example
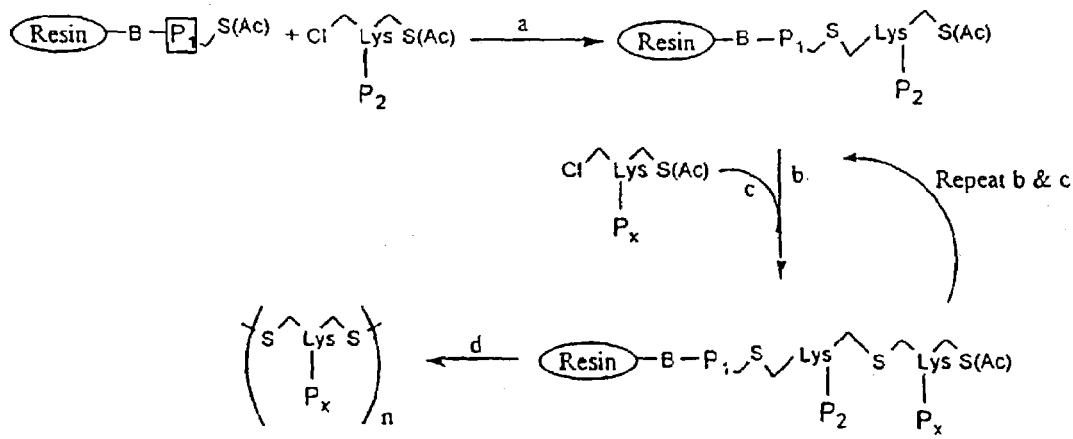
Figure 3

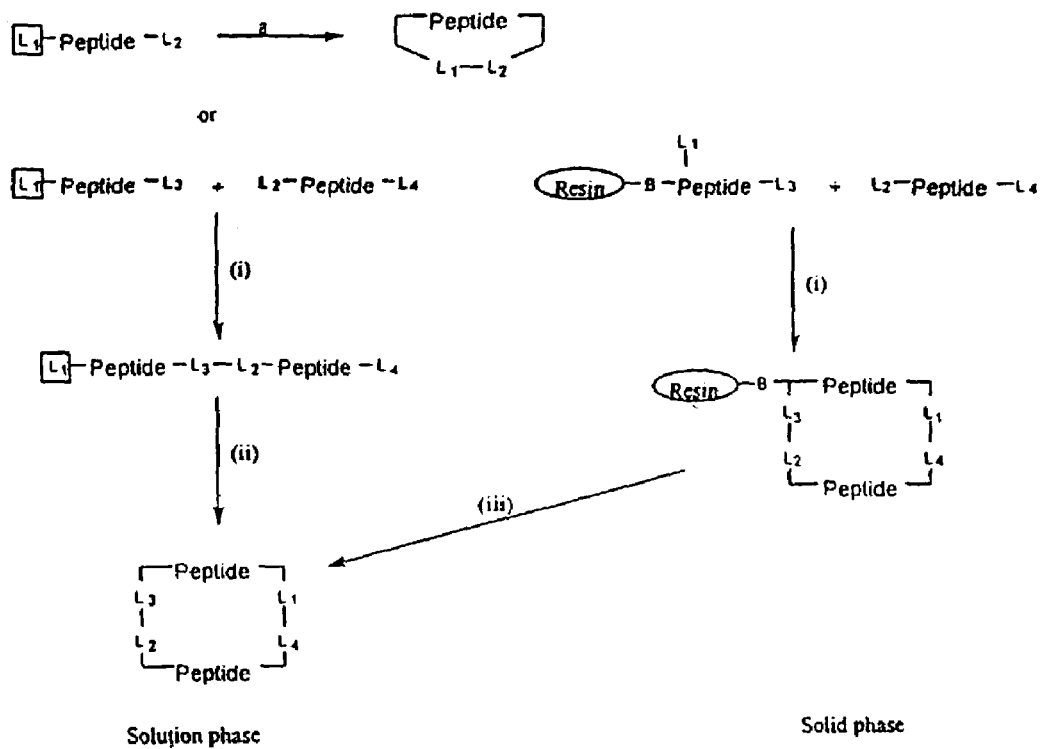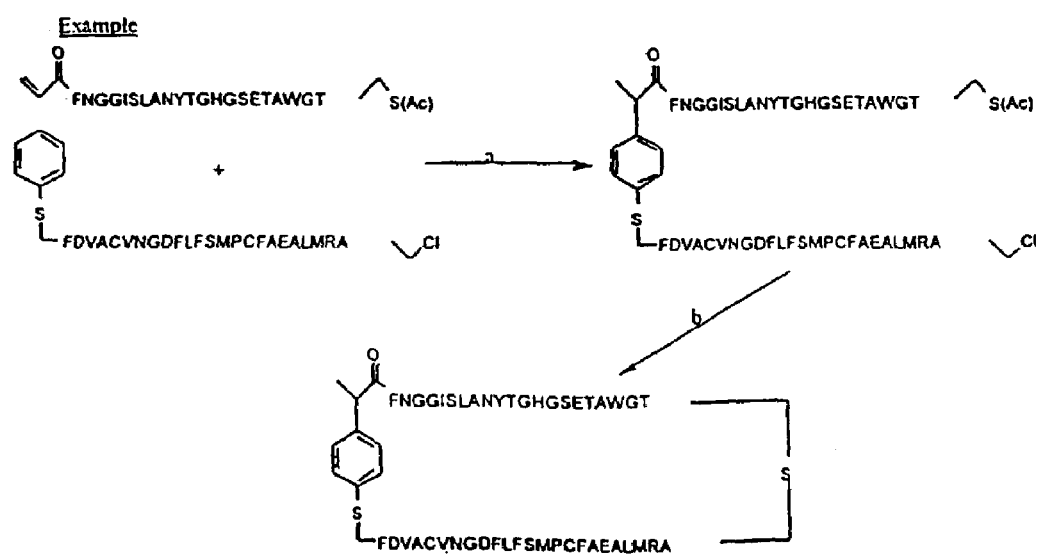
Figure 4

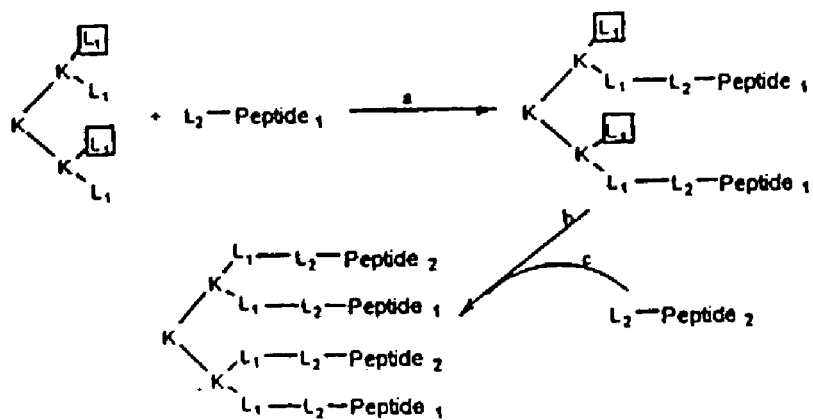
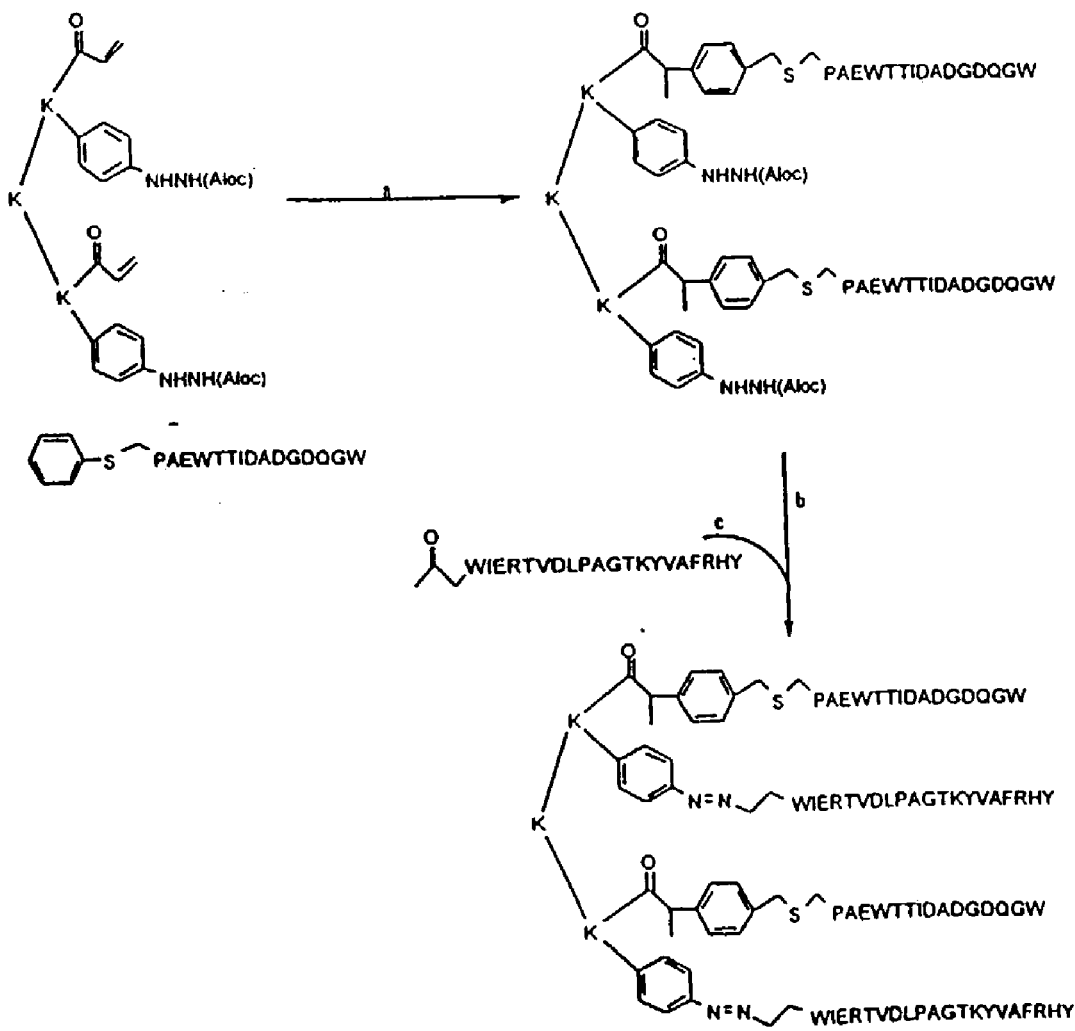
Figure 5

```
              230                                              275
PrtRII50  ..YTPVEEKENG..RMIVIVPKKYEEDIEDFVDWKNQRGLRTEVKVAEDI
PrtR45    ..****Q..****A*GK*****************
PrtK48    DV**DHGDLY*TPV**L*VAGA*FK*ALKPWLT**A*K*FYLD*HYTDEA 276                                              321
PrtRII50  ASPVTANAIQQFVKQEYEKE...GNDLTYVLLVGDHKDIPA.KITPGIKS
PrtR45    ********************...********I********.********
PrtK48    EVGT*NASIKA*IHKK*NDGLAASAAPVFLA****TDV*SGE*GKKTK*V 322                                              371
PrtRII50  DQVYGQIVGNDHYNEVFIGRFSCESKEDLKTQIDRTIHYERNITTEDKWL
PrtR45    **************************************************
PrtK48    TDL*YSA*DG*YFP*MYTF*M*AS*P*E*TNIKVLMKATMPDKSY*

372                                              421
PrtRII50  GQALCIASAEGGPSADNGESDIQHENIIANLLTQYGYTKIIKCYDPGVTP
PrtR45    **********************************V***************
PrtK48    EKV*L**G*DYSWNSQV*QPT*KYG.MQYYYNQEH***DVYNYLKAPY*.

422                                              471
PrtRII50  KNIIDAFNGGISLANYTG[H]SETAWGTSHFGTTHVKQLTNSNQLPFIFDV
PrtR45    *****************[*]******************************
PrtK48    .GCYSHL*T*V*F****A[*]****ADPLLT*SQL*A***KDKYFLAIGN 472                                              521
PrtRII50  A[C]VNGDFLYNVPCFAEALMRAQKDGKPTGTVAIIASTINQSWASPMRGQD
PrtR45    *[*]*****FSM************************************..
PrtK48    Q[*]ITAQ*D*VQ***G*VIT*....V*EK*AY*Y*G*SP*SY*GEDYYWS7

522                                              561
PrtRII50  EMNEILCEKHP..NNIKRTFGGVTMNGMFAMVEKYKKDGEKM........
PrtR45    ***********..****************************........
PrtK48    GA*AVFGVQPTFEGTSMGSYDATFLEDSYNTVNSIMWA*NLAATHAGNIG 562                                              601
PrtRII50  ..........LDTWTVFGDPSLLVRTLVPTKMQVTAPANISASAQTFEVA
PrtR45    ..........***************************Q*NLTDASVN*S
PrtK48    NITHIGAHYYWEAYH*L**G*VMPYRAM*KTNTY*L**SLPQNQASYSIG 602                                              650
PrtRII50  CDYNGAIATLSDDGDMVGTAIVK.DGKAIIKLNESIADETNLTLTVVGYN
PrtR45    *********I*AN*K*F*S*V*E.N*T*T*N*.TGLTN*ST********
PrtK48    ASAGSYV*.I*KVLYGVANAS*V*TVSMTKQ*TENG*YDVVITRS*

651                                              699
PrtRII50  KVTVIKDVKVEGTSIA.DVANDKPYTVAVSGKTITVESPAAGLTIFDMNG
PrtR45    *E*****TINTN*EPNPYQPVSNLTA*TQGQKV*LKWDA*STKTNATTNTA
PrtK48    YLP***QIQ*.*EPSPYQPVSNLTA*TQGQKV*LKW*A*S*KKAEGSREV 700                                              736
PrtRII50  RRVATAKNRMVFEAQNGVYAVRIATEGKTYTEKVIVK
PrtR45    *SVDGIRELVLLSVSDAPELL*...............
PrtK48    K*IGDG....L*VTIEPAND*................
```

Figure 8

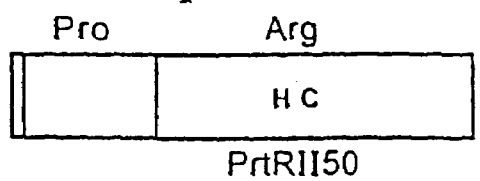
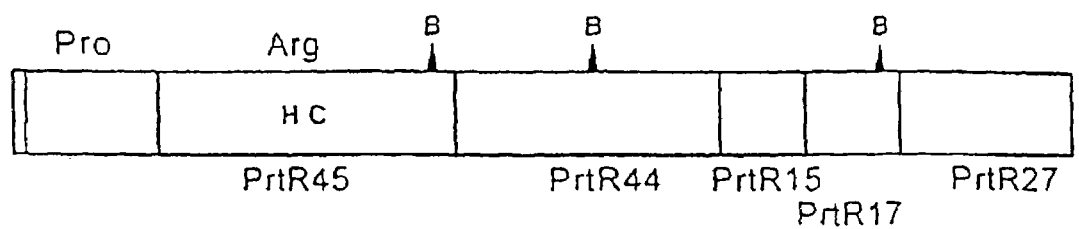
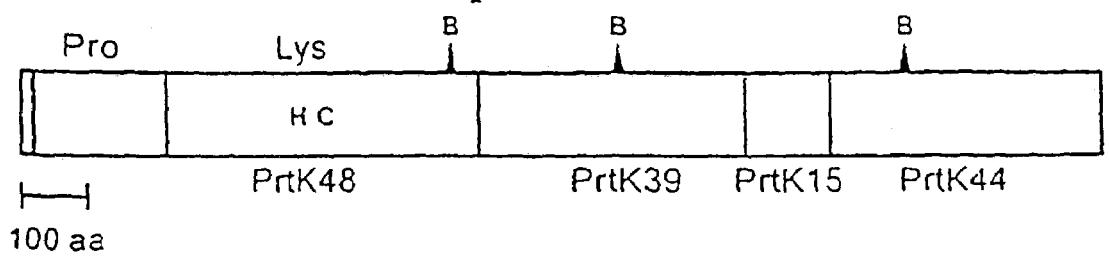
Figure 9

SEQUENCE LISTING

```
<160> NUMBER OF SEQ ID NOS: 105

<210> SEQ ID NO 1
<211> LENGTH: 21
<212> TYPE: PRT
<213> ORGANISM: Porphyromonas gingivalis

<400> SEQUENCE: 1

Phe Asn Gly Gly Ile Ser Leu Ala Asn Tyr Thr Gly His Gly Ser Glu
 1               5                  10                  15

Thr Ala Trp Gly Thr
            20

<210> SEQ ID NO 2
<211> LENGTH: 22
<212> TYPE: PRT
<213> ORGANISM: Porphyromonas gingivalis

<400> SEQUENCE: 2

Leu Asn Thr Gly Val Ser Phe Ala Asn Tyr Thr Ala His Gly Ser Glu
 1               5                  10                  15

Thr Ala Trp Ala Asp Pro
            20

<210> SEQ ID NO 3
<211> LENGTH: 24
<212> TYPE: PRT
<213> ORGANISM: Porphyromonas gingivalis

<400> SEQUENCE: 3

Phe Asp Val Ala Cys Val Asn Gly Asp Phe Leu Phe Ser Met Pro Cys
 1               5                  10                  15

Phe Ala Glu Ala Leu Met Arg Ala
            20

<210> SEQ ID NO 4
<211> LENGTH: 24
<212> TYPE: PRT
<213> ORGANISM: Porphyromonas gingivalis

<400> SEQUENCE: 4

Ile Gly Asn Cys Cys Ile Thr Ala Gln Phe Asp Tyr Val Gln Pro Cys
 1               5                  10                  15

Phe Gly Glu Val Ile Thr Arg Val
            20

<210> SEQ ID NO 5
<211> LENGTH: 31
<212> TYPE: PRT
<213> ORGANISM: Porphyromonas gingivalis

<400> SEQUENCE: 5

Gly Glu Pro Asn Pro Tyr Gln Pro Val Ser Asn Leu Thr Ala Thr Thr
 1               5                  10                  15

Gln Gly Gln Lys Val Thr Leu Lys Trp Asp Ala Pro Ser Thr Lys
            20                  25                  30
```

<210> SEQ ID NO 6
<211> LENGTH: 31
<212> TYPE: PRT
<213> ORGANISM: Porphyromonas gingivalis

<400> SEQUENCE: 6

Glu Gly Ser Asn Glu Phe Ala Pro Val Gln Asn Leu Thr Gly Ser Ala
1               5                   10                  15

Val Gly Gln Lys Val Thr Leu Lys Trp Asp Ala Pro Asn Gly Thr
            20                  25                  30

<210> SEQ ID NO 7
<211> LENGTH: 31
<212> TYPE: PRT
<213> ORGANISM: Porphyromonas gingivalis

<400> SEQUENCE: 7

Val Asn Ser Thr Gln Phe Asn Pro Val Lys Asn Leu Lys Ala Gln Pro
1               5                   10                  15

Asp Gly Gly Asp Val Val Leu Lys Trp Glu Ala Pro Ser Ala Lys
            20                  25                  30

<210> SEQ ID NO 8
<211> LENGTH: 31
<212> TYPE: PRT
<213> ORGANISM: Porphyromonas gingivalis

<400> SEQUENCE: 8

Gly Glu Pro Ser Pro Tyr Gln Pro Val Ser Asn Leu Thr Ala Thr Thr
1               5                   10                  15

Gln Gly Gln Lys Val Thr Leu Lys Trp Glu Ala Pro Ser Ala Lys
            20                  25                  30

<210> SEQ ID NO 9
<211> LENGTH: 31
<212> TYPE: PRT
<213> ORGANISM: Porphyromonas gingivalis

<400> SEQUENCE: 9

Glu Gly Ser Asn Glu Phe Ala Pro Val Gln Asn Leu Thr Gly Ser Ser
1               5                   10                  15

Val Gly Gln Lys Val Thr Leu Lys Trp Asp Ala Pro Asn Gly Thr
            20                  25                  30

<210> SEQ ID NO 10
<211> LENGTH: 33
<212> TYPE: PRT
<213> ORGANISM: Porphyromonas gingivalis

<400> SEQUENCE: 10

Val Asn Ser Thr Gln Phe Asn Pro Val Gln Asn Leu Thr Ala Glu Gln
1               5                   10                  15

Ala Pro Asn Ser Met Asp Ala Ile Leu Lys Trp Asn Ala Pro Ala Ser
            20                  25                  30

Lys

<210> SEQ ID NO 11
<211> LENGTH: 27
<212> TYPE: PRT
<213> ORGANISM: Porphyromonas gingivalis

<400> SEQUENCE: 11

```
Gln Phe Asn Pro Val Gln Asn Leu Thr Gly Ser Ala Val Gly Gln Lys
 1               5                  10                  15

Val Thr Leu Lys Trp Asp Ala Pro Asn Gly Thr
            20                  25

<210> SEQ ID NO 12
<211> LENGTH: 27
<212> TYPE: PRT
<213> ORGANISM: Porphyromonas gingivalis

<400> SEQUENCE: 12

Gln Phe Asn Pro Val Gln Asn Leu Thr Gly Ser Ala Val Gly Gln Lys
 1               5                  10                  15

Val Thr Leu Lys Trp Asp Ala Pro Asn Gly Thr
            20                  25

<210> SEQ ID NO 13
<211> LENGTH: 27
<212> TYPE: PRT
<213> ORGANISM: Porphyromonas gingivalis

<400> SEQUENCE: 13

Gln Phe Asn Pro Val Gln Asn Leu Thr Gly Ser Ala Val Gly Gln Lys
 1               5                  10                  15

Val Thr Leu Lys Trp Asp Ala Pro Asn Gly Thr
            20                  25

<210> SEQ ID NO 14
<211> LENGTH: 26
<212> TYPE: PRT
<213> ORGANISM: Porphyromonas gingivalis

<400> SEQUENCE: 14

Phe Ala His Val Gln Asn Leu Thr Gly Ser Ala Val Gly Gln Lys Val
 1               5                  10                  15

Thr Leu Lys Trp Asp Ala Pro Asn Gly Thr
            20                  25

<210> SEQ ID NO 15
<211> LENGTH: 26
<212> TYPE: PRT
<213> ORGANISM: Porphyromonas gingivalis

<400> SEQUENCE: 15

Phe Ala Pro Val Gln Asn Leu Gln Trp Ser Val Ser Gly Gln Thr Val
 1               5                  10                  15

Thr Leu Thr Trp Gln Ala Pro Ala Ser Asp
            20                  25

<210> SEQ ID NO 16
<211> LENGTH: 29
<212> TYPE: PRT
<213> ORGANISM: Porphyromonas gingivalis

<400> SEQUENCE: 16

Gln Phe Asn Pro Val Gln Asn Leu Thr Ala Glu Gln Ala Pro Asn Ser
 1               5                  10                  15

Met Asp Ala Ile Leu Lys Trp Asn Ala Pro Ala Ser Lys
            20                  25

<210> SEQ ID NO 17
<211> LENGTH: 29
```

```
<212> TYPE: PRT
<213> ORGANISM: Porphyromonas gingivalis

<400> SEQUENCE: 17

Asp Tyr Thr Tyr Thr Val Tyr Arg Asp Gly Thr Lys Ile Lys Glu Gly
 1               5                  10                  15

Leu Thr Ala Thr Thr Phe Glu Glu Asp Gly Val Ala Thr
             20                  25

<210> SEQ ID NO 18
<211> LENGTH: 29
<212> TYPE: PRT
<213> ORGANISM: Porphyromonas gingivalis

<400> SEQUENCE: 18

Asp Tyr Thr Tyr Thr Val Tyr Arg Asp Gly Thr Lys Ile Lys Glu Gly
 1               5                  10                  15

Leu Thr Glu Thr Thr Phe Glu Glu Asp Gly Val Ala Thr
             20                  25

<210> SEQ ID NO 19
<211> LENGTH: 29
<212> TYPE: PRT
<213> ORGANISM: Porphyromonas gingivalis

<400> SEQUENCE: 19

Ser Tyr Thr Tyr Thr Val Tyr Arg Asp Gly Thr Lys Ile Lys Glu Gly
 1               5                  10                  15

Leu Thr Glu Thr Thr Tyr Arg Asp Ala Gly Met Ser Ala
             20                  25

<210> SEQ ID NO 20
<211> LENGTH: 29
<212> TYPE: PRT
<213> ORGANISM: Porphyromonas gingivalis

<400> SEQUENCE: 20

Ser Tyr Thr Tyr Thr Val Tyr Arg Asp Gly Thr Lys Ile Lys Glu Gly
 1               5                  10                  15

Leu Thr Ala Thr Thr Phe Glu Glu Asp Gly Val Ala Ala
             20                  25

<210> SEQ ID NO 21
<211> LENGTH: 29
<212> TYPE: PRT
<213> ORGANISM: Porphyromonas gingivalis

<400> SEQUENCE: 21

Asp Tyr Thr Tyr Thr Val Tyr Arg Asp Gly Thr Lys Ile Lys Glu Gly
 1               5                  10                  15

Leu Thr Glu Thr Thr Phe Glu Glu Asp Gly Val Ala Thr
             20                  25

<210> SEQ ID NO 22
<211> LENGTH: 29
<212> TYPE: PRT
<213> ORGANISM: Porphyromonas gingivalis

<400> SEQUENCE: 22

Ser Tyr Thr Tyr Thr Ile Tyr Arg Asn Asn Thr Gln Ile Ala Ser Gly
 1               5                  10                  15

Val Thr Glu Thr Thr Tyr Arg Asp Pro Asp Leu Ala Thr
```

```
                     20                  25

<210> SEQ ID NO 23
<211> LENGTH: 29
<212> TYPE: PRT
<213> ORGANISM: Porphyromonas gingivalis

<400> SEQUENCE: 23

Asp Tyr Thr Tyr Thr Val Tyr Arg Asp Gly Thr Lys Ile Lys Glu Gly
 1               5                  10                  15

Leu Thr Glu Thr Thr Phe Glu Glu Asp Gly Val Ala Thr
             20                  25

<210> SEQ ID NO 24
<211> LENGTH: 29
<212> TYPE: PRT
<213> ORGANISM: Porphyromonas gingivalis

<400> SEQUENCE: 24

Asp Tyr Thr Tyr Thr Val Tyr Arg Asp Gly Thr Lys Ile Lys Glu Gly
 1               5                  10                  15

Leu Thr Glu Thr Thr Phe Glu Glu Asp Gly Val Ala Thr
             20                  25

<210> SEQ ID NO 25
<211> LENGTH: 29
<212> TYPE: PRT
<213> ORGANISM: Porphyromonas gingivalis

<400> SEQUENCE: 25

Asp Tyr Thr Tyr Thr Val Tyr Arg Asp Gly Thr Lys Ile Lys Trp Gly
 1               5                  10                  15

Leu Thr Glu Thr Thr Phe Glu Glu Asp Gly Val Ala Thr
             20                  25

<210> SEQ ID NO 26
<211> LENGTH: 29
<212> TYPE: PRT
<213> ORGANISM: Porphyromonas gingivalis

<400> SEQUENCE: 26

Asp Tyr Thr Tyr Thr Val Tyr Arg Asp Gly Thr Lys Ile Lys Glu Gly
 1               5                  10                  15

Leu Thr Glu Thr Thr Phe Glu Glu Asp Gly Val Ala Thr
             20                  25

<210> SEQ ID NO 27
<211> LENGTH: 29
<212> TYPE: PRT
<213> ORGANISM: Porphyromonas gingivalis

<400> SEQUENCE: 27

Asp Tyr Thr Tyr Thr Val Tyr Arg Asp Asn Val Val Ile Ala Gln Asn
 1               5                  10                  15

Leu Ala Ala Thr Thr Phe Asn Gln Glu Asn Val Ala Pro
             20                  25

<210> SEQ ID NO 28
<211> LENGTH: 29
<212> TYPE: PRT
<213> ORGANISM: Porphyromonas gingivalis

<400> SEQUENCE: 28
```

```
Ser Tyr Thr Tyr Thr Ile Tyr Arg Asn Asn Thr Gln Ile Ala Ser Gly
1               5                   10                  15

Val Thr Glu Thr Thr Tyr Arg Asp Pro Asp Leu Ala Thr
            20                  25

<210> SEQ ID NO 29
<211> LENGTH: 26
<212> TYPE: PRT
<213> ORGANISM: Porphyromonas gingivalis

<400> SEQUENCE: 29

Pro Asn Gly Thr Pro Asn Pro Asn Pro Asn Pro Asn Pro Asn Pro Asn
1               5                   10                  15

Pro Gly Thr Thr Thr Leu Ser Glu Ser Phe
            20                  25

<210> SEQ ID NO 30
<211> LENGTH: 23
<212> TYPE: PRT
<213> ORGANISM: Porphyromonas gingivalis

<400> SEQUENCE: 30

Pro Asn Gly Thr Pro Asn Pro Asn Pro Asn Pro Asn Pro Asn Pro Gly
1               5                   10                  15

Thr Thr Leu Ser Glu Ser Phe
            20

<210> SEQ ID NO 31
<211> LENGTH: 22
<212> TYPE: PRT
<213> ORGANISM: Porphyromonas gingivalis

<400> SEQUENCE: 31

Pro Asn Gly Thr Pro Asn Pro Asn Pro Asn Pro Asn Pro Gly Thr Thr
1               5                   10                  15

Thr Leu Ser Glu Ser Phe
            20

<210> SEQ ID NO 32
<211> LENGTH: 22
<212> TYPE: PRT
<213> ORGANISM: Porphyromonas gingivalis

<400> SEQUENCE: 32

Pro Asn Gly Thr Pro Asn Pro Asn Pro Asn Pro Asn Pro Gly Thr Thr
1               5                   10                  15

Thr Leu Ser Glu Ser Phe
            20

<210> SEQ ID NO 33
<211> LENGTH: 22
<212> TYPE: PRT
<213> ORGANISM: Porphyromonas gingivalis

<400> SEQUENCE: 33

Pro Asn Gly Thr Pro Asn Pro Asn Pro Asn Pro Asn Pro Gly Thr Thr
1               5                   10                  15

Thr Leu Ser Glu Ser Phe
            20

<210> SEQ ID NO 34
```

```
<211> LENGTH: 18
<212> TYPE: PRT
<213> ORGANISM: Porphyromonas gingivalis

<400> SEQUENCE: 34

Pro Asn Gly Thr Pro Asn Pro Asn Pro Gly Thr Thr Leu Ser Glu
 1               5                  10                  15

Ser Phe

<210> SEQ ID NO 35
<211> LENGTH: 20
<212> TYPE: PRT
<213> ORGANISM: Porphyromonas gingivalis

<400> SEQUENCE: 35

Trp Ile Glu Arg Thr Val Asp Leu Pro Ala Gly Thr Lys Tyr Val Ala
 1               5                  10                  15

Phe Arg His Tyr
            20

<210> SEQ ID NO 36
<211> LENGTH: 20
<212> TYPE: PRT
<213> ORGANISM: Porphyromonas gingivalis

<400> SEQUENCE: 36

Trp Arg Gln Lys Thr Val Asp Leu Pro Ala Gly Thr Lys Tyr Val Ala
 1               5                  10                  15

Phe Arg His Phe
            20

<210> SEQ ID NO 37
<211> LENGTH: 20
<212> TYPE: PRT
<213> ORGANISM: Porphyromonas gingivalis

<400> SEQUENCE: 37

Trp Ile Glu Arg Thr Val Asp Leu Pro Ala Gly Thr Lys Tyr Val Ala
 1               5                  10                  15

Phe Arg His Tyr
            20

<210> SEQ ID NO 38
<211> LENGTH: 20
<212> TYPE: PRT
<213> ORGANISM: Porphyromonas gingivalis

<400> SEQUENCE: 38

Trp Arg Gln Lys Thr Val Asp Leu Pro Ala Gly Thr Lys Tyr Val Ala
 1               5                  10                  15

Phe Arg His Phe
            20

<210> SEQ ID NO 39
<211> LENGTH: 20
<212> TYPE: PRT
<213> ORGANISM: Porphyromonas gingivalis

<400> SEQUENCE: 39

Trp Tyr Gln Lys Thr Val Gln Leu Pro Ala Gly Thr Lys Tyr Val Ala
 1               5                  10                  15

Phe Arg His Phe
```

20

<210> SEQ ID NO 40
<211> LENGTH: 20
<212> TYPE: PRT
<213> ORGANISM: Porphyromonas gingivalis

<400> SEQUENCE: 40

Trp Ile Glu Arg Thr Val Asp Leu Pro Ala Gly Thr Lys Tyr Val Ala
1               5                   10                  15

Phe Arg His Tyr
            20

<210> SEQ ID NO 41
<211> LENGTH: 20
<212> TYPE: PRT
<213> ORGANISM: Porphyromonas gingivalis

<400> SEQUENCE: 41

Trp Ile Glu Arg Thr Val Asp Leu Pro Ala Gly Thr Lys Tyr Val Ala
1               5                   10                  15

Phe Arg His Tyr
            20

<210> SEQ ID NO 42
<211> LENGTH: 20
<212> TYPE: PRT
<213> ORGANISM: Porphyromonas gingivalis

<400> SEQUENCE: 42

Trp Ile Glu Arg Thr Val Asp Leu Pro Ala Gly Thr Lys Tyr Val Ala
1               5                   10                  15

Phe Arg His Tyr
            20

<210> SEQ ID NO 43
<211> LENGTH: 20
<212> TYPE: PRT
<213> ORGANISM: Porphyromonas gingivalis

<400> SEQUENCE: 43

Trp Ile Glu Arg Thr Val Asp Leu Pro Ala Gly Thr Lys Tyr Val Ala
1               5                   10                  15

Phe Arg His Tyr
            20

<210> SEQ ID NO 44
<211> LENGTH: 20
<212> TYPE: PRT
<213> ORGANISM: Porphyromonas gingivalis

<400> SEQUENCE: 44

Trp Tyr Gln Lys Thr Val Gln Leu Pro Ala Gly Thr Lys Tyr Val Ala
1               5                   10                  15

Phe Arg His Phe
            20

<210> SEQ ID NO 45
<211> LENGTH: 20
<212> TYPE: PRT
<213> ORGANISM: Porphyromonas gingivalis

<400> SEQUENCE: 45

```
Trp Tyr Gln Lys Thr Val Gln Leu Pro Ala Gly Thr Lys Tyr Val Ala
1               5                   10                  15

Phe Arg His Phe
            20

<210> SEQ ID NO 46
<211> LENGTH: 20
<212> TYPE: PRT
<213> ORGANISM: Porphyromonas gingivalis

<400> SEQUENCE: 46

Trp Tyr Gln Lys Thr Val Gln Leu Pro Ala Gly Thr Lys Tyr Val Ala
1               5                   10                  15

Phe Arg His Phe
            20

<210> SEQ ID NO 47
<211> LENGTH: 20
<212> TYPE: PRT
<213> ORGANISM: Porphyromonas gingivalis

<400> SEQUENCE: 47

Trp Tyr Gln Lys Thr Val Gln Leu Pro Ala Gly Thr Lys Tyr Val Ala
1               5                   10                  15

Phe Arg His Phe
            20

<210> SEQ ID NO 48
<211> LENGTH: 20
<212> TYPE: PRT
<213> ORGANISM: Porphyromonas gingivalis

<400> SEQUENCE: 48

Trp Tyr Gln Lys Thr Val Gln Leu Pro Ala Gly Thr Lys Tyr Val Ala
1               5                   10                  15

Phe Arg His Phe
            20

<210> SEQ ID NO 49
<211> LENGTH: 21
<212> TYPE: PRT
<213> ORGANISM: Porphyromonas gingivalis

<400> SEQUENCE: 49

Glu Arg Thr Ile Asp Leu Ser Ala Tyr Ala Gly Gln Gln Val Tyr Leu
1               5                   10                  15

Ala Phe Arg His Phe
            20

<210> SEQ ID NO 50
<211> LENGTH: 16
<212> TYPE: PRT
<213> ORGANISM: Porphyromonas gingivalis

<400> SEQUENCE: 50

Pro Ala Glu Trp Thr Thr Ile Asp Ala Asp Gly Asp Gly Gln Gly Trp
1               5                   10                  15

<210> SEQ ID NO 51
<211> LENGTH: 16
<212> TYPE: PRT
<213> ORGANISM: Porphyromonas gingivalis
```

-continued

```
<400> SEQUENCE: 51

Pro Ala Ser Trp Lys Thr Ile Asp Ala Asp Gly Asp Gly His Gly Trp
1               5                   10                  15

<210> SEQ ID NO 52
<211> LENGTH: 16
<212> TYPE: PRT
<213> ORGANISM: Porphyromonas gingivalis

<400> SEQUENCE: 52

Pro Ala Glu Trp Thr Thr Ile Asp Ala Asp Gly Asp Gly Gln Gly Trp
1               5                   10                  15

<210> SEQ ID NO 53
<211> LENGTH: 16
<212> TYPE: PRT
<213> ORGANISM: Porphyromonas gingivalis

<400> SEQUENCE: 53

Pro Ala Ser Trp Lys Thr Ile Asp Ala Asp Gly Asp Gly His Gly Trp
1               5                   10                  15

<210> SEQ ID NO 54
<211> LENGTH: 16
<212> TYPE: PRT
<213> ORGANISM: Porphyromonas gingivalis

<400> SEQUENCE: 54

Pro Ala Ser Trp Lys Thr Ile Asp Ala Asp Gly Asp Gly Asn Asn Trp
1               5                   10                  15

<210> SEQ ID NO 55
<211> LENGTH: 16
<212> TYPE: PRT
<213> ORGANISM: Porphyromonas gingivalis

<400> SEQUENCE: 55

Pro Ala Glu Trp Thr Thr Ile Asp Ala Asp Gly Asp Gly Gln Gly Trp
1               5                   10                  15

<210> SEQ ID NO 56
<211> LENGTH: 16
<212> TYPE: PRT
<213> ORGANISM: Porphyromonas gingivalis

<400> SEQUENCE: 56

Pro Ala Glu Trp Thr Thr Ile Asp Ala Asp Gly Asp Gly Gln Gly Trp
1               5                   10                  15

<210> SEQ ID NO 57
<211> LENGTH: 16
<212> TYPE: PRT
<213> ORGANISM: Porphyromonas gingivalis

<400> SEQUENCE: 57

Pro Ala Glu Trp Thr Thr Ile Asp Ala Asp Gly Asp Gly Gln Gly Trp
1               5                   10                  15

<210> SEQ ID NO 58
<211> LENGTH: 16
<212> TYPE: PRT
<213> ORGANISM: Porphyromonas gingivalis

<400> SEQUENCE: 58
```

Pro Ala Glu Trp Thr Thr Ile Asp Ala Asp Gly Asp Gly Gln Gly Trp
1               5                   10                  15

<210> SEQ ID NO 59
<211> LENGTH: 16
<212> TYPE: PRT
<213> ORGANISM: Porphyromonas gingivalis

<400> SEQUENCE: 59

Pro Ala Ser Trp Lys Thr Ile Asp Ala Asp Gly Asp Gly Asn Asn Trp
1               5                   10                  15

<210> SEQ ID NO 60
<211> LENGTH: 16
<212> TYPE: PRT
<213> ORGANISM: Porphyromonas gingivalis

<400> SEQUENCE: 60

Pro Ala Ser Trp Lys Thr Ile Asp Ala Asp Gly Asp Gly Asn Asn Trp
1               5                   10                  15

<210> SEQ ID NO 61
<211> LENGTH: 16
<212> TYPE: PRT
<213> ORGANISM: Porphyromonas gingivalis

<400> SEQUENCE: 61

Pro Ala Ser Trp Lys Thr Ile Asp Ala Asp Gly Asp Gly Asn Asn Trp
1               5                   10                  15

<210> SEQ ID NO 62
<211> LENGTH: 16
<212> TYPE: PRT
<213> ORGANISM: Porphyromonas gingivalis

<400> SEQUENCE: 62

Pro Ala Ser Trp Lys Thr Ile Asp Ala Asp Gly Asp Gly Asn Asn Trp
1               5                   10                  15

<210> SEQ ID NO 63
<211> LENGTH: 16
<212> TYPE: PRT
<213> ORGANISM: Porphyromonas gingivalis

<400> SEQUENCE: 63

Pro Ser Ser Trp Lys Thr Ile Asp Ala Asp Gly Asp Gly Asn Asn Trp
1               5                   10                  15

<210> SEQ ID NO 64
<211> LENGTH: 16
<212> TYPE: PRT
<213> ORGANISM: Porphyromonas gingivalis

<400> SEQUENCE: 64

Pro Asn Gly Trp Thr Met Ile Asp Ala Asp Gly Asp Gly His Asn Trp
1               5                   10                  15

<210> SEQ ID NO 65
<211> LENGTH: 20
<212> TYPE: PRT
<213> ORGANISM: Porphyromonas gingivalis

<400> SEQUENCE: 65

Glu Gly Ser Asn Glu Phe Ala Pro Val Gln Asn Leu Thr Gly Ser Ala

Val Gly Gln Lys
        20

<210> SEQ ID NO 66
<211> LENGTH: 20
<212> TYPE: PRT
<213> ORGANISM: Porphyromonas gingivalis

<400> SEQUENCE: 66

Gly Glu Pro Asn Pro Tyr Gln Pro Val Ser Asn Leu Thr Ala Thr Thr
1               5                   10                  15

Gln Gly Gln Lys
        20

<210> SEQ ID NO 67
<211> LENGTH: 20
<212> TYPE: PRT
<213> ORGANISM: Porphyromonas gingivalis

<400> SEQUENCE: 67

Glu Gly Ser Asn Glu Phe Ala Pro Val Gln Asn Leu Thr Gly Ser Ser
1               5                   10                  15

Val Gly Gln Lys
        20

<210> SEQ ID NO 68
<211> LENGTH: 20
<212> TYPE: PRT
<213> ORGANISM: Porphyromonas gingivalis

<400> SEQUENCE: 68

Gly Glu Pro Ser Pro Tyr Gln Pro Val Ser Asn Leu Thr Ala Thr Thr
1               5                   10                  15

Gln Gly Gln Lys
        20

<210> SEQ ID NO 69
<211> LENGTH: 19
<212> TYPE: PRT
<213> ORGANISM: Porphyromonas gingivalis

<400> SEQUENCE: 69

Asn Ser Thr Gln Phe Asn Pro Val Gln Asn Leu Thr Ala Glu Gln Ala
1               5                   10                  15

Pro Asn Ser

<210> SEQ ID NO 70
<211> LENGTH: 20
<212> TYPE: PRT
<213> ORGANISM: Porphyromonas gingivalis

<400> SEQUENCE: 70

Glu Gly Ser Asn Glu Phe Ala His Val Gln Asn Leu Thr Gly Ser Ala
1               5                   10                  15

Val Gly Gln Lys
        20

<210> SEQ ID NO 71
<211> LENGTH: 19
<212> TYPE: PRT
<213> ORGANISM: Porphyromonas gingivalis -continued

<400> SEQUENCE: 71

Asp Pro Val Gln Phe Asn Pro Val Gln Asn Leu Thr Gly Ser Ala Val
1               5                   10                  15

Gly Gln Lys

<210> SEQ ID NO 72
<211> LENGTH: 19
<212> TYPE: PRT
<213> ORGANISM: Porphyromonas gingivalis

<400> SEQUENCE: 72

Asp Pro Val Gln Phe Asn Pro Val Gln Asn Leu Thr Gly Ser Ala Val
1               5                   10                  15

Gly Gln Lys

<210> SEQ ID NO 73
<211> LENGTH: 19
<212> TYPE: PRT
<213> ORGANISM: Porphyromonas gingivalis

<400> SEQUENCE: 73

Asp Pro Val Gln Phe Asn Pro Val Gln Asn Leu Thr Gly Ser Ala Val
1               5                   10                  15

Gly Gln Lys

<210> SEQ ID NO 74
<211> LENGTH: 20
<212> TYPE: PRT
<213> ORGANISM: Porphyromonas gingivalis

<400> SEQUENCE: 74

Glu Gly Gly Asn Glu Phe Ala Pro Val Gln Asn Leu Gln Trp Ser Val
1               5                   10                  15

Ser Gly Gln Thr
            20

<210> SEQ ID NO 75
<211> LENGTH: 19
<212> TYPE: PRT
<213> ORGANISM: Porphyromonas gingivalis

<400> SEQUENCE: 75

Asn Pro Thr Gln Phe Asn Pro Val Gln Asn Leu Thr Ala Glu Gln Ala
1               5                   10                  15

Pro Asn Ser

<210> SEQ ID NO 76
<211> LENGTH: 25
<212> TYPE: PRT
<213> ORGANISM: Porphyromonas gingivalis

<400> SEQUENCE: 76

Gly Asn His Glu Tyr Cys Val Glu Val Lys Tyr Thr Ala Gly Val Ser
1               5                   10                  15

Pro Lys Val Cys Lys Asp Val Thr Val
            20                  25

<210> SEQ ID NO 77
<211> LENGTH: 25
<212> TYPE: PRT

<213> ORGANISM: Porphyromonas gingivalis

<400> SEQUENCE: 77

Gly Asn His Glu Tyr Cys Val Glu Val Lys Tyr Thr Ala Gly Val Ser
1               5                   10                  15
Pro Lys Lys Cys Val Asn Val Thr Val
            20                  25

<210> SEQ ID NO 78
<211> LENGTH: 21
<212> TYPE: PRT
<213> ORGANISM: Porphyromonas gingivalis

<400> SEQUENCE: 78

Ser His Glu Tyr Cys Val Glu Val Lys Tyr Thr Ala Gly Val Ser Pro
1               5                   10                  15
Lys Val Cys Val Asp
            20

<210> SEQ ID NO 79
<211> LENGTH: 25
<212> TYPE: PRT
<213> ORGANISM: Porphyromonas gingivalis

<400> SEQUENCE: 79

Gly Asn His Glu Tyr Cys Val Glu Val Lys Tyr Thr Ala Gly Val Ser
1               5                   10                  15
Pro Lys Val Cys Lys Asp Val Thr Val
            20                  25

<210> SEQ ID NO 80
<211> LENGTH: 25
<212> TYPE: PRT
<213> ORGANISM: Porphyromonas gingivalis

<400> SEQUENCE: 80

Gly Asn His Glu Tyr Cys Val Glu Val Lys Tyr Thr Ala Gly Val Ser
1               5                   10                  15
Pro Lys Lys Cys Val Asn Val Thr Val
            20                  25

<210> SEQ ID NO 81
<211> LENGTH: 25
<212> TYPE: PRT
<213> ORGANISM: Porphyromonas gingivalis

<400> SEQUENCE: 81

Gly Asn His Glu Tyr Cys Val Glu Val Lys Tyr Thr Ala Gly Val Ser
1               5                   10                  15
Pro Lys Val Cys Val Asn Val Thr Ile
            20                  25

<210> SEQ ID NO 82
<211> LENGTH: 25
<212> TYPE: PRT
<213> ORGANISM: Porphyromonas gingivalis

<400> SEQUENCE: 82

Gly Gln Tyr Asn Tyr Cys Val Glu Val Lys Tyr Thr Ala Gly Val Ser
1               5                   10                  15
Pro Lys Val Cys Lys Asp Val Thr Val
            20                  25

<210> SEQ ID NO 83
<211> LENGTH: 25
<212> TYPE: PRT
<213> ORGANISM: Porphyromonas gingivalis

<400> SEQUENCE: 83

Gly Asn His Glu Tyr Cys Val Glu Val Lys Tyr Thr Ala Gly Val Ser
1               5                   10                  15

Pro Glu Val Cys Val Asn Val Thr Val
            20                  25

<210> SEQ ID NO 84
<211> LENGTH: 25
<212> TYPE: PRT
<213> ORGANISM: Porphyromonas gingivalis

<400> SEQUENCE: 84

Gly Asn His Glu Tyr Cys Val Glu Val Lys Tyr Thr Ala Gly Val Ser
1               5                   10                  15

Pro Glu Val Cys Val Asn Val Thr Val
            20                  25

<210> SEQ ID NO 85
<211> LENGTH: 25
<212> TYPE: PRT
<213> ORGANISM: Porphyromonas gingivalis

<400> SEQUENCE: 85

Gly Asn His Glu Tyr Cys Val Glu Val Lys Tyr Thr Ala Gly Val Ser
1               5                   10                  15

Pro Glu Val Cys Val Asn Val Thr Val
            20                  25

<210> SEQ ID NO 86
<211> LENGTH: 27
<212> TYPE: PRT
<213> ORGANISM: Porphyromonas gingivalis

<400> SEQUENCE: 86

Pro Tyr Gln Pro Val Ser Asn Leu Thr Ala Thr Thr Gln Gly Gln Lys
1               5                   10                  15

Val Thr Leu Lys Trp Asp Ala Pro Ser Thr Lys
            20                  25

<210> SEQ ID NO 87
<211> LENGTH: 16
<212> TYPE: DNA
<213> ORGANISM: Porphyromonas gingivalis

<400> SEQUENCE: 87
cggcttccgt aaagtc                                              16

<210> SEQ ID NO 88
<211> LENGTH: 24
<212> TYPE: DNA
<213> ORGANISM: Porphyromonas gingivalis

<400> SEQUENCE: 88
tggctacgat gacgatcata cgac                                     24

<210> SEQ ID NO 89

```
<211> LENGTH: 26
<212> TYPE: PRT
<213> ORGANISM: Porphyromonas gingivalis

<400> SEQUENCE: 89

Tyr Thr Pro Val Glu Glu Lys Glu Asn Gly Arg Met Ile Val Ile Val
 1               5                  10                  15

Pro Lys Lys Tyr Glu Glu Asp Ile Glu Asp
            20                  25

<210> SEQ ID NO 90
<211> LENGTH: 6
<212> TYPE: PRT
<213> ORGANISM: Porphyromonas gingivalis
<220> FEATURE:
<221> NAME/KEY: VARIANT
<222> LOCATION: 3
<223> OTHER INFORMATION: Xaa = Any Amino Acid

<400> SEQUENCE: 90

Pro Val Xaa Asn Leu Thr
 1               5

<210> SEQ ID NO 91
<211> LENGTH: 6
<212> TYPE: PRT
<213> ORGANISM: Porphyromonas gingivalis
<220> FEATURE:
<221> NAME/KEY: VARIANT
<222> LOCATION: 4
<223> OTHER INFORMATION: Xaa = Any Amino Acid

<400> SEQUENCE: 91

Leu Lys Trp Xaa Ala Pro
 1               5

<210> SEQ ID NO 92
<211> LENGTH: 11
<212> TYPE: PRT
<213> ORGANISM: Porphyromonas gingivalis

<400> SEQUENCE: 92

Thr Ala Thr Thr Phe Glu Glu Asp Gly Val Ala
 1               5                  10

<210> SEQ ID NO 93
<211> LENGTH: 10
<212> TYPE: PRT
<213> ORGANISM: Porphyromonas gingivalis

<400> SEQUENCE: 93

Trp Lys Thr Ile Asp Ala Asp Gly Asp Gly
 1               5                  10

<210> SEQ ID NO 94
<211> LENGTH: 10
<212> TYPE: PRT
<213> ORGANISM: Porphyromonas gingivalis

<400> SEQUENCE: 94

Val Tyr Arg Asp Gly Thr Lys Ile Lys Glu
 1               5                  10

<210> SEQ ID NO 95
<211> LENGTH: 15
<212> TYPE: PRT
```

<213> ORGANISM: Porphyromonas gingivalis

<400> SEQUENCE: 95

Trp Glu Ile Arg Thr Val Asp Leu Pro Ala Gly Thr Lys Tyr Val
1               5                   10                  15

<210> SEQ ID NO 96
<211> LENGTH: 12
<212> TYPE: PRT
<213> ORGANISM: Porphyromonas gingivalis

<400> SEQUENCE: 96

Glu Phe Ala Pro Val Gln Asn Leu Thr Gly Ser Ala
1               5                   10

<210> SEQ ID NO 97
<211> LENGTH: 32
<212> TYPE: PRT
<213> ORGANISM: Porphyromonas gingivalis

<400> SEQUENCE: 97

Ala Asn Glu Ala Lys Val Val Leu Ala Ala Asp Asn Val Trp Gly Asp
1               5                   10                  15

Asn Thr Gly Tyr Gln Phe Leu Leu Asp Ala Asp His Asn Thr Phe Gly
            20                  25                  30

<210> SEQ ID NO 98
<211> LENGTH: 33
<212> TYPE: PRT
<213> ORGANISM: Porphyromonas gingivalis

<400> SEQUENCE: 98

Val Thr Leu Lys Trp Asp Ala Pro Asn Gly Thr Pro Asn Pro Asn Pro
1               5                   10                  15

Asn Pro Asn Pro Asn Pro Asn Pro Gly Thr Thr Thr Leu Ser Glu Ser
            20                  25                  30

Phe

<210> SEQ ID NO 99
<211> LENGTH: 507
<212> TYPE: PRT
<213> ORGANISM: Porphyromonas gingivalis

<400> SEQUENCE: 99

Tyr Thr Pro Val Glu Glu Lys Glu Asn Gly Arg Met Ile Val Ile Val
1               5                   10                  15

Pro Lys Lys Tyr Glu Glu Asp Ile Glu Asp Phe Val Asp Trp Lys Asn
            20                  25                  30

Gln Arg Gly Leu Arg Thr Glu Val Lys Val Ala Glu Asp Ile Ala Ser
        35                  40                  45

Pro Val Thr Ala Asn Ala Ile Gln Gln Phe Val Lys Gln Glu Tyr Glu
    50                  55                  60

Lys Glu Gly Asn Asp Leu Thr Tyr Val Leu Leu Val Gly Asp His Lys
65                  70                  75                  80

Asp Ile Pro Ala Lys Ile Thr Pro Gly Ile Lys Ser Asp Gln Val Tyr
                85                  90                  95

Gly Gln Ile Val Gly Asn Asp His Tyr Asn Glu Val Phe Ile Gly Arg
            100                 105                 110

Phe Ser Cys Glu Ser Lys Glu Asp Leu Lys Thr Gln Ile Asp Arg Thr
        115                 120                 125

-continued

```
Ile His Tyr Glu Arg Asn Ile Thr Thr Glu Asp Lys Trp Leu Gly Gln
    130                 135                 140

Ala Leu Cys Ile Ala Ser Ala Glu Gly Gly Pro Ser Ala Asp Asn Gly
145                 150                 155                 160

Glu Ser Asp Ile Gln His Glu Asn Ile Ile Ala Asn Leu Leu Thr Gln
                165                 170                 175

Tyr Gly Tyr Thr Lys Ile Ile Lys Cys Tyr Asp Pro Gly Val Thr Pro
            180                 185                 190

Lys Asn Ile Ile Asp Ala Phe Asn Gly Ile Ser Leu Ala Asn Tyr
                195                 200                 205

Thr Gly His Gly Ser Glu Thr Ala Trp Gly Thr Ser His Phe Gly Thr
    210                 215                 220

Thr His Val Lys Gln Leu Thr Asn Ser Asn Gln Leu Pro Phe Ile Phe
225                 230                 235                 240

Asp Val Ala Cys Val Asn Gly Asp Phe Leu Tyr Asn Val Pro Cys Phe
                245                 250                 255

Ala Glu Ala Leu Met Arg Ala Gln Lys Asp Gly Lys Pro Thr Gly Thr
            260                 265                 270

Val Ala Ile Ile Ala Ser Thr Ile Asn Gln Ser Trp Ala Ser Pro Met
    275                 280                 285

Arg Gly Gln Asp Glu Met Asn Glu Ile Leu Cys Glu Lys His Pro Asn
    290                 295                 300

Asn Ile Lys Arg Thr Phe Gly Gly Val Thr Met Asn Gly Met Phe Ala
305                 310                 315                 320

Met Val Glu Lys Tyr Lys Lys Asp Gly Glu Lys Met Leu Asp Thr Trp
                325                 330                 335

Thr Val Phe Gly Asp Pro Ser Leu Leu Val Arg Thr Leu Val Pro Thr
            340                 345                 350

Lys Met Gln Val Thr Ala Pro Ala Asn Ile Ser Ala Ser Ala Gln Thr
    355                 360                 365

Phe Glu Val Ala Cys Asp Tyr Asn Gly Ala Ile Ala Thr Leu Ser Asp
370                 375                 380

Asp Gly Asp Met Val Gly Thr Ala Ile Val Lys Asp Gly Lys Ala Ile
385                 390                 395                 400

Ile Lys Leu Asn Glu Ser Ile Ala Asp Glu Thr Asn Leu Thr Leu Thr
                405                 410                 415

Val Val Gly Tyr Asn Lys Val Thr Val Ile Lys Asp Val Lys Val Glu
            420                 425                 430

Gly Thr Ser Ile Ala Asp Val Ala Asn Asp Lys Pro Tyr Thr Val Ala
    435                 440                 445

Val Ser Gly Lys Thr Ile Thr Val Glu Ser Pro Ala Ala Gly Leu Thr
    450                 455                 460

Ile Phe Asp Met Asn Gly Arg Arg Val Ala Thr Ala Lys Asn Arg Met
465                 470                 475                 480

Val Phe Glu Ala Gln Asn Gly Val Tyr Ala Val Arg Ile Ala Thr Glu
                485                 490                 495

Gly Lys Thr Tyr Thr Glu Lys Val Ile Val Lys
            500                 505
```

<210> SEQ ID NO 100
<211> LENGTH: 491
<212> TYPE: PRT
<213> ORGANISM: Porphyromonas gingivalis

```
<400> SEQUENCE: 100

Tyr Thr Pro Val Glu Glu Lys Gln Asn Gly Arg Met Ile Val Ile Val
  1               5                  10                  15

Ala Lys Lys Tyr Glu Gly Asp Ile Lys Asp Phe Val Asp Trp Lys Asn
             20                  25                  30

Gln Arg Gly Leu Arg Thr Glu Val Lys Val Ala Glu Asp Ile Ala Ser
         35                  40                  45

Pro Val Thr Ala Asn Ala Ile Gln Gln Phe Val Lys Gln Glu Tyr Glu
     50                  55                  60

Lys Glu Gly Asn Asp Leu Thr Tyr Val Leu Leu Ile Gly Asp His Lys
 65                  70                  75                  80

Asp Ile Pro Ala Lys Ile Thr Pro Gly Ile Lys Ser Asp Gln Val Tyr
                 85                  90                  95

Gly Gln Ile Val Gly Asn Asp His Tyr Asn Glu Val Phe Ile Gly Arg
                100                 105                 110

Phe Ser Cys Glu Ser Lys Glu Asp Leu Lys Thr Gln Ile Asp Arg Thr
            115                 120                 125

Ile His Tyr Glu Arg Asn Ile Thr Thr Glu Asp Lys Trp Leu Gly Gln
        130                 135                 140

Ala Leu Cys Ile Ala Ser Ala Glu Gly Gly Pro Ser Ala Asp Asn Gly
145                 150                 155                 160

Glu Ser Asp Ile Gln His Glu Asn Val Ile Ala Asn Leu Leu Thr Gln
                165                 170                 175

Tyr Gly Tyr Thr Lys Ile Ile Lys Cys Tyr Asp Pro Gly Val Thr Pro
            180                 185                 190

Lys Asn Ile Ile Asp Ala Phe Asn Gly Gly Ile Ser Leu Ala Asn Tyr
            195                 200                 205

Thr Gly His Gly Ser Glu Thr Ala Trp Gly Thr Ser His Phe Gly Thr
        210                 215                 220

Thr His Val Lys Gln Leu Thr Asn Ser Asn Gln Leu Pro Phe Ile Phe
225                 230                 235                 240

Asp Val Ala Cys Val Asn Gly Asp Phe Leu Phe Ser Met Pro Cys Phe
                245                 250                 255

Ala Glu Ala Leu Met Arg Ala Gln Lys Asp Gly Lys Pro Thr Gly Val
            260                 265                 270

Ala Ile Ile Ala Ser Thr Ile Asn Gln Ser Trp Ala Ser Pro Met Arg
        275                 280                 285

Gly Gln Asp Glu Met Asn Glu Ile Leu Cys Glu Lys His Pro Asn Asn
    290                 295                 300

Ile Lys Arg Thr Phe Gly Gly Val Thr Met Asn Gly Met Phe Ala Met
305                 310                 315                 320

Val Glu Lys Tyr Lys Lys Asp Gly Glu Lys Met Leu Asp Thr Trp Thr
                325                 330                 335

Val Phe Gly Asp Pro Ser Leu Leu Val Arg Thr Leu Val Pro Thr Lys
            340                 345                 350

Met Gln Val Thr Ala Pro Ala Gln Ile Asn Leu Thr Asp Ala Ser Val
        355                 360                 365

Asn Val Ser Cys Asp Tyr Asn Gly Ala Ile Ala Thr Ile Ser Ala Asn
    370                 375                 380

Gly Lys Met Phe Gly Ser Ala Val Val Glu Asn Gly Thr Ala Thr Ile
385                 390                 395                 400

Asn Leu Thr Gly Leu Thr Asn Glu Ser Thr Leu Thr Leu Thr Val Val
                405                 410                 415
```

```
Gly Tyr Asn Lys Glu Thr Val Ile Lys Thr Ile Asn Thr Asn Gly Glu
            420                 425                 430

Pro Asn Pro Tyr Gln Pro Val Ser Asn Leu Thr Ala Thr Thr Gln Gly
            435                 440                 445

Gln Lys Val Thr Leu Lys Trp Asp Ala Pro Ser Thr Lys Thr Asn Ala
            450                 455                 460

Thr Thr Asn Thr Ala Arg Ser Val Asp Gly Ile Arg Glu Leu Val Leu
465                 470                 475                 480

Leu Ser Val Ser Asp Ala Pro Glu Leu Leu Arg
            485                 490

<210> SEQ ID NO 101
<211> LENGTH: 509
<212> TYPE: PRT
<213> ORGANISM: Porphyromonas gingivalis

<400> SEQUENCE: 101

Asp Val Tyr Thr Asp His Gly Asp Leu Tyr Asn Thr Pro Val Arg Met
1               5                   10                  15

Leu Val Val Ala Gly Ala Lys Phe Lys Glu Ala Leu Lys Pro Trp Leu
            20                  25                  30

Thr Trp Lys Ala Gln Lys Gly Phe Tyr Leu Asp Val His Tyr Thr Asp
            35                  40                  45

Glu Ala Glu Val Gly Thr Thr Asn Ala Ser Ile Lys Ala Phe Ile His
        50                  55                  60

Lys Lys Tyr Asn Asp Gly Leu Ala Ala Ser Ala Ala Pro Val Phe Leu
65                  70                  75                  80

Ala Leu Val Gly Asp Thr Asp Val Ile Ser Gly Glu Lys Gly Lys Lys
            85                  90                  95

Thr Lys Lys Val Thr Asp Leu Tyr Tyr Ser Ala Val Asp Gly Asp Tyr
            100                 105                 110

Phe Pro Glu Met Tyr Thr Phe Arg Met Ser Ala Ser Ser Pro Glu Glu
            115                 120                 125

Leu Thr Asn Ile Ile Asp Lys Val Leu Met Tyr Glu Lys Ala Thr Met
130                 135                 140

Pro Asp Lys Ser Tyr Leu Glu Lys Val Leu Leu Ile Ala Gly Ala Asp
145                 150                 155                 160

Tyr Ser Trp Asn Ser Gln Val Gly Gln Pro Thr Ile Lys Tyr Gly Met
            165                 170                 175

Gln Tyr Tyr Asn Gln Glu His Gly Tyr Thr Asp Val Tyr Asn Tyr
            180                 185                 190

Leu Lys Ala Pro Tyr Thr Gly Cys Tyr Ser His Leu Asn Thr Gly Val
            195                 200                 205

Ser Phe Ala Asn Tyr Thr Ala His Gly Ser Glu Thr Ala Trp Ala Asp
            210                 215                 220

Pro Leu Leu Thr Thr Ser Gln Leu Lys Ala Leu Thr Asn Lys Asp Lys
225                 230                 235                 240

Tyr Phe Leu Ala Ile Gly Asn Cys Cys Ile Thr Ala Gln Phe Asp Tyr
            245                 250                 255

Val Gln Pro Cys Phe Gly Glu Val Ile Thr Arg Val Lys Glu Lys Gly
            260                 265                 270

Ala Tyr Ala Tyr Ile Gly Ser Ser Pro Asn Ser Tyr Trp Gly Glu Asp
            275                 280                 285

Tyr Tyr Trp Ser Val Gly Ala Asn Ala Val Phe Gly Val Gln Pro Thr
```

```
              290                 295                 300
    Phe Glu Gly Thr Ser Met Gly Ser Tyr Asp Ala Thr Phe Leu Glu Asp
    305                 310                 315                 320

Ser Tyr Asn Thr Val Asn Ser Ile Met Trp Ala Gly Asn Leu Ala Ala
                    325                 330                 335

Thr His Ala Gly Asn Ile Gly Asn Ile Thr His Ile Gly Ala His Tyr
                340                 345                 350

Tyr Trp Glu Ala Tyr His Val Leu Gly Asp Gly Ser Val Met Pro Tyr
                355                 360                 365

Arg Ala Met Pro Lys Thr Asn Thr Tyr Thr Leu Pro Ala Ser Leu Pro
    370                 375                 380

Gln Asn Gln Ala Ser Tyr Ser Ile Gln Ala Ser Ala Gly Ser Tyr Val
    385                 390                 395                 400

Ala Ile Ser Lys Asp Gly Val Leu Tyr Gly Thr Gly Val Ala Asn Ala
                    405                 410                 415

Ser Gly Val Ala Thr Val Ser Met Thr Lys Gln Ile Thr Glu Asn Gly
                420                 425                 430

Asn Tyr Asp Val Val Ile Thr Arg Ser Asn Tyr Leu Pro Val Ile Lys
                435                 440                 445

Gln Ile Gln Val Gly Glu Pro Ser Pro Tyr Gln Pro Val Ser Asn Leu
    450                 455                 460

Thr Ala Thr Gln Gly Gln Lys Val Thr Leu Lys Trp Glu Ala Pro
    465                 470                 475                 480

Ser Ala Lys Lys Ala Glu Gly Ser Arg Glu Val Lys Arg Ile Gly Asp
                    485                 490                 495

Gly Leu Phe Val Thr Ile Glu Pro Ala Asn Asp Val Arg
                500                 505

<210> SEQ ID NO 102
<211> LENGTH: 4
<212> TYPE: PRT
<213> ORGANISM: Porphyromonas gingivalis

<400> SEQUENCE: 102

Thr Leu Cys Lys
 1

<210> SEQ ID NO 103
<211> LENGTH: 11
<212> TYPE: PRT
<213> ORGANISM: Porphyromonas gingivalis

<400> SEQUENCE: 103

Thr Ala Thr Thr Phe Glu Glu Asp Gly Val Ala
 1               5                  10

<210> SEQ ID NO 104
<211> LENGTH: 10
<212> TYPE: PRT
<213> ORGANISM: Porphyromonas gingivalis

<400> SEQUENCE: 104

Trp Lys Thr Ile Asp Ala Asp Gly Asp Gly
 1               5                  10

<210> SEQ ID NO 105
<211> LENGTH: 736
<212> TYPE: PRT
<213> ORGANISM: Porphyromonas gingivalis
```

<400> SEQUENCE: 105

| | | | | | | | | | | | | | | |
|---|---|---|---|---|---|---|---|---|---|---|---|---|---|---|
|Met|Lys|Lys|Asn|Phe|Ser|Arg|Ile|Val|Ser|Ile|Val|Ala|Phe|Ser|Ser|
|1| | | |5| | | |10| | | |15| | |

Leu Leu Gly Gly Met Ala Phe Ala Gln Pro Ala Glu Arg Gly Arg Asn
           20                  25                  30

Pro Gln Val Arg Leu Leu Ser Ala Glu Gln Ser Met Ser Lys Val Gln
           35                  40                  45

Phe Arg Met Asp Asn Leu Gln Phe Thr Gly Val Gln Thr Ser Lys Gly
50                     55                  60

Val Ala Gln Val Pro Thr Phe Thr Glu Gly Val Asn Ile Ser Glu Lys
65                   70                  75                  80

Gly Thr Pro Ile Leu Pro Ile Leu Ser Arg Ser Leu Ala Val Ser Glu
                   85                  90                  95

Thr Arg Ala Met Lys Val Glu Val Ser Ser Lys Phe Ile Glu Lys
                  100               105              110

Lys Asp Val Leu Ile Ala Pro Ser Lys Gly Val Ile Ser Arg Ala Glu
          115                  120                  125

Asn Pro Asp Gln Ile Pro Tyr Val Tyr Gly Gln Ser Tyr Asn Glu Asp
          130                  135                  140

Lys Phe Pro Gly Glu Ile Ala Thr Leu Ser Asp Pro Phe Ile Leu
145                  150                  155              160

Arg Asp Val Arg Gly Gln Val Val Asn Phe Ala Pro Leu Gln Tyr Asn
                  165                170              175

Pro Val Thr Lys Thr Leu Arg Ile Tyr Thr Glu Ile Val Val Ala Val
           180                  185                  190

Ser Glu Thr Ala Glu Ala Gly Gln Asn Thr Ile Ser Leu Val Lys Asn
          195                  200                  205

Ser Thr Phe Thr Gly Phe Glu Asp Ile Tyr Lys Ser Val Phe Met Asn
          210                  215                  220

Tyr Glu Ala Thr Arg Tyr Thr Pro Val Glu Glu Lys Glu Asn Gly Arg
225                  230                  235              240

Met Ile Val Ile Val Pro Lys Lys Tyr Glu Glu Asp Ile Glu Asp Phe
                  245                250              255

Val Asp Trp Lys Asn Gln Arg Gly Leu Arg Thr Glu Val Lys Val Ala
          260                  265                  270

Glu Asp Ile Ala Ser Pro Val Thr Ala Asn Ala Ile Gln Gln Phe Val
          275                  280                  285

Lys Gln Glu Tyr Glu Lys Glu Gly Asn Asp Leu Thr Tyr Val Leu Leu
          290                  295                  300

Val Gly Asp His Lys Asp Ile Pro Ala Lys Ile Thr Pro Gly Ile Lys
305                  310                  315              320

Ser Asp Gln Val Tyr Gly Gln Ile Val Gly Asn Asp His Tyr Asn Glu
                  325                330              335

Val Phe Ile Gly Arg Phe Ser Cys Glu Ser Lys Glu Asp Leu Lys Thr
                  340                345              350

Gln Ile Asp Arg Thr Ile His Tyr Glu Arg Asn Ile Thr Thr Glu Asp
          355                  360                  365

Lys Trp Leu Gly Gln Ala Leu Cys Ile Ala Ser Ala Glu Gly Gly Pro
          370                  375                  380

Ser Ala Asp Asn Gly Glu Ser Asp Ile Gln His Glu Asn Ile Ile Ala
385                  390                  395              400

Asn Leu Leu Thr Gln Tyr Gly Tyr Thr Lys Ile Ile Lys Cys Tyr Asp

-continued

```
                    405                 410                 415
Pro Gly Val Thr Pro Lys Asn Ile Ile Asp Ala Phe Asn Gly Gly Ile
            420                 425                 430

Ser Leu Ala Asn Tyr Thr Gly His Gly Ser Glu Thr Ala Trp Gly Thr
            435                 440                 445

Ser His Phe Gly Thr Thr His Val Lys Gln Leu Thr Asn Ser Asn Gln
    450                 455                 460

Leu Pro Phe Ile Phe Asp Val Ala Cys Val Asn Gly Asp Phe Leu Tyr
465                 470                 475                 480

Asn Val Pro Cys Phe Ala Glu Ala Leu Met Arg Ala Gln Lys Asp Gly
                485                 490                 495

Lys Pro Thr Gly Thr Val Ala Ile Ile Ala Ser Thr Ile Asn Gln Ser
            500                 505                 510

Trp Ala Ser Pro Met Arg Gly Gln Asp Glu Met Asn Glu Ile Leu Cys
            515                 520                 525

Glu Lys His Pro Asn Asn Ile Lys Arg Thr Phe Gly Gly Val Thr Met
            530                 535                 540

Asn Gly Met Phe Ala Met Val Glu Lys Tyr Lys Lys Asp Gly Glu Lys
545                 550                 555                 560

Met Leu Asp Thr Trp Thr Val Phe Gly Asp Pro Ser Leu Leu Val Arg
                565                 570                 575

Thr Leu Val Pro Thr Lys Met Gln Val Thr Ala Pro Ala Asn Ile Ser
            580                 585                 590

Ala Ser Ala Gln Thr Phe Glu Val Ala Cys Asp Tyr Asn Gly Ala Ile
        595                 600                 605

Ala Thr Leu Ser Asp Asp Gly Asp Met Val Gly Thr Ala Ile Val Lys
    610                 615                 620

Asp Gly Lys Ala Ile Ile Lys Leu Asn Glu Ser Ile Ala Asp Glu Thr
625                 630                 635                 640

Asn Leu Thr Leu Thr Val Val Gly Tyr Asn Lys Val Thr Val Ile Lys
                645                 650                 655

Asp Val Lys Val Glu Gly Thr Ser Ile Ala Asp Val Ala Asn Asp Lys
                660                 665                 670

Pro Tyr Thr Val Ala Val Ser Gly Lys Thr Ile Thr Val Glu Ser Pro
            675                 680                 685

Ala Ala Gly Leu Thr Ile Phe Asp Met Asn Gly Arg Arg Val Ala Thr
    690                 695                 700

Ala Lys Asn Arg Met Val Phe Glu Ala Gln Asn Gly Val Tyr Ala Val
705                 710                 715                 720

Arg Ile Ala Thr Glu Gly Lys Thr Tyr Thr Glu Lys Val Ile Val Lys
                725                 730                 735
```

SYNTHETIC PEPTIDE CONSTRUCTS FOR THE DIAGNOSIS AND TREATMENT OF PERIODONTITIS ASSOCIATED WITH *PORPHYROMONAS GINGIVALIS*

CROSS-REFERENCE TO RELATED APPLICATIONS

This application is a continuation of U.S. Ser. No. 09/423,056, filed Mar. 22, 2000 now abandoned, which claims priority to PCT/AU98/00311, filed Apr. 30, 1998, which claims priority to Australian provisional application no. PO6528, filed Apr. 30, 1997, the contents of which are incorporated herein in their entirety.

FIELD OF THE INVENTION

This invention relates to an oral composition and an immunogenic composition for the suppression of the pathogenic effects of the intra-oral bacterium *Porphyromonas gingivalis* associated with periodontal disease. It also relates to diagnostic tests for the presence of *Porphyromonas gingivalis* in subgingival plaque samples and specific antibodies against *P. gingivalis* antigens in sera. The compositions comprise synthetic peptide constructs corresponding to structurally and functionally significant areas of the PrtR-PrtK proteinase-adhesin complex of *Porphyromonas gingivalis*. Also disclosed are methods for preparing the synthetic peptide constructs. The synthetic peptide constructs are useful as immunogens in raising an immune response against *P. gingivalis* and can be used to generate protein-specific and peptide-specific antisera useful for passive immunization and as reagents for diagnostic assays.

BACKGROUND OF THE INVENTION

Periodontal diseases are bacterial-associated inflammatory diseases of the supporting tissues of the teeth and range from the relatively mild form of gingivitis, the non-specific, reversible inflammation of gingival tissue to the more aggressive forms of periodontitis which are characterised by the destruction of the tooth's supporting structures. Periodontitis is associated with a subgingival infection of a consortium of specific Gram-negative bacteria that leads to the destruction of the periodontium and is a major public health problem. One bacterium that has attracted considerable interest is *Porphyromonas gingivalis* as the recovery of this microorganism from adult periodontitis lesions can be up to 50% of the subgingival anaerobically cultivable flora, whereas *P. gingivalis* is rarely recovered, and then in low numbers from healthy sites. A proportional increase in the level of *P. gingivalis* in subgingival plaque has been associated with an increased severity of periodontitis and eradication of the microorganism from the cultivable subgingival microbial population is accompanied by resolution of the disease. The progression of periodontitis lesions in non-human primates has been demonstrated with the subgingival implantation of *P. gingivalis*. These findings in both animals and humans suggest a major role for *P. gingivalis* in the development of adult periodontitis.

*P. gingivalis* is a black-pigmented, anaerobic, proteolytic Gram-negative rod that obtains energy from the metabolism of specific amino acids. The microorganism has an absolute growth requirement for iron, preferentially in the form of heme or its Fe(III) oxidation product hemin and when grown under conditions of excess hemin is highly virulent in experimental animals. A number of virulence factors have been implicated in the pathogenicity of *P. gingivalis* including the capsule, adhesins, cytotoxins and extracellular hydrolytic enzymes. In order to develop an efficacious and safe vaccine to prevent *P. gingivalis* colonisation it is necessary to identify effective antigens that are involved in virulence that have utility as immunogens to generate neutralising antibodies.

We have purified and characterised a 300 kDa multiprotein complex of cysteine proteinases and adhesins which is a major virulence factor for *P. gingivalis*. This complex was biochemically characterised and disclosed in International Patent Application No. PCT/AU96/00673, the disclosure of which is incorporated herein by reference. The complex consists of a 160 kDa Arg-specific proteinase with C-terminal adhesin domains (designated PrtR) associated with a 163 kDa Lys-specific proteinase also with C-terminal adhesin domains (designated PrtK). The C-terminal adhesin domains of the PrtR and PrtK have homology with all haemagglutinin from *P. gingivalis* designated HagA. The gene encoding HagA has been disclosed in the international patent WO96/17936, the disclosure of which is incorporated herein by reference.

SUMMARY OF THE INVENTION

The present inventors have identified a number of structurally and functionally significant sequences from the 300 kDa multiprotein complex of cysteine proteinases and adhesins which is a major virulence factor for *P. gingivalis*. These sequences are set out in Table 1.

TABLE 1

Amino acid sequences of the PrtR-PrtK proteinase-adhesin complex of functional significance.

| | Sequence (single letter code) | Designation | SEQ ID NO: |
|---|---|---|---|
| Proteinase Active Site | | | |
| PrtR45 (426–446) | FNGGISLANYTGHGSETAWGT | PAS1 (R45) | SEQ ID NO:1 |
| PrtK48 (432–453) | LNTGVSFANYTAHGSETAWADP | PAS1 (K48) | SEQ ID NO:2 |
| PrtR45 (467–490) | FDVACVNGDFLFSMPCFAEALMRA | PAS2 (R45) | SEQ ID NO:3 |
| PrtK48 (473–496) | IGNCCITAQFDYVQPCFGEVITRV | PAS2 (K48) | SEQ ID NO:4 |

TABLE 1-continued

Amino acid sequences of the PrtR-PrtK proteinase-adhesin complex of functional significance.

| | Sequence (single letter code) | Designation | SEQ ID NO: |
|---|---|---|---|
| Adhesin Binding Motif | | | |
| PrtR45 (660–689) | GEPNPYQPVSNLTATTQGQKVTLKWDAPSTK | ABM1 (R45) | SEQ ID NO:5 |
| PrtR44 (919–949) | EGSNEFAPVQNLTGSAVGQKVTLKWDAPNGT | ABM1 (R44) | SEQ ID NO:6 |
| PrtR17 (1375–1405) | VNSTQFNPVKNLKAQPDGGDVVLKWEAPSAK | ABM1 (R17) | SEQ ID NO:7 |
| PrtK48 (681–711) | GEPSPYQPVSNLTATTQGQKVTLKWEAPSAK | ABM1 (K48) | SEQ ID NO:8 |
| PrtK39 (940–970) | EGSNEFAPVQNLTGSSVGQKVTLKWDAPNGT | ABM1 (K39) | SEQ ID NO:9 |
| PrtK44 (1393–1425) | VNSTQFNPVQNLTAEQAPNSMDAILKWNAPASK | ABM1 (K44) | SEQ ID NO:10 |
| HagA (1837–1863) | QFNPVQNLTGSAVGQKVTLKWDAPNGT | ABM1 (HagA1) | SEQ ID NO:11 |
| HagA (1381–1407) | QFNPVQNLTGSAVGQKVTLKWDAPNGT | ABM1 (HagA2) | SEQ ID NO:12 |
| HagA (925–951) | QFNPVQNLTGSAVGQKVTLKWDAPNGT | ABM1 (HagA3) | SEQ ID NO:13 |
| HagA (474–499) | FAHVQNLTGSAVGQKVTLKWDAPNGT | ABM1 (HaGA4) | SEQ ID NO:14 |
| HagA (202–227) | FAPVQNLQWSVSGQTVTLTWQAPASD | ABM1 (HagA5) | SEQ ID NO:15 |
| HagA (2293–2321) | QFNPVQNLTAEQAPNSMDAILKWNAPASK | ABM1 (HagA6) | SEQ ID NO:16 |
| PrtR44 (865–893) | DYTYTVYRDGTKIKEGLTATTFEEDGVAT | ABM2 (R44) | SEQ ID NO:17 |
| PrtR17 (1322–1350) | DYTYTVYRDGTKIKEGLTETTFEEDGVAT | ABM2 (R17) | SEQ ID NO:18 |
| PrtR27 (1580–1608) | SYTYTVYRDGTKIKEGLTETTYRDAGMSA | ABM2 (R27) | SEQ ID NO:19 |
| PrtK39 (886–914) | SYTYTVYRDGTKIKEGLTATTFEEDGVAA | ABM2 (K39) | SEQ ID NO:20 |
| PrtK44 (1340–1368) | DYTYTVYRDGTKIKEGLTETTFEEDGVAT | ABM2 (K44A) | SEQ ID NO:21 |
| PrtK44 (1606–1634) | SYTYTIYRNNTQIASGVTETTYRDPDLAT | ABM2 (K44B) | SEQ ID NO:22 |
| HagA (2236–2264) | DYTYTVYRDGTKIKEGLTETTFEEDGVAT | ABM2 (HagA1) | SEQ ID NO:23 |
| HagA (1780–1808) | DYTYTVYRDGTKIKEGLTETTFEEDGVAT | ABM2 (HagA2) | SEQ ID NO:24 |
| HagA (1324–1352) | DYTYTVYRDGTKIKEGLTETTFEEDGVAT | ABM2 (HagA3) | SEQ ID NO:25 |
| HagA (868–896) | DYTYTVYRDGTKIKEGLTETTFEEDGVAT | ABM2 (HagA4) | SEQ ID NO:26 |
| HagA (415–443) | DYTYTVYRDNVVIAQNLAATTFNQENVAP | ABM2 (HagA5) | SEQ ID NO:27 |
| HagA (2502–2530) | SYTYTIYRNNTQIASGVTETTYRDPDLAT | ABM2 (HagA6) | SEQ ID NO:28 |
| PrtR44 (946–971) | PNGTPNPNPNPNPNPNPGTTTLSESF | ABM3 (R44) | SEQ ID NO:29 |
| PrtK39 (967–989) | PNGTPNPNPNPNPNPGTTLSESF | ABM3 (K39) | SEQ ID NO:30 |
| HagA (1860–1881) | PNGTPNPNPNPNPNPGTTTLSESF | ABM3 (HagA1) | SEQ ID NO:31 |
| HagA (1404–1425) | PNGTPNPNPNPNPGTTTLSESF | ABM3 (HagA2) | SEQ ID NO:32 |
| HagA (948–969) | PNGTPNPNPNPNPGTTTLSESF | ABM3 (HagA3) | SEQ ID NO:33 |
| HagA (496–513) | PNGTPNPNPGTTTLSESF | ABM3 (HagA4) | SEQ ID NO:34 |
| PrtR17 (1278–1297) | WIERTVDLPAGTKYVAFRHY | ABM4 (R17) | SEQ ID NO:35 |
| PrtR44 (1028–1043) | WRQKTVDLPAGTKYVAFRHF | ABM4 (R44) | SEQ ID NO:36 |
| PrtK44 (1296–1315) | WIERTVDLPAGTKYVAFRHY | ABM4 (K44A) | SEQ ID NO:37 |
| PrtK44 (1565–1584) | WRQKTVDLPAGTKYVAFRHF | ABM4 (K44B) | SEQ ID NO:38 |
| PrtK39 (1116–1135) | WYQKTVQLPAGTKYVAFRHF | ABM4 (K39) | SEQ ID NO:39 |
| HagA (2191–2211) | WIERTVDLPAGTKYVAFRHY | ABM4 (HagA1) | SEQ ID NO:40 |

TABLE 1-continued

Amino acid sequences of the PrtR-PrtK proteinase-adhesin complex of functional significance.

| | Sequence (single letter code) | Designation | SEQ ID NO: |
|---|---|---|---|
| HagA (1736–1755) | WIERTVDLPAGTKYVAFRHY | ABM4 (HagA2) | SEQ ID NO:41 |
| HagA (1280–1299) | WIERTVDLPAGTKYVAFRHY | ABM4 (HagA3) | SEQ ID NO:42 |
| HagA (824–843) | WIERTVDLPAGTKYVAFRHY | ABM4 (HagA4) | SEQ ID NO:43 |
| HagA (2012–2031) | WYQKTVQLPAGTKYVAFRHF | ABM4 (HagA5) | SEQ ID NO:44 |
| HagA (1556–1575) | WYQKTVQLPAGTKYVAFRHF | ABM4 (HagA6) | SEQ ID NO:45 |
| HagA (2461–2480) | WYQKTVQLPAGTKYVAFRHF | ABM4 (HagA7) | SEQ ID NO:46 |
| HagA (1100–1119) | WYQKTVQLPAGTKYVAFRHF | ABM4 (HagA8) | SEQ ID NO:47 |
| HagA (644–663) | WYQKTVQLPAGTKYVAFRHF | ABM4 (HagA9) | SEQ ID NO:48 |
| HagA (372–392) | ERTIDLSAYAGQQVYLAFRHF | ABM4 (HagA10) | SEQ ID NO:49 |
| PrtR15 (1154–1169) | PAEWTTIDADGDGQGW | ABM5 (R15) | SEQ ID NO:50 |
| PrtR44 (976–991) | PASWKTIDADGDGHGW | ABM5 (R44) | SEQ ID NO:51 |
| PrtK15 (1172–1187) | PAEWTTIDADGDGQGW | ABM5 (K15) | SEQ ID NO:52 |
| PrtK39 (994–1009) | PASWKTIDADGDGHGW | ABM5 (K39) | SEQ ID NO:53 |
| PrtK44 (1439–1454) | PASWKTIDADGDGNNW | ABM5 (K44) | SEQ ID NO:54 |
| HagA (2068–2083) | PAEWTTIDADGDGQGW | ABM5 (HagA1) | SEQ ID NO:55 |
| HagA (1612–1627) | PAEWTTIDADGDGQGW | ABM5 (HagA2) | SEQ ID NO:56 |
| HagA (1156–1171) | PAEWTTIDADGDGQGW | ABM5 (HagA3) | SEQ ID NO:57 |
| HagA (700–715) | PAEWTTIDADGDGQGW | ABM5 (HagA4) | SEQ ID NO:58 |
| HagA (1430–1445) | PASWKTIDADGDGNNW | ABM5 (HagA5) | SEQ ID NO:59 |
| HagA (974–989) | PASWKTIDADGDGNNW | ABM5 (HagA6) | SEQ ID NO:60 |
| HagA (1886–1901) | PASWKTIDADGDGNNW | ABM5 (HagA7) | SEQ ID NO:61 |
| HagA (518–533) | PASWKTIDADGDGNNW | ABM5 (HagA8) | SEQ ID NO:62 |
| HagA (2335–2350) | PSSWKTIDADGDGNNW | ABM5 (HagA9) | SEQ ID NO:63 |
| HagA (243–258) | PNGWTMIDADGDGHNW | ABM5 (HagA10) | SEQ ID NO:64 |
| PrtR44 (919–938) | EGSNEFAPVQNLTGSAVGQK | ABM6 (R44) | SEQ ID NO:65 |
| PrtR45 (659–678) | GEPNPYQPVSNLTATTQGQK | ABM6 (R45) | SEQ ID NO:66 |
| PrtK39 (940–959) | EGSNEFAPVQNLTGSSVGQK | ABM6 (K39) | SEQ ID NO:67 |
| PrtK48 (681–700) | GEPSPYQPVSNLTATTQGQK | ABM6 (K48) | SEQ ID NO:68 |
| PrtK44 (1394–1412) | NSTQFNPVQNLTAEQAPNS | ABM6 (K44) | SEQ ID NO:69 |
| HagA (469–488) | EGSNEFAHVQNLTGSAVGQK | ABM6 (HagA1) | SEQ ID NO:70 |
| HagA (1834–1852) | DPVQFNPVQNLTGSAVGQK | ABM6 (HagA2) | SEQ ID NO:71 |
| HagA (1378–1396) | DPVQFNPVQNLTGSAVGQK | ABM6 (HagA3) | SEQ ID NO:72 |
| HagA (922–940) | DPVQFNPVQNLTGSAVGQK | ABM6 (HagA4) | SEQ ID NO:73 |
| HagA (197–216) | EGGNEFAPVQNLQWSVSGQT | ABM6 (HagA5) | SEQ ID NO:74 |
| HagA (2290–2308) | NPTQFNPVQNLTAEQAPNS | ABM6 (HagA6) | SEQ ID NO:75 |
| PrtR44 (894–918) | GNHEYCVEVKYTAGVSPKVCKDVTV | ABM7 (R44) | SEQ ID NO:76 |
| PrtR17 (1351–1375) | GNHEYCVEVKYTAGVSPKKCNVTV | ABM7 (R17) | SEQ ID NO:77 |
| PrtR27 (1610–1630) | SHEYCVEVKYTAGVSPKVCVD | ABM7 (R27) | SEQ ID NO:78 |

TABLE 1-continued

Amino acid sequences of the PrtR-PrtK proteinase-adhesin complex of functional significance.

| | Sequence (single letter code) | Designation | SEQ ID NO: |
|---|---|---|---|
| PrtK39 (915–939) | GNHEYCVEVKYTAGVSPKVCKDVTV | ABM7 (K39) | SEQ ID NO:79 |
| PrtK44 (1369–1393) | GNHEYCVEVKYTAGVSPKKCVNVTV | ABM7 (K44) | SEQ ID NO:80 |
| HagA (2265–2289) | GNHEYCVEVKYTAGVSPKVCVNVTI | ABM7 (Hag1) | SEQ ID NO:81 |
| HagA (444–468) | GQYNYCVEVKYTAGVSPKVCKDVTV | ABM7 (Hag2) | SEQ ID NO:82 |
| HagA (1809–1833) | GNHEYCVEVKYTAGVSPEVCVNVTV | ABM7 (Hag3) | SEQ ID NO:83 |
| HagA (1353–1377) | GNHEYCVEVKYTAGVSPEVCVNVTV | ABM7 (Hag4) | SEQ ID NO:84 |
| HagA (897–921) | GNHEYCVEVKYTAGVSPEVCVNVTV | ABM7 (Hag5) | SEQ ID NO:85 |

Accordingly in a first aspect the present invention consists in a composition for use in raising an immune response against *Porphyromonas gingivalis*, the composition including a suitable adjuvant and/or acceptable carrier or excipient and at least one peptide selected from the group consisting of:—

FNGGISLANYTGHGSETAWGT (SEQ ID NO:1);

LNTGVSFANYTAHGSETAWADP (SEQ ID NO:2);

FDVACVANGDFLFSMPCFAEALMRA (SEQ ID NO:3);

IGNCCITAQFDYVQPCFGEVITRV (SEQ ID NO:4);

GEPNPYQPVSNLTATTQGQKVTLKWDAPSTK (SEQ ID NO:5);

EGSNEFAPVQNLTGSAVGQKVTLKWDAPNGT (SEQ ID NO:6);

VNSTQFNPVKNLKAQPDGGDVVLKWEAPSAK (SEQ ID NO:7);

GEPSPYQPVSNLTATTQGQKVTLKWEAPSAK (SEQ ID NO:8);

EGSNEFAPVQNLTGSSVGQKVTLKWDAPNGT (SEQ ID NO:9);

VNSTQFNPVQNLTAEQAPNSMDAILKWNAPASK (SEQ ID NO:10);

QFNPVQNLTGSAVGQKVTLKWDAPNGT (SEQ ID NO:11);

FAHVQNLTGSAVGQKVTLKWDAPNGT (SEQ ID NO:14);

FAPVQNLQWSVSGQTVTLTWQAPASD (SEQ ID NO:15);

QFNPVQNLTAEQAPNSMDAILKWNAPASK (SEQ ID NO:16);

DYTYTVYRDGTKIKEGLTATTFEEDGVAT (SEQ ID NO:17);

DYTYTVYRDGTKIKEGLTETTFEEDGVAT (SEQ ID NO:18);

SYTYTVYRDGTKIKEGLTETTYRDAGMSA (SEQ ID NO:19);

SYTYTVYRDGTKIKEGLTATTFEEDGVAA (SEQ ID NO:20);

DYTYTVYRDGTKIKEGLTETTFEEDGVAT (SEQ ID NO:21);

SYTYTIYRNNTQIASGVTETTYRDPDLAT (SEQ ID NO:22);

DYTYTVYRDNVVIAQNLAATTFNQENVAP (SEQ ID NO:27);

SYTYTIYRNNTQIASGVTETTYRDPDLAT (SEQ ID NO:28);

PNGTPNPNPNPNPNPNPGTTTLSESF (SEQ ID NO:29);

PNGTPNPNPNPNPNPGTTLSESF (SEQ ID NO:30);

PNGTPNPNPNPNPGTTTLSESF (SEQ ID NOS:31-33);

PNGTPNPNPGTTTLSESF (SEQ ID NO:34);

WIERTVDLPAGTKYVAFRHY (SEQ ID NOS:35 and 37);

WRQKTVDLPAGTKYVAFRHF (SEQ ID NOS:36 and 38);

WYQKTVQLPAGTKYVAFRHF (SEQ ID NO:39);

ERTIDLSAYAGQQVYLAFRHF (SEQ ID NO:49);

PAEWTTIDADGDGQGW (SEQ ID NOS:50,52 and 55-58);

PASWKTIDADGDGHGW (SEQ ID NOS:51 and 53);

PASWKTIDADGDGNNW (SEQ ID NOS:54 and 59-62);

PSSWKTIDADGDGNNW (SEQ ID NO:63);

PNGWTMIDADGDGHNW (SEQ ID NO:64);

EGSNEFAPVQNLTGSAVGQK (SEQ ID NO:65);

GEPNPYQPVSNLTATTQGQK (SEQ ID NO:66);

EGSNEFAPVQNLTGSSVGQK (SEQ ID NO:67);

GEPSPYQPVSNLTATTQGQK (SEQ ID NO:68);

NSTQFNPVQNLTAEQAPNS (SEQ ID NO:69);

EGSNEFAHVQNLTGSAVGQK (SEQ ID NO:70);

DPVQFNPVQNLTGSAVGQK (SEQ ID NOS:71-73);

EGGNEFAPVQNLQWSVSGQT (SEQ ID NO:74);

NPTQFNPVQNLTAEQAPNS (SEQ ID NO:75);

GNHEYCVEVKYTAGVSPKVCKDVTV (SEQ ID NO:76);

GNHEYCVEVKYTAGVSPKKCVNVTV (SEQ ID NOS:77 and 80);

SHEYCVEVKYTAGVSPKVCVD (SEQ ID NO:78);

GNHEYCVEVKYTAGVSPKCVNVTVI (SEQ ID NO:81);

GQYNYCVEVKYTAGVSPKVCKDVTV (SEQ ID NO:82);

GNHEYCVEVKYTAGVSPEVCVNVTV (SEQ ID NOS:83-85);

PYQPVSNLTATTQGQKVTLKWDAPSTK (SEQ ID NO:86); and

VTLKWDAPNGTPNPNPNPNPNPNPGTTTLSESF (SEQ ID NO:98).

In a preferred embodiment of the first aspect of the present invention, the composition includes at least one peptide selected from the group consisting of:—

FNGGISLANYTGHGSETAWGT (SEQ ID NO:1);

LNTGVSFANYTAHGSETAWADP (SEQ ID NO:2);

PYQPVSNLTATTQGQKVTLKWDAPSTK (SEQ ID NO:86);

SYTYTVYRDGTKIKEGLTATTFEEDGVAA (SEQ ID NO:20);

VTLKWDAPNGTPNPNPNPNPNPNPGTTTLSESF (SEQ ID NO:98);

WIERTVDLPAGTKYVAFRHY (SEQ ID NO:35);

PAEWTTIDADGDGQGW (SEQ ID NO:50); and

EGSNEFAPVQNLTGSAVGQK (SEQ ID NO:65).

Where the composition includes more than one peptide the peptides may be present in the composition as individual peptides or in multimeric forms. Where multimeric forms are used the multimer may comprise multiple copies of the same peptide, however, it is preferred that the multimer includes differing peptides.

Peptides (PAS1 and PAS2) of Table 1 represent sequences of the Arg-specific (PrtR45) and Lys-specific (PrtK48) cysteine proteinases which form the active site containing the Cys-His catalytic dyad.

The remaining peptides (ABM peptides) represent adhesin binding motifs of the PrtR-PrtK protein-adhesin complex and HagA and together with the proteinase active site sequences, have proven to be effective as synthetic peptide vaccines.

In a second aspect the present invention consists in a peptide, the peptide being selected from the group consisting of:—

FNGGISLANYTGHGSETAWGT (SEQ ID NO:1);

LNTGVSFANYTAHGSETAWADP (SEQ ID NO:2);

FDVACVNGDFLFSMPCFAEALMRA (SEQ ID NO:3);

IGNCCITAQFDYVQPCFGEVITRV (SEQ ID NO:4);

GEPNPYQPVSNLTATTQGQKVTLKWDAPSTK (SEQ ID NO:5);

EGSNEFAPVQNLTGSAVGQKVTLKWDAPNGT (SEQ ID NO:6);

VNSTQFNPVKNLKAQPDGGDVVLKWEAPSAK (SEQ ID NO:7);

GEPSPYQPVSNLTATTQGQKVTLKWEAPSAK (SEQ ID NO:8);

EGSNEFAPVQNLTGSSVGQKVTLKWDAPNGT (SEQ ID NO:9);

VNSTQFNPVQNLTAEQAPNSMDAILKWNAPASK (SEQ ID NO:10);

QFNPVQNLTGSAVGQKVTLKWDAPNGT (SEQ ID NO:11);

FAHVQNLTGSAVGQKVTLKWDAPNGT (SEQ ID NO:14);

FAPVQNLQWSVSGQTVTLTWQAPASD (SEQ ID NO:15);

QFNPVQNLTAEQAPNSMDAILKWNAPASK (SEQ ID NO:16);

DYTYTVYRDGTKIKEGLTATTFEEDGVAT (SEQ ID NO:17);

DYTYTVYRDGTKIKEGLTETTFEEDGVAT (SEQ ID NO:18);

SYTYTVYRDGTKIKEGLTETTYRDAGMSA (SEQ ID NO:19);

SYTYTVYRDGTKIKEGLTATTFEEDGVAA (SEQ ID NO:20);

-continued

DYTYTVYRDGTKIKEGLTETTFEEDGVAT (SEQ ID NO:21);

SYTYTIYRNNTQIASGVTETTYRDPDLAT (SEQ ID NO:22);

DYTYTVYRDNVVIAQNLAATTFNQENVAP (SEQ ID NO:27);

SYTYTIYRNNTQIASGVTETTYRDPDLAT (SEQ ID NO:28);

PNGTPNPNPNPNPNPNPGTTTLSESF (SEQ ID NO:29);

PNGTPNPNPNPNPNPGTTLSESF (SEQ ID NO:30);

PNGTPNPNPNPNPGTTTLSESF (SEQ ID NOS:31-33);

PNGTPNPNPGTTTLSESF (SEQ ID NO:34);

WIERTVDLPAGTKYVAFRHY (SEQ ID NOS:35 and 37);

WRQKTVDLPAGTKYVAFRHF (SEQ ID NOS:36 and 38);

WYQKTVQLPAGTKYVAFRHF (SEQ ID NO:39);

ERTIDLSAYAGQQVYLAFRHF (SEQ ID NO:49);

PAEWTTIDADGDGQGW (SEQ ID NOS:50,52 and 55-58);

PASWKTIDADGDGHGW (SEQ ID NOS:51 and 53);

PASWKTIDADGDGNNW (SEQ ID NO:54,59-62);

PSSWKTIDADGDGNNW (SEQ ID NO:63);

PNGWTMIDADGDGHNW (SEQ ID NO:64);

EGSNEFAPVQNLTGSAVGQK (SEQ ID NO:65);

GEPNPYQPVSNLTATTQGQK (SEQ ID NO:66);

EGSNEFAPVQNLTGSSVGQK (SEQ ID NO:67);

GEPSPYQPVSNLTATTQGQK (SEQ ID NO:68);

NSTQFNPVQNLTAEQAPNS (SEQ ID NO:69);

EGSNEFAHVQNLTGSAVGQK (SEQ ID NO:70);

DPVQFNPVQNLTGSAVGQK (SEQ ID NO:71-73);

EGGNEFAPVQNLQWSVSGQT (SEQ ID NO:74);

NPTQFNPVQNLTAEQAPNS (SEQ ID NO:75);

GNHEYCVEVKYTAGVSPKVCKDVTV (SEQ ID NO:76);

GNHEYCVEVKYTAGVSPKKCVNVTV (SEQ ID NOS:77 and 80);

SHEYCVEVKYTAGVSPKVCVD (SEQ ID NO:78);

GNHEYCVEVKYTAGVSPKVCVNVTI (SEQ ID NO:81);

GQYNYCVEVKYTAGVSPKVCKDVTV (SEQ ID NO:82);

GNHEYCVEVKYTAGVSPEVCVNVTV (SEQ ID NOS:83-85);

PYQPVSNLTATTQGQKVTLKWDAPSTK (SEQ ID NO:86); and

VTLKWDAPNGTPNPNPNPNPNPGTTTLSESF (SEQ ID NO:98).

In a preferred embodiment of the second aspect of the present invention, the peptide is selected from the group consisting of:—

FNGGISLANYTGHGSETAWGT (SEQ ID NO:1);

LNTGVSFANYTAHGSETAWADP (SEQ ID NO:2);

PYQPVSNLTATTQGQKVTLKWDAPSTK (SEQ ID NO:86);

```
-continued
SYTYTVYRDGTKIKEGLTATTFEEDGVAA (SEQ ID NO:20);

VTLKWDAPNGTPNPNPNPNPNPNPGTTTLSESF (SEQ ID NO:98);

WIERTVDLPAGTKYVAFRHY (SEQ ID NO:35);

PAEWTTIDADGDGQGW (SEQ ID NO:50); and

EGSNEFAPVQNLTGSAVGQK (SEQ ID NO:65).
```

As will be readily apparent to persons skilled in this area these peptides may be used as antigens in diagnostic tests or as immunogens in formulations.

In a third aspect the present invention consists in an antibody preparation comprising antibodies specifically directed against the composition of the first aspect of the invention or the peptides of the second aspect of the invention. The antibodies may be either polyclonal or monoclonal antibodies.

In a fourth aspect the present invention consists in a method of treating a subject suffering from *Porphyromonas gingivalis* infection, the method comprising administering to the subject an effective amount of the antibody preparation of the third aspect.

In a preferred embodiment the antibody preparation is administered as a mouth wash or as a dentifrice.

In a fifth aspect the present invention consists in a method of treating a subject suffering from *Porphyromonas gingivalis* infection the method comprising administering to the subject an effective amount of a composition of the first aspect of the invention or a peptide of the second aspect of the invention.

In a preferred embodiment the composition or peptide is administered as a mouth wash or as a dentifrice.

In a sixth aspect the present invention consists in a method of reducing the prospect of *P. gingivalis* infection in an individual and/or severity of disease, the method comprising administering to the individual an amount of the composition of the first aspect effective to induce an immune response in the individual directed against *P. Gingivalis*.

Throughout this specification, unless the context requires otherwise, the word "comprise", or variations such as "comprises" or "comprising", will be understood to imply the inclusion of a stated element or integer or group of elements or integers but not the exclusion of any other element or integer or croup of elements or integers.

Peptides can be synthesized using one of the several methods of peptide synthesis known in the art including standard solid phase peptide synthesis using t-butyloxycarbonyl amino acids (Mitchell et al., 1978. J. Org. Chem. 43:2845-2852) using 9-fluorenylmethyloxycarbonyl (Fmoc) amino acids on a polyamide support (Druland et al., 1986. J. Chem, Soc. Perkin Trans. 1 125-137) by pepscan synthesis (Geysen et al., 1987. J. Immunol Methods 03:259; 1984, Proc. Natl. Acad. Sci. USA, 81:3998) or by standard liquid phase synthesis.

A variety of methods for the synthesis of multivalent/multipeptide high molecular weight peptide molecules can be used to synthesize the peptide antigens. This will be achieved using known in the art and novel ligation strategies.

Preparation of Synthetic Peptides

Peptides from Table 1 can be synthesized in such away as to contain two ligands, which can be the same or different, which may or may not be the complementary ligand. These bi-modal peptides can incorporate any ligand thus linkages such as thioether, thioester, hydrazone, oxime, thiazolidine can be utilised for the synthesis of multipeptide constructs Shao and Tam., 1995, J. Am. Chem. Soc. 117, 3893-3899, Rose, et al 1996, Bioconjugate Chem. 7(5):552-556. Rose. K., 1994, J. Am. Chem. Soc. 116:30-33, Canne., et al 1995, J. Am. Chem. Soc. 117:2998-3007, Lu., et al. 1991, Mol. Immunol 28(6):623-630, Liu and Tam., 1994, Proc. Natl. Acad. Sci. 91.:6584-6588. A novel ligating strategy is to use the known reaction between thioanisole and acryloyl peptides (O'Brien-Simpson et al., 1997. J. Am. Chem. Soc. 119 (6) which results in the para substitution of thioanisole by the double bond in acidic conditions. By synthesising and mixing acryloyl-peptides and phenylthio acetyl peptides and exposing them to acidic conditions ligation can proceed by Friedal-Craft alkylation. Ligation can be accomplished between peptides and on to an oligolysine support derivatised with one of the ligands. Conditions for ligation can consist of; Friedal-Craft reaction conditions which are known in the art and known peptide cleavage conditions.

The introduction of ligand groups to form bi-modal peptides can be achieved by coupling a ligand on to free amino groups, which is known in the art at the N- or C-terminus of a peptide or within the peptide sequence. This can be achieved by coupling eg. Fmoc(Fmoc) 2,3 diamino propionic acid or Fmoc Lys (Fmoc)-OH or orthogonally protected lysine residues such as Fmoc Lys (Mtt)-OH using standard peptide coupling protocols on to the N-terminus or introduced at the C-terminus or within the peptide sequence. After deprotection, ligand groups can be coupled on to the amino groups and by selective deprotection of eg. Fmoc Lys (Mtt) different ligands can be coupled on to a single peptide. At any point in the synthesis spacer moieties can be introduced between the peptide and the ligands and/or between the ligands, which may be used to reduce steric hindrance in the ligation reaction. FIG. 1 shows the synthesis protocol.

Peptide ligation can be achieved in solution or on the solid phase. The incorporation of different ligands and selective protection of one ligand can allow the synthesis of multivalent, multipeptide constructs, where by, peptides are ligated sequentially. This strategy has the advantage that the orientation and order of peptides ligated is known and can be controlled. Protecting groups for ligands can be for example Fmoc, allyloxycarbonyl (Aloc) or nitrocinnamyloxycarbonyl (Noc) which are stable to standard cleavage conditions but are easily removed under basic conditions or catalytic allyl transfer. FIG. 2 shows the ligation scheme for the synthesis of multivalent peptide constructs using bi-modal peptides. The protocol can be adapted for a variety of ligation chemistries by simply altering the ligands which are coupled to the peptide to form the bi-modal peptide.

The step wise addition of each peptide can be achieved on the solid phase. This can be achieved by synthesising a peptide on to the solid support via a base labile handle eg. 4-hydroxymethyl benzoic acid. This can allow full side chain deprotection of the peptide with the peptide remaining attached to the solid support. This would allow ligation to still be carried out in aqueous solvents similar to those used for solution phase ligation except that separation of the ligand product from unreacted bi-modal peptide can be achieved by simply washing the solid support. The reaction can be monitored by ninhydrin or trinitrobenzene sulphonic acid tests, where by lysine residues within the bi-modal peptide would need to be protected eg. with (4,4-dimethyl-2,6-dioxocyclohex-1-ylidene)ethyl (Dde) which is stable to acid cleavage but can be removed with hydrazine. FIG. 3 shows the ligation strategy for the solid phase.

Bi-modal peptides can be synthesized so that ligands are at the N- and C-terminus. This would allow the preparation of cyclic peptides and the formation of di-peptide constructs where by peptides can run parallel or anti parallel to each other by either coupling N- to N- and C- to C-termini or N- to C-termini together respectively (FIG. 4). (SEQ ID NOS:1 and 3).

Another technique for the synthesis of multivalent peptide constructs is to ligate peptides on to an oligolysine support (Rose, et al 1996, Bioconjugate Chem. 7(5):552-556, Canne., et al 1995, J. Am. Chem. Soc. 117:2998-3007 and Lu., et al, 1991, Mol. Immunol 28(6):623-630). By incorporating a number of different ligands and or protected ligands on to the lysine support, peptides can be ligated to a particular position on the support. Ligation chemistries such as oxime or hydrazone with haloacylation and Friedal-Craft alkylation can be used sequentially without the need for ligand protection. Ligand protection can be used to increase the number of different peptides incorporated on to the lysine support. FIG. 5 (SEQ ID NOS:35 and 50) demonstrates the synthesis protocol.

Another method known in the art is the synthesis of acryloyl peptides and their polymerisation with acrylamide (O'Brien-Simpson et al., 1997, J. Am. Chem. Soc. 119 (6)) or acryloyl amino acids. Peptides from the PrtR-PrtK protein complex listed in Table 1 can be acryloylated and polymerised either singularly or in combination. Although this method allows the polymerisation of a number of peptides together the order in which peptides are incorporated can not be controlled.

The final peptide construct may or may not contain all, sum or part of the peptides listed in Table 1. Also the construct may or may not contain promiscuous T-cell epitopes known in the art (Kaumaya et al 1994, in Solid Phase Synthesis. Ed Epton, R) or a derived sequence from structural/binding motifs of MHC class II binding peptides (O'Sullivan et al., 1991, J. Immunol, 147:2663-2669, Hammer et al., 1993, Cell, 74:197-203 and Alexander et al., 1994, Immunity, 1:751-761). Furthermore, lipid moieties such as palmitic acid or cholesterol can be included to enhance the immunogenic properties of the peptide construct. Enzymatic cleavable sequences known in the art (Duncan et al., ref) or derived sequences from cleavage motifs (Van Noort and van der Drift., ref) can also be incorporated with the peptide construct.

The synthetic peptide antigens identified in Table 1 are of particular interest for diagnostics and neutralisation by passive immunity through oral compositions containing neutralising antibodies and by vaccine development. The superiority of these synthetic peptide antigens to prior disclosed P. gingivalis antigens, is that these sequences are homologous to structurally and functionally significant areas of the major P. gingivalis virulence factor the PrtR-PrtK proteinase-adhesin complex. The peptides represent sequences associated with the active site of the proteinases and binding domains of the adhesins making them ideal for the development of diagnostic and immunoprophylactic products.

Antibodies against the antigens can be used in oral compositions such as toothpaste and mouthwash to neutralise the antigens and thus prevent disease. Antigen-specific antibodies can also be used for the early detection of P. gingivalis in subgingival plaque samples by a diagnostic assay. A vaccine based on these antigens and suitable adjuvant delivered by nasal spray, orally or by injection to produce a specific immune response against these antigens thereby reducing colonisation and virulence of P. gingivalis and thereby preventing disease. The peptide antigens of the present invention may be used as immunogens in prophylactic and/or therapeutic vaccine formulations; or as an antigen in diagnostic immunoassays directed to detection of P. gingivalis infection by measuring an increase in serum titer of P. gingivalis-specific antibody. Also the synthetic peptides of the present invention may be used to generate antigen-specific antibody which may be useful for passive immunization and as reagents for diagnostic assays directed to detecting the presence of P. gingivalis in clinical specimens such as subgingival plaque samples.

Unlike whole P. gingivalis cells or other previously prepared antigens, the synthetic peptide antigens described herein are safe and effective antigens for the preparation of a vaccine for the prevention of P. gingivalis-associated periodontal disease.

BRIEF DESCRIPTION OF THE FIGURES

FIG. 2: Synthesis of multivalent peptide constructs using bi-modal peptides. (a) Ligation. 8 M urea and 0.1 M $NaH_2PO_4$ (pH range 3-4.7). Ligation can be monitored by reverse phase analytical HPLC and mass spectrometry. (b) Deprotection, e.g. Aloc is removed by palladium(0)-catalyzed allyl group transfer to a basic receptor. The ligation product can be purified by preparative HPLC and lypholised. (c) Ligation. Similar conditions as described in (a). Different ligation chemistries can be used by synthesising peptides with different ligands and synthesising non-complementary ligands on to the same peptide, thereby avoiding protected ligands. The square symbol indicates protection, (L) ligand, (P) peptide.

FIG. 3: Synthesis of multivalent peptide constructs using bi-modal peptides by solid phase. (a) Deprotection and ligation. The S-acetyl protecting group is removed by aqueous hydroxyamine 0.05 M, pH 7.3. After washing the first peptide can be ligated on to the SH group, 6 M aqueous guanidine hydrochloride and 0.05 M EDTA pH 6.4-6.5 adjusted by 1 M Tris.HCl under nitrogen. Ligation buffer can contain organic solvents such as acetonitrile. (b) Deprotection, the S-acetyl protecting group can be removed by aqueous hydroxyamine 0.05 M, pH 7.3. (c) Ligation, as described in (a) although different ligation chemistries can be used by synthesising peptides with different ligands and synthesising non-complementary ligands on to the same peptide, thereby avoiding protected ligands. The square symbol indicates protection, (L) ligand, (P) peptide, (B) base labile handle. 4-hydroxymethyl benzoic acid.

FIG. 4 (SEQ ID NOS:1 and 3): Cyclization using bi-modal peptides. (a) Deprotection and cyclisation. Synthesis of bi-modal peptides which have complimentary ligands at their N- and C-termini allows the cyclisation of these peptides in aqueous buffers. (i) Ligation. (ii) Deprotection and ligaction. (iii) Cleavage of the cyclic peptide from the base labile handle. Example: The peptides shown are from Table 1 and present the active site peptides from prtR 45. (a) Ligation. 95% aqueous TFA. Ligation can be monitored by reverse phase analytical HPLC and mass spectrometry. Ligation conditions can be varied to included scavengers commonly used in peptide synthesis and different acidic conditions to enhance the Friedal-Craft alkylation. (b) Deprotection and ligation. The S-acetyl protecting group can be removed by aqueous hydroxyamine 0.05 M, pH 7.3. Ligation, 6 M aqueous guanidine hydrochloride and 0.05 M EDTA pH 6.4-6.5 adjusted by 1 M Tris.HCl under nitrogen. The ligation strategy can also be accomplished on the solid phase. By selecting which ligand to introduce at the N- and C-terminal parallel and anti-parallel cyclic peptides can be synthesised.

FIG. 5 (SEQ ID NOS:35 and 50): Synthesis of multivalent multiple antigenic peptides (MAPs) using alternate ligation chemistries. By using different ligation strategies a variety of peptides can be ligated onto a single multiple antigenic peptide. The example shown is of peptides listed in Table 1. (a) Ligation, 95% aqueous TFA. Ligation can be monitored by reverse phase analytical HPLC and mass spectrometry. Deprotection, Aloc can removed by palladium(0)-catalyzed allyl group transfer to a basic receptor after purification the second peptide can be ligated on to the MAP, (c) 8 M urea and 0.1 M $NaH_2PO_4$ (pH range 3-4.7).

FIG. 8 (SEQ ID NOS:99 and 101) An alignment of the deduced amino acid sequences of PrtRII50, PrtR45 Arg-specific proteinase and PrtK48 Lys-specific proteinase with optimised similarity. The amino acyl residues of PrtRII50 are numbered from the N-terminal residue of the mature protein. * indicates an identical residue to that in PrtRII50. The underlined residues indicate the putative adhesin-binding motif. The putative cataltic His and Cys residues are boxed.

FIG. 9 Schematic representation of the prtRII, prtR and prtK genes. The PrtR nascent polyprotein consists of a leader sequence and profragment followed by the PrtR45 Arg-specific proteinase and the PrtR44, PrtR15, PrtR17 and PrtR27 adhesin domains. The PrtK nascent polyprotein similarly consists of a leader sequence, a profragment, the PrtK48 Lys-specific proteinase and the PrtK39, PrtK15 and PrtK44 adhesin domains. The PrtRII nascent polyprotein consists no associated adhesins and consists of a leader sequence, a profragment and the PrtRII50 Arg-specific proteinase only. B indicates the relative positions of the putative adhesing-binding motifs. H and C represent the location of the putative catalytic His, Cys dyad of the proteinases.

Figure 1:
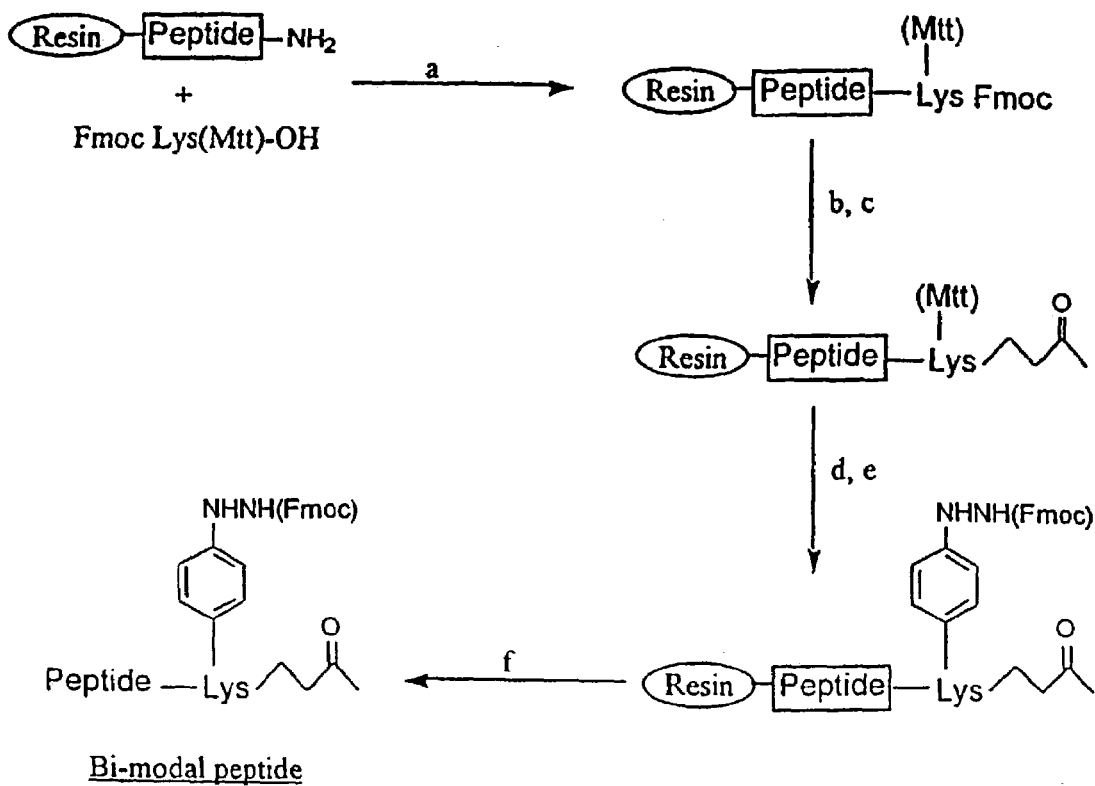
FIG. 1: Synthesis of Bi-modal Peptides Although a specific example is shown here any ligand can be introduced at the a or e amino groups of lysine. (a) acylation e.g. amino acid:HOBt:HBTU:DIPEA 1:1:1:1.5 in dimethyl formamide (DMF). (b) Fmoc deprotection e.g. 20% piperidine in DMF. (c) Levulinic acid: diisopropyl carbodiimide (DIC) 2:1 in dichloromethane (DCM). 1 h. (d) Mtt removal, 3×1% TFA in DCM. 3 mins. (e) Fmoc-Hydrazino benzoic acid : DIC 2:1, in DCM, 1 h. (f) Acid cleavage e.g. TFA:water 95:5.

ABM1(R45)-DT, (□); ABM2(K39)-KT, (○); ABM3(R44)-DT, (✱);

ABM4(R17)-DT, (●): ABM5(R15)-DT, (◆); ABM6(K39)-DT, (◇)

PAS1(R45)-DT, (▲); PAS1(K48)-DT, (■); Control peptide-DT, (-◇-);

formalin killed *P. gingivalis* strain 33277, (+); DT, (- -Δ- - ); adjuvant, (X). For clarity error bars are not shown.

DETAILED DESCRIPTION OF THE INVENTION

This invention relates to an oral composition and an immunogenic composition for the suppression of the pathogenic effects of the intra-oral bacterium *Porphyromonas gingivalis* associated with periodontal disease. It also relates to diagnostic tests for the presence of *Porphyromonas gingivalis* in subgingival plaque samples and specific anti-*P. gingivalis* antibodies in sera. The peptide antigens of Table 1 can be synthesized individually or as multimetric or multipeptide constructs.

The synthetic peptide antigens are used to generate polyclonal or monoclonal antibodies using standard techniques. The animals used for antibody generation can be mice, rabbits, goats, chickens, sheep, horses, cows etc. When a high antibody titre against the antigens is detected by immunoassay the animals are bled or eggs or milk are collected and the serum prepared and/or antibody purified using standard techniques or monoclonal antibodies produced by fusing spleen cells with myeloma cells using standard techniques. The antibody (immunoglobulin fraction) may be separated from the culture or ascites fluid, serum, milk or egg by salting out, gel filtration, ion exchange and/or affinity chromatography, and the like, with salting out being preferred. In the salting out method the antiserum or the milk is saturated with ammonium sulphate to produce a precipitate, followed by dialyzing the precipitate against physiological saline to obtain the purified immunoglobulin fraction with the specific antibody. The preferred antibody is obtained from the equine antiserum and the bovine antiserum and milk. In this invention the antibody contained in the antiserum and milk obtained by immunising the animal with the antigens is blended into the oral composition. In this case the antiserum and milk as well as the antibody separated and purified from the antiserum and milk may be used. Each of these materials may be used alone or in combination of two or more. Antibodies can be used in oral compositions such as toothpaste and mouthwash to neutralise *P. gingivalis* and thus prevent disease. The antibodies can also be used for the early detection of *P. gingivalis* in subgingival plaque samples by a chairside Enzyme Linked Immunosorbent Assay (ELISA).

For oral compositions it is preferred that the amount of the above antibodies administered is 0.0001-50 g/kg/day and that the content of the above antibodies is 0.0002-10% by weight preferably 0.002-5% by weight of the composition. The oral composition of this invention which contains the above-mentioned serum or milk antibody may be prepared and used in various forms applicable to the mouth such as dentifrice including toothpastes, toothpowders and liquid dentifrices, mouthwashes, troches, chewing gums, dental pastes, gingival massage creams, gargle tablets, dairy products and other foodstuffs. The oral composition according to this invention may further include additional well known ingredients depending on the type and form of a particular oral composition.

In certain highly preferred forms of the invention the oral composition may be substantially liquid in character, such as a mouthwash or rinse. In such a preparation the vehicle is typically a water-alcohol mixture desirably including a humectant as described below. Generally, the weight ratio of water to alcohol is in the range of from about 1:1 to about 20:1. The total amount of water-alcohol mixture in this type of preparation is typically in the range of from about 70 to about 99.9% by weight of the preparation. The alcohol is typically ethanol or isopropanol. Ethanol is preferred.

The pH of such liquid and other preparations of the invention is generally in the range of from about 4.5 to about 9 and typically from about 5.5 to 8. The pH is preferably in the range of from about 6 to about 8.0, preferably 7.4. The pH can be controlled with acid (e.g. citric acid or benzoic acid) or base (e.g. sodium hydroxide) or buffered (as with sodium citrate, benzoate, carbonate, or bicarbonate, disodium hydrogen phosphate, sodium dihydrogen phosphate, etc).

Other desirable forms of this invention, the oral composition may be substantially solid or pasty in character, such as toothpowder, a dental tablet or a dentifrice, that is a toothpaste (dental cream) or gel dentifrice. The vehicle of such solid or pasty oral preparations generally contains dentally acceptable polishing material. Examples of polishing materials are water-insoluable sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, hydrated alumina, calcined alumina, aluminum silicate, zirconium silicate, silica, bentonite, and mixtures thereof. Other suitable polishing material include the particulate thermosetting resins such as melamine-, phenolic, and urea-formaldehydes, and cross-linked polyepoxides and polyesters. Preferred polishing materials include crystalline silica having particle sized of up to about 5 microns, a mean particle size of up to about 1.1 microns, and a surface area of up to about 50,000 cm$^2$/gm., silica gel or colloidal silica, and complex amorphous alkali metal aluminosilicate.

When visually clear gels are employed, a polishing agent of colloidal silica, such as those sold under the trademark SYLOID as Syloid 72 and Syloid 74 or under the trademark SANTOCEL as Santocel 100, alkali metal alumino-silicate complexes are particularly useful since they have refractive indices close to the refractive indices of gelling agent-liquid (including water and/or humectant) systems commonly used in dentifrices.

Many of the so-called "water insoluble" polishing materials are anionic in character and also include small amounts of soluble material. Thus, insoluble sodium metaphosphate may be formed in any suitable manner as illustrated by Thorpe's Dictionary of Applied Chemistry, Volume 9. 4th Edition. pp. 510-511. The forms of insoluble sodium metaphosphate known as Madrell's salt and Kurrol's salt are further examples of suitable materials. These metaphosphate salts exhibit only a minute solubility in water, and therefore are commonly referred to as insoluble metaphosphates (IMP). There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced or eliminated by washing with water if desired. The insoluble alkali metal metaphosphate is typically employed in powder form of a particle size such that no more than 1% of the material is larger than 37 microns.

The polishing material is generally present in the solid or pasty compositions in weight concentrations of about 10% to about 99%. Preferably, it is present in amounts from about 10% to about 75% in toothpaste, and from about 70% to about 99% in toothpowder. In toothpastes, when the polishing material is silicious in nature, it is generally present in amount of about 10-30% by weight. Other polishing materials are typically present in amount of about 30-75% by weight.

In a toothpaste, the liquid vehicle may comprise water and humectant typically in an amount ranging from about 10% to about 80% by weight of the preparation. Glycerine, propylene glycol, sorbitol and polypropylene glycol exemplify suitable humectant/carriers. Also advantageous are liquid mixtures of water, glycerine and sorbitol. In clear gels where the refractive index is an important consideration, about 2.5-30% w/w of water, 0 to about 70% w/w of glycerine and about 20-80% w/w of sorbitol are preferably employed.

Toothpaste, creams and gels typically contain a natural or synthetic thickener or gelling agent in proportions of about 0.1 to about 10, preferably about 0.5 to about 5% w/w. A suitable thickener is synthetic hectorite, a synthetic colloidal magnesium alkali metal silicate complex clay available for example as Laponite (e.g. CP, SP 2002, D) marketed by Laporte Industries Limited. Laponite D is, approximately by weight 58.00% $SiO_2$, 25.40% MgO, 3.05% $Na_2O$, 0.98% $Li_2O$, and some water and trace metals. Its true specific gravity is 2.53 and it has an apparent bulk density of 1.0 g/ml at 8% moisture.

Other suitable thickeners include Irish moss, iota carrageenan, gum tragacanth, starch, polyvinylpyrrolidone, hydroxyethylpropylcellulose, hydroxybutyl methyl cellulose, hydroxypropyl methyl cellulose, hydroxyethyl cellulose (e.g. available as Natrosol), sodium carboxymethyl cellulose, and colloidal silica such as finely ground Syloid (e.g. 244). Solubilizing agents may also be included such as humectant polyols such propylene glycol, dipropylene glycol and hexylene glycol, cellosolves such as methyl cellosolve and ethyl cellosolve, vegetable oils and waxes containing at least about 12 carbons in a straight chain such as olive oil, castor oil and petrolatum and esters such as amyl acetate, ethyl acetate and benzyl benzoate.

It will be understood that, as is conventional, the oral preparations are to be sold or otherwise distributed in suitable labelled packages. Thus, a jar of mouthrinse will have a label describing it, in substance, as a mouthrinse or mouthwash and having directions for its use: and a toothpaste, cream or gel will usually be in a collapsible tube, typically aluminium, lined lead or plastic, or other squeeze, pump or pressurized dispenser for metering out the contents, having a label describing it, in substance, as a toothpaste, gel or dental cream.

Organic surface-active agents are used in the compositions of the present invention to achieve increased prophylactic action, assist in achieving thorough and complete dispersion of the active agent throughout the oral cavity, and render the instant compositions more cosmetically acceptable. The organic surface-active material is preferably anionic, nonionic or ampholytic in nature which does not denature the antibody of the invention, and it is preferred to employ as the surface-active agent a detersive material which imparts to the composition detersive and foaming properties while not denaturing the antibody. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkylsulfo-acetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. The use of these sarconite compounds in the oral compositions of the present invention is particularly advantageous since these materials exhibit a prolonged marked effect in the inhibition of acid formation in the oral cavity due to carbohydrates breakdown in addition to exerting some reduction in the solubility of tooth enamel in acid solutions. Examples of water-soluble nonionic surfactants suitable for use with antibodies are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides, polyhydric alcohols (e.g. sorbitan monostearate) and polypropyleneoxide (e.g. Pluronic materials).

Surface active agent is typically present in amount of about 0.1-5% by weight. It is noteworthy, that the surface active agent may assist in the dissolving of the antibody of the invention and thereby diminish the amount of solubilizing humectant needed.

Various other materials may be incorporated in the oral preparations of this invention such as whitening agents, preservatives, silicones, chlorophyll compounds and/or ammoniated material such as urea, diammonium phosphate, and mixtures thereof. These adjuvants, where present, are incorporated in the preparations in amounts which do not substantially adversely affect the properties and characteristics desired.

Any suitable flavoring or sweetening material may also be employed. Examples of suitable flavoring constituents are flavoring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, xylitol, sodium cyclamate, perillartine, AMP (aspartyl phenyl alanine, methyl ester), saccharine, and the like. Suitably, flavor and sweetening agents may each or together comprise from about 0.1% to 5% more of the preparation.

In the preferred practice of this invention an oral composition according to this invention such as mouthwash or dentifrice containing the composition of the present invention is preferably applied regularly to the gums and teeth, such as every day or every second or third day or preferably from 1 to 3 times daily, at a pH of about 4.5 to about 9, generally about 5.5 to about 8, preferably about 6 to 8, for at least 2 weeks up to 8 weeks or more up to a lifetime.

The compositions of this invention can be incorporated in lozenges, or in chewing gum or other products, e.g. by stirring into a warm gum base or coating the outer surface of a gum base, illustrative of which may be mentioned jelutong, rubber latex, vinylite resins, etc., desirably with conventional plasticizers or softeners, sugar or other sweeteners or such as glucose, sorbitol and the like.

Another important form of the invention is a immunogenic composition based on the synthetic peptide antigens and suitable adjuvant delivered by nasal spray, orally or by injection to produce a specific immune response against the antigen thereby reducing colonisation of *P. gingivalis* and reducing virulence thereby preventing disease. Unlike whole *P. gingivalis* cells or other previously prepared antigens, the peptide antigens described herein are safe and effective antigens for the preparation of a vaccine for the prevention of *P. gingivalis*-associated periodontal disease. Additionally, according to the present invention, antigenic peptide produced may be used to generate *P. gingivalis* antisera useful for passive immunization against periodontal disease and infections caused by *P. gingivalis*.

The following examples are further illustrative of the nature of the present invention, but it is understood that the invention is not limited thereto. All amounts and proportions referred to herein and in the appended claims are by weight unless otherwise indicated.

EXAMPLE 1

The identification of the proteinase active site and adhesin binding motifs was facilitated by the cloning and characterisation of the second gene encoding an Arg-specific proteinase of *P. gingivalis* W50.

Materials

O-Benzotriazole-N,N,N',N'-tetramethyluronium hexafluorophosphate (HBTU), 1hydroxybenzotriazole (HOBt), diisopropylethylamine (DIPEA), N,N-dimethylformamide (DMF), piperidine, trifluoroacetic acid (TFA) and 9-fluorenylmethoxycarbonyl (Fmoc)-protected amino acids were obtained from Auspep Pty Ltd (Melbourne, Australia). Triisopropylsilane (TIPS) and ethanedithiol (EDT) were obtained from Aldrich (New South Wales, Australia). 1,8-diazabicyclo[5.4.0]undec-7-ene (DBU) was obtained from Sigma Chemical Company (New South Wales, Australia). Phenol and diethyl ether were obtained from BDH (Poole, UK). Unless otherwise stated chemicals were of peptide synthesis grade or its equivalent.

Bacterial Strain and Growth Conditions

Lyophilized cultures of *Porphyromonas gingivalis* W50 were kindly provided by Professor P. Marsh (PHLS, Centre for Applied Microbiology and Research, Wiltshire, UK). *P. gingivalis* W50 was grown anaerobically (Bhogal et al., 1997) and *Escherichia coli* JM109 and LE392 strains were grown following the procedures previously described (Slakeski et al., 1996).

Purification of the 50 kDa Arg-Specific Proteinase

*P. gingivalis* W50 was grown in batch culture (5 L) and harvested at late logarithmic phase by centrifugation (5,000×g, 20 min, 4° C.). Cells were washed once with 150 ml TC buffer (20 mM Tris-HCl pH 7.4 and 5 mM $CaCl_2$) containing 50 mM NaCl and sonicated as described previously (Bhogal et al., 1997). The sonicate was centrifuged (100,000×g, 30 min, 4° C.) and the supernatant filtered (0.22

µm) prior to anion-exchange FPLC. The sonicate was applied to an anion-exchange column (Hiload XK 16/10 Q Sepharose, Pharmacia-LKB) cooled to 4° C., in multiple injections using a 50 ml superloop (Pharmacia-LKB). The sonicate was eluted using a linear gradient from 0-100% buffer B over 90 min at a flow rate of 2.0 ml min$^{-1}$. Absorbance was monitored at 280 nm and elutant collected at 4° C. in 6 ml fractions using a Frac 100 fraction collector (Pharmacia-LKB). Buffer A was TC buffer containing 50 mM NaCl and buffer B was TC buffer containing 500 mM NaCl. Fractions were analysed for proteolytic and amidolytic activity using azocasein (A-2765, Sigma Chemical Co. St Louis, Mo.), benzoyl-L-Arg-p-nitroanilide (Bz-L-Arg-pNA, Sigma) and benzyloxycarbonyl-L-Lys-p-nitroanilide (z-L-Lys-pNA, Calbiochem, Melbourne, Australia) as described previously (Bhogal et al., 1997) except that fractions were pre-incubated with 10 mM cysteine for 10 min at 25° C. before the addition of substrate. For the amidolytic assays absorbance was monitored at 410 nm as previously described (Bhogal et al., 1997) and the amidolytic activity expressed as U where U=µmol substrate converted min$^{-1}$ at 25° C. Anion-exchange fractions eluting between 160-246 mM NaCl containing the highest ratio of Arg-specific to Lys-specific activity were, washed and concentrated in TC buffer containing 150 mM NaCl using a centripep and centricon 10 concentrators (Amicon) and applied to a gel filtration column (Superose 12, HR 10/30, Pharmacia-LKB) using TC buffer containing 150 mM NaCl at a flow rate of 0.3 ml min$^{-1}$. Absorbance was monitored at 280 nm and fractions collected at 4° C. using a Frac 100 fraction collector. The $M_r$ values of eluant peaks were determined using gel filtration molecular mass standards (Pharmacia-LKB). The peak eluting at 50 kDa containing only Arg-specific amidolytic activity was washed in TC buffer containing 50 mM NaCl using a centricon-10 concentrator (Amicon) and applied to a Mono Q (HR 5/5) anion-exchange column using a 5 ml loop and eluted using a linear gradient of 0-100% buffer B at a flow rate 1.0 ml min$^{-1}$. Buffer A was TC buffer containing 150 mM NaCl, buffer B was TC buffer containing 500 mM NaCl. Absorbance was monitored at 280 nm and fractions collected at 4° C. using a Frac 100 fraction collector.

SDS-PAGE, Protein Transblot and N-terminal Sequence Analysis

SDS-PAGE was performed using a Mini protean II electrophoresis system (Biorad) with 12% (w/v), 1 mm separating gels, overlaid with 5% stacking gels (Laemmli, 1970) and proteins transblotted and N-terminally sequenced using the procedures previously described (Bhogal et al., 1997).

Cloning and Nucleotide Sequence Analysis

The *P. gingivalis* W50 LambdaGEM®-12 genomic library, described previously (Slakeski et al., 1996) was screened using synthetic oligonucleotides derived from the nucleotide sequence of prtR (Slakeski et al., 1996) corresponding to the N-terminal sequence of PrtR45. Oligonucleotide probes were 5' end-labelled using γ$^{32}$P ATP and T4 polynucleotide kinase. Approximately 1.5×10$^4$ phage were screened by lifting onto Nylon membrane filters and hybridising with radiolabelled oligonucleotides overnight in hybridisation buffer: 6×SSC (SSC is 15 mM sodium citrate, 150 mM NaCl pH 8.0), 0.25% SDS, 5× Denhardt's solution (Sambrook et al., 1989) and 100 µg/ml salmon sperm DNA at 49° C. Filters were washed extensively in a solution of 2×SSC containing 0.1% SDS (w/v) at 49° C. Phage from positively-hybridising plaques were purified using standard procedures (Sambrook et al., 1989). Phage DNA was digested with Eco72 I and the resulting fragments ligated into Sma I-BAP pUC18 (Pharmacia, Sydney, Australia) which was used to transform *E. coli* JM109 using the heat shock procedure (Sambrook et al., 1989). Double-stranded template DNA was sequenced as described previously (Slakeski et al., 1996).

PCR was used to amplify a 991 bp fragment containing the internal Eco 72I site encoded by prtRII using the two oligonucleotide primers 5'-CGGCTTCCGTAAAGTC-3' (SEQ ID NO:87) (forward primer identical to bases 657-672 of PrtRII sequence) and 5'-TGGCTACGATGACGATCAT-ACGAC-3', (SEQ ID NO:88) (reverse primer with 96% identity to bases 1624-1647 of PrtRII). The PCR was carried out in a final volume of 100 µl and each reaction mixture contained 100 ng *P. ginigivalis* W50 genomic DNA, 0.2 mM dNTPs, 1.5 mM MgCl$_2$, 100 pmol of each primer, 20 mM Tris-HCl, pH 8.4, 50 mM KCl and 2.5 U Taq DNA Polymerase (Gibco BRL). The reaction mixture was heated at 95° C. for 3 min and then subject to 25 cycles of DNA denaturation at 95° C. for 30 s, primer annealing at 40° C. for 1 min and extension at 72° C. for 2 min. Following cycling, the reaction mixture was finally heated at 72° C. for 5 min. Amplified DNA was purified using a PCR Spinclean Kit (Progen) and sequenced across the Eco 72I site in both directions.

Purification of High Molecular Mass Complexes of Arg-Specific and Lys-Specific Proteinases and Adhesins (PrtR-PrtK Complexes)

The high molecular mass, cell-associated proteinase-adhesin complexes (PrtR-PrtK complexes) of *P. gingivalis* W50 were purified using a combination of anion-exchange, gel filtration and Arg-sepharose affinity chromatography from a cell sonicate as described previously (Bhogal et al., 1997). The complexes were characterised using SDS-PAGE, transblotting and sequence analysis and assayed for enzymic activity using Bz-L-Arg-pNA and Z-L-Lys-pNA substrates (Bhogal et al., 1997).

Solid-phase Peptide Synthesis

Peptides were synthesised manually using standard Fmoc solid-phase peptide synthesis protocols. The peptides were assembled as the carboxyamide form using Fmoc-Pal-Peg-PS resin (PerSeptive Biosystems Inc. Framingham, Mass.). Coupling was accomplished with HBTU/HOBt activation using 4 equiv of Fmoc-amino acid and 6 equiv of DIPEA. The Fmoc group was removed by 2% v/v DBU in DMF containing 2% v/v piperidine. Cleavage of peptides from the resin support was performed using TFA:phenol:TIPS:EDT: water (92:2:2:2:2) cleavage cocktail for 2.5 hours. After cleavage the resin was removed by filtration and the filtrate concentrated to approximately 1 ml under a stream of nitrogen. After the peptide products were precipitated in cold ether, they were centrifuged and washed three times. The peptide precipitate was then dissolved in 10 ml of water containing 0.1% v/v TFA and insoluble residue removed by centrifugation.

Purification of synthesized peptides was performed using a Brownlee C18 Aquapore ODS column (250×100 mm) installed in a Waters HPLC system. Chromatograms were developed at a flow rate of 5.0 ml min$^{-1}$ using 0.1% v/v TFA in water (solvent A) and 0.1% v/v TFA in 90% aqueous acetonitrile (solvent B). Peptides were eluted with a gradient of 10-30% solvent B over 40 min. Analytical HPLC was carried out using a Brownlee C8 Aquapore RP-300 column (220×4.6 mm) installed in a Applied Biosytems HPLC system. Chromatograms were developed using solvent A and solvent B at a flow rate of 1.0 ml min$^{-1}$ and a 0-100% linear gradient of solvent B over 30 min. Material eluted from the columns was monitored by absorbance at 214 nm. Peptides were analysed by mass spectrometry using a PerSeptive Biosystems Voyager DE MALDI-TOF.

Competitive Binding Assay

Wells of flat-bottomed polyvinyl microtitre plates (Microtitre, Dynatech Laboratories, Va.) were coated overnight at 4° C. using a solution (5 mg/ml) of the adhesin binding motif (ABM) peptide in 0.1M phosphate buffered saline, pH 7.4, containing 0.1% v/v Tween 20 (PBST) and 0.1% w/v sodium azide. After removal of the coating solution, 2% w/v skim milk powder in PBST was added to block the remaining uncoated plastic for 1 hour at room temperature and then washed (4×PBST). A solution (1 mg/ml) of the PrtR-PrtK proteinase-adhesion complex (inactivated with 1 mM TLCK) was incubated with known concentrations of ABM peptide, control peptide and casein for 1 hour and then transferred to the microtitre plates coated with the ABM peptide. Following incubation for 2 hours at 37° C. the plates were washed (5×PBST). A 1/10,000 dilution of rabbit anti-PrtR-PrtK antisera in PBST containing 1% w/v skim milk powder was then added to the washed wells and incubated for 2 hours at 37° C. Bound antibody was detected by incubation with horseradish peroxidase-conjugated goat immunoglobulin (Ig) directed against rabbit Ig (BioRad, Richmond, Calif.) for 1.5 hours at 37° C. After washing (5×PBST), substrate (0.4 mM 3,3',5,5'-tetramethylbenzidine in 0.1M sodium acetate/citric acid buffer containing 0.004% v/v hydrogen peroxide) was added and colour development was stopped by addition of 2M $H_2SO_4$. Optical density (O.D.) at 450 nm was measured using a BioRad microplate reader model 450.

Results

PrtRII50 Arg-Specific Proteinase Purification and Characterisation

Figure 6:
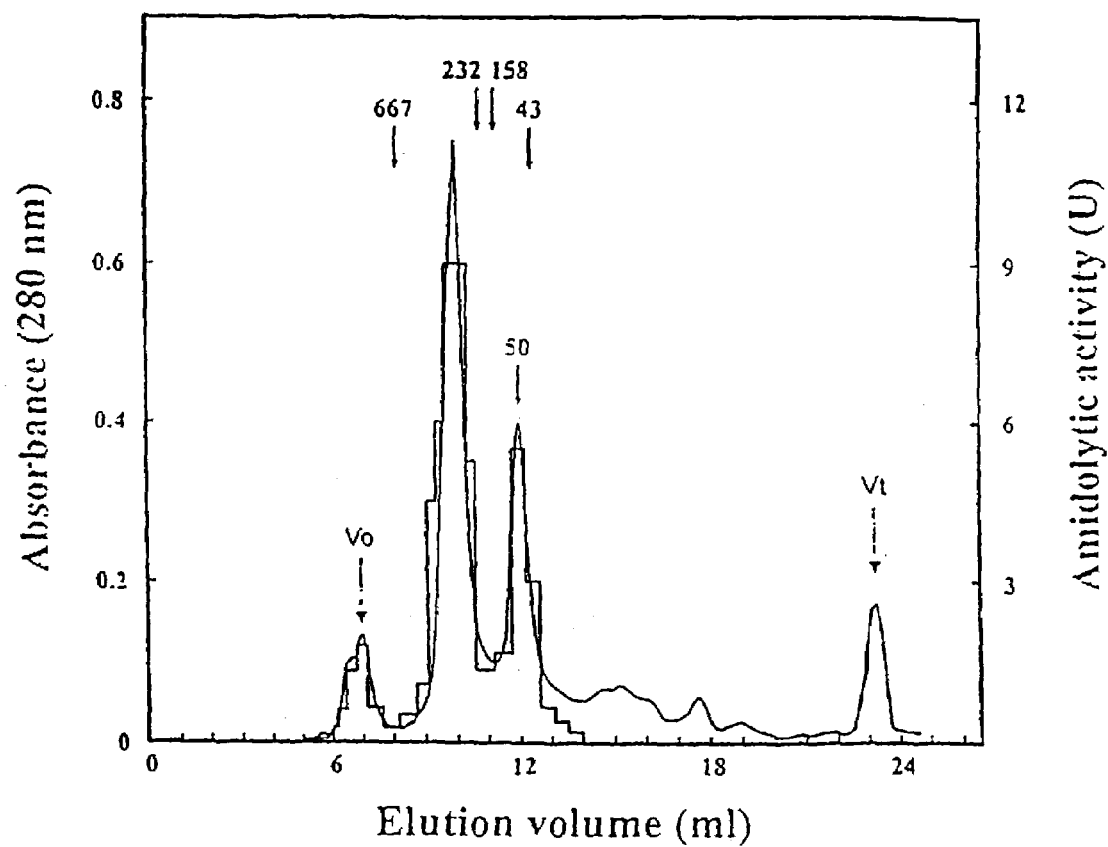
FIG. 6 Gel Filtration FPLC of pooled and concentrated fractions eluting from Q sepharose anion exchange FPLC. Anion exchange fractions eluting between 160-246 mM NaCl and representing the leading edge of the main peak of proteolytic/amidolytic activity were pooled, equilibrated in TC buffer pH 7.4 containing 50 mM NaCl, concentrated and applied to Superose 12 HR 10/30 gel filtration column using the same buffer at a flow rate of 0.3 ml $min^{-1}$. Fractions (0.5 ml) were assayed for proteolytic/amidolytic activity using azocasein, Bz-L-Arg-pNA and z-L-Lys-pNA. Amidolytic activity of each 0.5 ml fraction with BZ-L-pNA is shown by the histogram.
Figure 7:
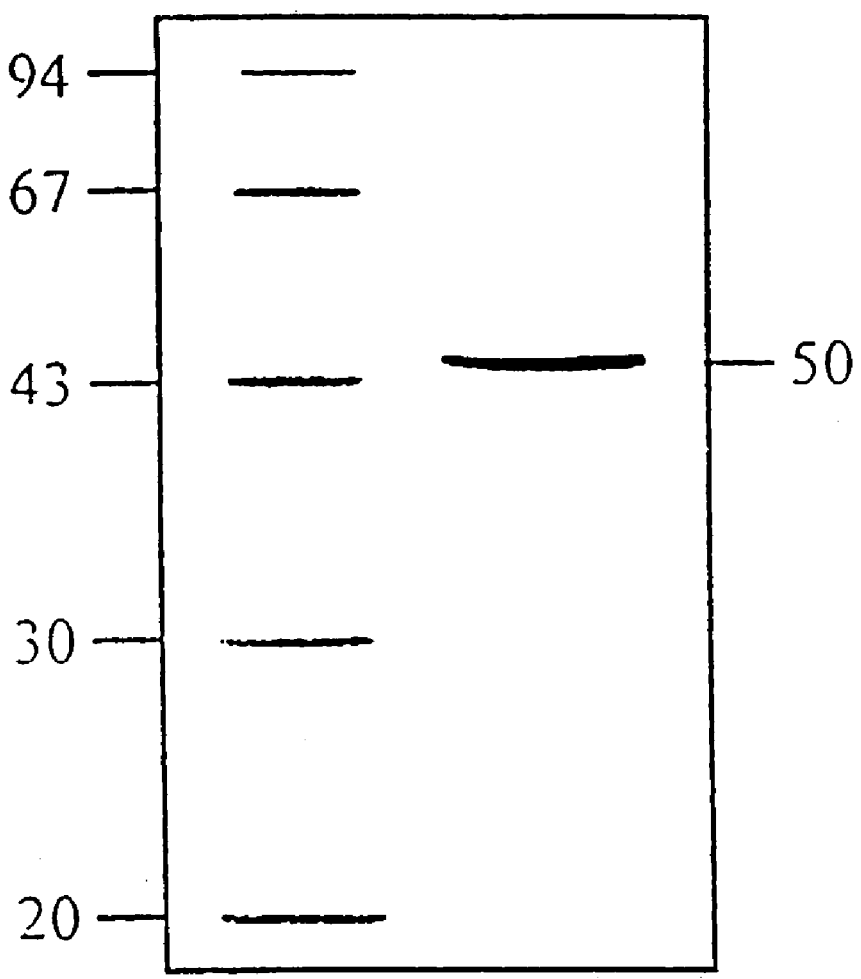
FIG. 7 SDS-PAGE (bolied/reduced conditions) of the anion exchange (Mono Q) peak eluting at 200 mM NaCl and containing only Arg-specific activity. Lane 1, Pharmacia low molecular mass standards; lane 2, Purified 50 kDa Arg-specific proteinase, PrtRII50.

The *P. gingivalis* W50 cell sonicate contained 0.36 mg $ml^{-1}$ protein and 2.4 and 1.1 μmol $min^{-1}$ mg $protein^{-1}$ activity with 1.0 mM Bz-L-Arg-pNA and z-L-Lys-pNA as substrates respectively at 25° C. The sonicate was subjected to Q-sepharose anion exchange FPLC and proteolytic/amidolytic activity eluting between 160-246 mM NaCl was collected and concentrated using a centripep and centricon-10 concentrator (Amicon, Sydney, Australia). This fraction represented the leading edge of the main peak of proteolytic/amidolytic activity and contained the highest ratio of Arg-specific activity to Lys-specific activity. After concentration, the fraction was applied to a Superose 12 gel filtration column (FIG. 6). Arg- and Lys-specific activity was associated with the high molecular mass eluting material corresponding to peaks with $M_r$ values of 0.6-2.0×$10^6$ Da and 300 kDa as reported previously (Bhogal et al., 1997). However, a lower molecular mass peak of 50 kDa was also observed, which displayed only Arg-specific activity and this peak was collected for further purification. The 50 kDa gel filtration peak was applied to a Mono Q anion exchange column and upon application of a NaCl gradient the Arg-specific activity eluted in a distinct peak at a NaCl concentration of 200 mM NaCl with a 28-fold purification over the original crude sonicate. The peak containing Arg-specific activity was subjected to SDS-PAGE which confirmed a single 50 kDa protein band (FIG. 7). The 50 kDa band was transblotted and subjected to N-terminal sequence analysis which provided the amino acyl sequence YTPVEEKENGRMIVIVPKKYEEDIED (SEQ ID NO:89). The specificity of the 50 kDa proteinase for arginyl residues was confirmed by the enzyme cleaving Bz-L-Arg-pNA but not z-L-Lys-pNA. The Arg-specific 50 kDa enzyme was activated by thiols (particularly cysteine), not inhibited by the serine proteinase inhibitors, phenylmethyl sulfonyl fluoride or 4-(2-aminoethyl)-benzenesulfonyl fluoride but inhibited by sulphydryl-directed reagents, leupeptin and EDTA at similar concentrations to that which inhibited the PrtR45 (Bhogal et al., 1997). Inhibition with EDTA could be reversed by the addition of excess $Ca^{2+}$ and the pH optimum of the enzyme was 8.0 with minimal activity below pH 6.0.

Molecular Cloning and Sequence Analysis of the prtRII Gene

Screening of the *P. gingivilis* genomic library using oligonucleotide probes specific for the N-terminus of PrtR45 identified several positive clones. The DNA from these clones was extracted and subjected to Southern analysis to identify those containing the 12 kb BamH I fragment previously proposed to correspond to the gene encoding the second Arg-specific proteinase (Slakeski et al., 1996). Lambda clone 18, containing a 12 kb BamH I fragment was chosen for further analysis and DNA was isolated from this clone and digested with Eco72 I and randomly cloned into plasmid Sma I-BAP pUC 18. Adjacent 3.3 and 1.2 kb Eco72 I genomic fragments were sequenced in both directions to generate the entire prtRII nucleotide sequence (Genebank Accession No. AF007124). A 991 bp PCR fragment was generated and sequenced to confirm the sequence encompassing the internal Eco72 I site.

The prtRII ORF comprises 2208 bp (736 a.a. residues) and encodes a preproprotein consisting of a putative leader sequence and a profragment followed by the mature Arg-specific proteinase (507 a.a. residues) containing the exact N-terminal amino acyl sequence obtained for the purified 50 kDa enzyme (PrtRII50). The N-terminal sequence of the mature protein, like PrtR45, is immediately preceded by an Arg residue in the profragment.

The prtRII gene exhibits a high degree of similarity with the 5' two fifths of the prtR gene which encodes PrtR45 and its associated adhesins (FIGS. 8 & 9). A comparison of the two translated sequences shows an overall similarity of 76% and 80% for the translated preprofragment and the proteinase domain, respectively. The prtRII however, does not encode any of the C-terminal haemagglutinin/adhesin domains encoded by the prtR and prtK genes being consistent with the finding that the purified PrtRII50 proteinase was not associated with adhesins. The $M_r$ of the PrtRII50 mature proteinase deduced from the translated prtRII gene sequence is 55.6 kDa which is consistent with the 50 kDa obtained by SDS-PAGE (FIG. 7) and is slightly larger than the deduced $M_r$ of 53.9 kDa for PrtR45 (Bhogal et al., 1997).

The sequence alignment of the deduced amino acyl sequence of PrtRII50 with the PrtR45 Arg-specific proteinase and the PrtK48 Lys-specific proteinase (Slakeski et al., 1996; Bhogal et al., 1997) shows that PrtRII50 displays high sequence similarity (97.5% identity) to the adhesin-associated PrtR45 proteinase except for the C-terminal 80 amino acyl residues (FIG. 8). In fact, this C-terminal 80 residue sequence of PrtRII50 is similar (47% identity) to the C-terminal 80 residues of the PrtR27 adhesin domain, the last domain of the PrtR (FIG. 9). In contrast to the high sequence identity of the PrtRII50 and PrtR45 proteinases, there is lower overall similarity (25% identity) between the two adhesin-associated PrtR45 and PrtK48 proteinases except around the C-terminal region where the motif—GEPNPYQPVSNLTATTQGQKVTLKWDAPSTK—(SEQ ID NO:5) (underlined in FIG. 8) is almost identical in both proteinases but is absent in PrtRII50. Similar motifs also occur in the PrtR44, PrtR17, PrtK39 and PrtK44 adhesin domains of PrtR and PrtK (Table 1 ABM1 peptides), which have led us to propose that this motif is an adhesin-binding motif involved in the association of the PrtR and PrtK proteinases and adhesins into large complexes.

Figure 10:
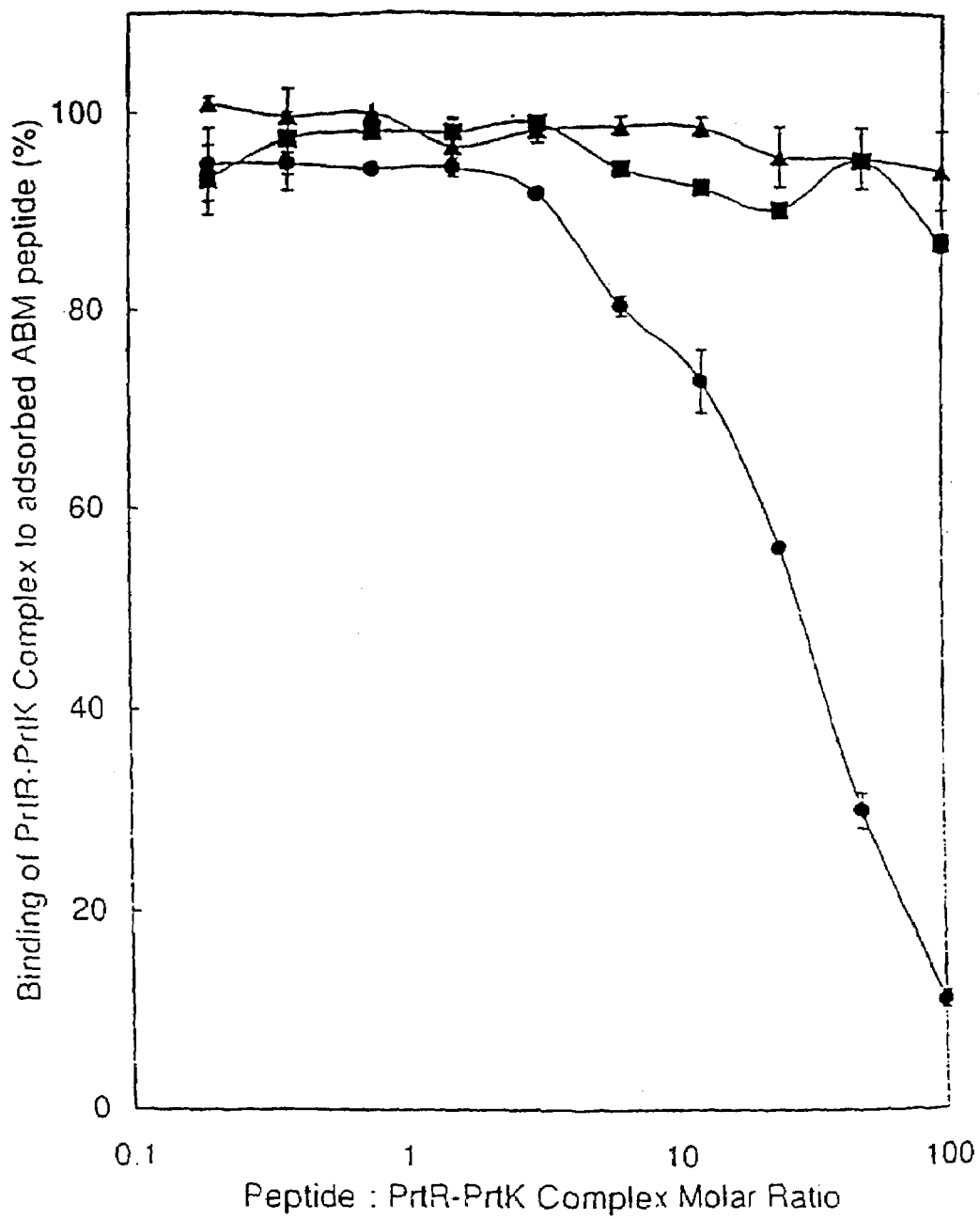
FIG. 10 Competitive Binding Assay demonstrating binding of the TLCK-inactivated PrtR-PrtK proteinase-adhesion complex to the synthetic peptide corresponding to the putative adhesin binding motif (ABM). -●-●-ABM synthetic peptide. PYQPVSNLTATTQGQKVTLKWDAPSTK(SEQ ID NO:86). -■-■-Control peptide, FNGGISLANYTGHG-SETAWGT (SEQ ID NO:1) corresponding to residues 428-448 of PrtR45. -▲-▲-casein. See Materials and Methods for details.
Figure 11:
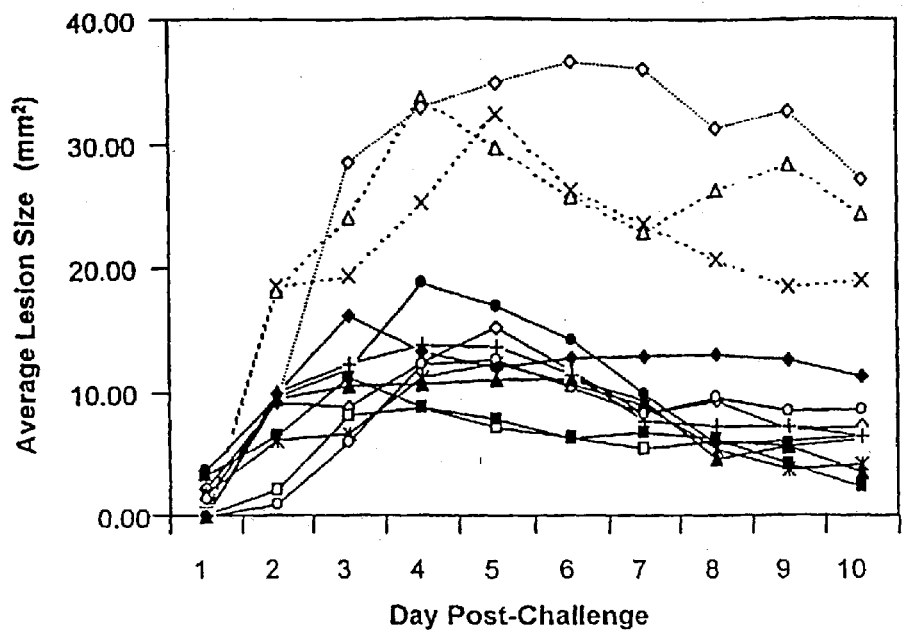
FIG. 11. Average lesion size of mice challenged with *Porphyromonas gingivalis* in a mouse abscess model. BALB/c mice (6 per group) were inoculated (s.c.) with 50 μg of antigen emulsified in CFA and IFA for the primary and secondary inoculations and then challenged (s.c.) with $8 \times 10^9$ cells of *P. gingivalis* strain 33277.

Binding of the PrtR-PrtK Complex to a Synthethic Peptide Corresponding to a Putative Adhesin Binding Motif A peptide (ABM1) corresponding to the proposed adhesin binding motif PYQPVSNLTATTQGQKVTLKWDAPSTK (SEQ ID NO:86) was synthesised and used to measure binding of the PrtR-PrtK complex. Specific binding of TLCK-inactivated PrtR-PrtK complex to the ABM peptide was demonstrated in a competitive binding assay where a 5-100 fold molar excess of the ABM peptide in solution was required to inhibit binding of the complex to the ABM peptide adsorbed onto the microtitre plate (FIG. 10). A control peptide, FNGGISLANYTGHGSETAWGT (SEQ ID NO:1) corresponding to residues 428-448 of PrtR45, as well as casein did not inhibit the binding of the TLCK-inactivated PrtR-PrtK complex to the adsorbed ABM peptide. The anti-PrtR-PrtK antisera did not bind to the ABM peptide in the absence of the PrtR-PrtK complex. The inactivation with TLCK ensured that the complex was not binding to the peptide through the active sites of the proteinases. This was also confirmed by lack of binding of the PrtR-PrtK complex to casein and a non-specific peptide of similar size and lysine content to the ABM peptide but of unrelated sequence. These results demonstrating specific binding of the TLCK-inactivated PrtR-PrtK complex to the ABM peptide therefore are consistent with the proposed role of this conserved motif in the association of the PrtR and PrtK proteinases and adhesins into large complexes.

Discussion

Using a *P. gingivalis* W50 cell sonicate we have purified and characterised a second cell-associated, Arg-specific, calcium-stabilized cysteine proteinase that is almost identical to the previously characterised Arg-specific cysteine proteinase PrtR45 (Bhogal et al., 1997). However, despite the almost identical enzymic characteristics and inhibitor/activator profile to PrtR45 the second enzyme exhibits a number of key differences. Firstly, the second enzyme designated PrtRII50, is a discrete enzyme not associated with adhesins. The Arg-specific cysteine proteinase, PrtR45, is a 45 kDa component of a large multi-protein complex of Arg- and Lys-specific proteinases and adhesins (Bhogal et al., 1997). Secondly, PrtRII50 is slightly larger than PrtR45 on SDS-PAGE ($M_r$ 50 kDa) and thirdly there are four amino acid substitutions in the first 25 N-terminal residues of PrtRII50. PrtRII50 has a Glu at position 8 instead of Gln, a Pro at position 17 instead of Ala, a Glu at position 22 instead of Gly and a Glu at position 25 instead of the Lys in PrtR45 (FIG. 8). These differences in size and the N-terminal amino acyl sequence were confirmed with the cloning and sequence analysis of the gene prtRII encoding the second Arg-specific proteinase.

The deduced amino acid sequence of the prtRII gene exhibits 98% identity with that of the recently reported rgpB gene from *P. gingivalis* ATCC 33277 (Nakayama, 1997) suggesting that both genes represent the same locus in two different strains. However, the sequence for the mature proteinase of the rgpB gene does not contain three of the N-terminal amino acyl substitutions found in the prtRII gene product and only has the Gln→Glu substitution at position 8. The substitutions at positions 17, 22 and 25 found in PrtRII50, that enabled the gene product to be unequivocally differentiated by N-terminal sequence analysis from the mature PrtR45 proteinase of the prtR (rgpA), were not found in the rgpB. In the current study the differences in N-terminal sequence and size of the mature proteinases enabled the differentiation of the discrete 50 kDa Arg-specific proteinase (PrtRII50) from the 45 kDa Arg-specific proteinase (PrtR45) found associated with adhesins. The assignment of the two proteinases (PrtR45 and PrtRII50) to the two genes (prtR and prtRII respectively) has enabled identification of a conserved motif in the two adhesin-associated proteinases (PrtR45 and PrtK48) not found in the discrete PrtRII50. As the conserved motif was also found in several adhesins of the prtR and prtK we propose that it is an adhesin binding motif involved in association of the prtR and prtK proteinases and adhesins into large complexes. This proposition is supported by the demonstration that a synthetic peptide corresponding to the conserved motif specifically binds to the TLCK-inactivated PrtR-PrtK complex.

The identification of the conserved motif PVXNLT (SEQ ID NO:90) . . . LKWXAP (SEQ ID NO:91) in the adhesin binding motif 1 led us to propose that the complementary motif would be hydrophobic and negatively charged. Repeat motifs that were therefore hydrophobic and contained negative residues were selected for synthesis. eg. TATT-FEEDGVA (SEQ ID NO:92) (ABM2, Table 1) and WKTIDADGDG (SEQ ID NO:93) (ABM5, Table 1). Other motifs selected for study were other repeated motifs of hydrophobic and/or charged and/or neutral polar residues eg. VYRDGTKIKE (SEQ ID NO: 94) (ABM2, Table 1), WEIRTVDLPAGTKYV (SEQ ID NO:95) (ABM4, Table 1) and EFAPVQNLTGSA (SEQ ID NO:96) (ABM6, Table 1).

On further examination of the alignment of the deduced amino acyl sequence of PrtRII50 with the catalytic domains of the PrtR45 Arg-specific proteinase and the PrtK48 Lys-specific proteinase some further interesting areas of similarity were revealed (FIG. 8). Although these three cysteine proteinases from *P. gingivalis* have no similarity with any of the other known families of cysteine proteinases it is possible to speculate on the identity of the catalytic residues since only one His residue and two Cys residues are conserved in the three sequence-related enzymes. The catalytic Cys, His dyad of these enzymes therefore is likely to consist of $H^{440}$ of PrtRII50, the only conserved His in the three proteinases. The catalytic Cys is also likely to be one of the two conserved cysteinyl residues $C^{473}$ and $C^{484}$ in the three sequence-related proteinases.

EXAMPLE 2

Synthesis of Proteinase Active Site and Adhesin Binding Motif Peptides and Testing in a Murine Lesion Model.

The following peptides representative of the protease active sites and each adhesin binding motif listed in Table 1 were synthesised, conjugated and tested in the murine lesion model (Table 2).

TABLE 2

Origin and amino acid sequence of synthesised peptides

| Origin | Amino acid sequence (single letter code) | Abbreviation |
| --- | --- | --- |
| Proteinase Active Site Peptides | | |
| PrtR45 (426–446) | FNGGISLANYTGHGSETAWGT (SEQ ID NO:1) | PAS1 (R45) |
| PrtK48 (432–453) | LNTGVSFANYTAHGSETAWADP (SEQ ID NO:2) | PAS1 (K48) |
| Adhesion Binding Motif Peptides | | |
| PrtR45 (664–689) | PYQPVSNLTATTQGQKVTLKWDAPSTK (SEQ ID NO:86) | ABM1 (R45) |
| PrtK39 (1580–1608) | SYTYTVYRDGTKIKEGLTATTFEEDGVAA (SEQ ID NO:20) | ABM2 (K39) |
| PrtR44 (939–971) | VTLKWDAPNGTPNPNPNPNPNPNPGTTTLSESF (SEQ ID NO:98) | ABM3 (R44) |
| PrtK44 (1296–1315) | WIERTVDLPAGTKYVAFRHY (SEQ ID NO:35) | ABM4 (K44) |
| PrtR15 (1154–1169) | PAEWTTIDADGDGQGW (SEQ ID NO:50) | ABM5 (R15) |
| PrtR44 (919–938) | EGSNEFAPVQNLTGSAVGQK (SEQ ID NO:65) | ABM6 (R44) |
| Control Peptide | | |
| PrtR27 (1432–1463) | ANEAKVVLAADNVWGDNTGYQFLLDADHNTFG (SEQ ID NO:97) | Control peptide |

Materials

Unless otherwise stated chemicals were of peptide synthesis grade or its equivalent. O-Benzotriazole-N,N,N',N'-tetramethyluronium hexafluorophosphate (HBTU), 1hydroxybenzotriazole (HOBt), diisopropylethylamine (DIPEA), N,N-dimethylformamide (DMF), piperidine, trifluoroacetic acid (TFA) and 9-fluorenylmethoxycarbonyl (Fmoc) protected amino acids were obtained from Auspep Pty Ltd (Melbourne, Australia). Triisopropylsilane (TIPS) and ethanedithiol (EDT) were obtained from Aldrich (New South Wales, Australia). 1,8-diazabicyclo[5.4.0]undec-7-ene (DBU) was obtained from Sigma Chemical Company (New South Wales, Australia). Phenol and diethyl ether were obtained from BDH (Poole, UK).

Solid-Phase Peptide Synthesis

Peptides were synthesised manually or using a 431A ABI peptide synthesiser. Standard solid-phase peptide synthesis protocols for Fmoc chemistry were used throughout. Peptides were assembled as the carboxyamide form using Fmoc-Pal-Peg-PS resin (PerSeptive Biosystems Inc., Framingham, Mass.). Coupling was accomplished with HBTU/HOBt activation using 4 equiv of Fmoc-amino acid and 6 equiv of DIPEA. The Fmoc group was removed by 2% v/v DBU in DMF containing 2% v/v piperidine. Cleavage of peptides from the resin support was performed using TFA: phenol:TIPS:EDT:water (92:2:2:2:2) cleavage cocktail for 2.5 hours or 4 hours depending on the arginine content of the peptide. After cleavage the resin was removed by filtration and the filtrate concentrated to approximately 1 mL under a stream of nitrogen. After the peptide products were precipitated in cold ether, they were centrifuged and washed three times. The peptide precipitate was then dissolved in 5 to 10 mL of water containing 0.1% v/v TFA and insoluble residue removed by centrifugation.

Synthesis of S-Acetylmercaptoacetic Acid Peptides

Resins bearing peptides were swollen in DMF and the N-terminal Fmoc group removed by 2% v/v DBU in DMF containing 2% v/v piperidine. S-Acetylmercaptoacetic acid (SAMA) group was introduced onto the N-terminal amino group using 5 equiv of SAMA-OPfp and 5 equiv of HOBt. The reaction was monitored by the trinitrobenzene sulphonic acid (TNBSA) test. When a negative TNBSA test was returned the resin was washed (5×DMF, 3×DCM and 3× diethyl ether). The resin was dried under vacuum and the SAMA-peptides cleaved from the resin support as described above.

Peptide Purification

Purification of synthesized peptides was performed using a Brownlee C18 Aquapore ODS column (250×100 mm) installed in a Waters HPLC system. Chromatograms were developed at a flow rate of 5 mL/min using 0.1% v/v TFA in water (solvent A) and 0.1% v/v TFA in 90% aqueous acetonitrile (solvent B) as the limit buffer. Peptides were eluted with a gradient of 10-30% solvent B formed over 40 min. Analytical HPLC was carried out using a Brownlee C8 Aquapore RP-300 column (220×4.6 mm) installed in a Applied Biosytems HPLC system. Chromatograms were developed using solvent A and solvent B at a flow rate of 1 mL/min and a 0-100% linear gradient of solvent B formed over 30 min. Material eluted from the columns was detected by determining the absorbance at 214 nm. Peptide fractions were pooled and lyophilised. Peptides were analysed by mass spectrometry using a PerSeptive Biosystems Voyager DE MALDI-TOF.

Conjugation of SAMA-Peptides to Diphtheria Toxoid

Diphtheria toxoid (DT) was obtained from Dr I. Barr (CSL Pty. Ltd. Melbourne, Australia) which contained 9 equivalent amino groups per 62 kDa molecule. To a solution containing 10 mg/mL of DT in phosphate-buffered saline (0.1M sodium phosphate, 0.9% NaCl; pH 7.4) was added 0.1 mL of a 1% w/v solution m-maleimido benzoyl-N-hydroxysuccinimide ester (MBS) in DMF. After 30 mins unreacted MBS was removed and NIBS modified DT collected by gel filtration using a PD10 column (Pharmacia, NSW, Australia) equilibrated in conjugation buffer (0.1M sodium phosphate, 5 mM EDTA; pH 6.0). Purified SAMA-peptide (1.3 μmole) was dissolved in 200 μL 6M guanidine HCl containing 0.5M Tris; 2 mM EDTA, pH6 and diluted with 800 μL MilliQ water and deprotected in-situ by addition of 25 μL of 2M $NH_2OH$ (40 equiv) dissolved in MilliQ water. The collected MBS-DT was immediately reacted with deprotected SAMA-peptide and stirred for one hour at room temperature. The peptide-DT conjugate was separated from unreacted peptide by gel filtration using a PD10 column equilibrated in PBS pH 7.4 and lyophilised. The reaction was monitored using the Ellmans test. The conjugation yields of SAMA-peptides to MBS-DT ranged from 34% to 45% indicating that 3 to 4 peptides were coupled per DT molecule.

Immunization and Murine Lesion Model Protocols

BALB/c mice 6-8 weeks old were immunised subcutaneously with either 50 μg of the peptide-DT conjugate. 50 μg of DT or $2 \times 10^9$ formalin killed cells of *Porphyromonas gingivalis* strain 33277 emulsified in complete Freund's adjuvant (CFA). After 30 days the mice were injected subcutaneously with antigen (either 50 μg of the peptide-DT conjugate, 50 μg of DT or $2 \times 10^9$ formalin killed cells of *Porphyromonas gingivalis* strain 33277) emulsified in incomplete Freund's adjuvant (IFA) and then bled from the retrobulbar plexus 12 days later. All mice were challenged with $8 \times 10^9$ cells of *P. gingivalis* (200 μL) by subcutaneous injection in the abdomen and weighed and lesion size measured over 10 days. Lesion sizes are expressed as $mm^2$ and were statistically analysed using a Kruskal-Wallis one-way ANOVA and Mann-Whitney U-Wilcoxon rank sum W test.

The peptide-DT conjugates were used to immunise BALB/c mice to evaluate their efficacy in protecting against *Porphyromonas gingivalis* challenge in the murine lesion model. FIG. 6 shows that mice that were immunised with the carrier protein diphtheria toxoid alone had similar average lesion sizes to the mice immunised with adjuvant alone (controls). This indicates that DT alone does not provide protection against *P. gingivalis* and moreover that any protection provided by peptide-DT conjugates was attributable to the immune response induced by the peptide. The control peptide-DT conjugate did not provide protection against *P. gingivalis* as the average lesion size was not significantly different to that of mice immunised with DT or adjuvant alone (controls). Immunisation with both the proteinase active site peptides conjugated to DT (PAS1(R45) and PAS1(K48)) Significantly reduced lesion size resulting from *P. gingivalis* challenge relative to the DT controls(Table 3). All the adhesin binding motif peptides when used as immunogens reduced lesion size however, only ABM1(R45), ABM2(K39) and ABM3(R44) attained significance ($p<0.05$) with the number of animals used (Table 3).

The results demonstrate the efficacy of the PrtR-PrtK proteinase active site peptides and adhesin binding motif peptides when used as immunogens in preventing challenge with *P. gingivalis* in the murine lesion model. These results therefore suggest that these peptides may have utility as vaccines in the prevention of *P. gingivalis* -associated disease (e.g Periodontitis) in humans.

Antisera against the PAS1 peptides inhibited both Arg- and Lys-specific proteolytic activity which therefore may explain the excellent protection conferred by immunisation with these peptides. The inhibition of proteolytic activity by the anti-PAS1 antisera suggests that these antibodies may have utility in a mouthwash, toothpaste or other intra-oral delivery vehicle to neutralise the *P. gingivalis* proteases and their damaging effects. Similarly, antisera against the adhesin binding motifs, particularly ABM1, ABM2 and ABM3 may have utility in oral care products and pharmaceuticals to block adherence and therefore colonisation of *P. gingivalis*.

TABLE 3

Maximum Lesion size and significance of peptide-diphtheria conjugates.

| | DT[d] | ABM1 (R45)-DT | AMB2 (K39)-DT | ABM3 (R44)-DT | ABM4 (K44)-DT | ABM5 (R15)-DT | ABM6 (R44)-DT | PAS1 (R45)-DT | PAS1 (K48)-DT | Control peptide-DT | FK 33277[e] |
|---|---|---|---|---|---|---|---|---|---|---|---|
| Maximum lesion size ($mm^2$) | 33.59± 18.77[a] | 10.42± 11.7 | 12.63± 10.89 | 12.27± 4.68 | 18.83± 18.87 | 14.79± 10.04 | 15.22± 11.55 | 10.46± 4.08 | 9.28± 10.36 | 36.61± 34.92 | 13.78± 12.55 |
| Significance[b] | — | $p < 0.05$ | $p < 0.05$ | $P < 0.05$ | N/S[c] | N/S[c] | N/S[c] | $P < 0.05$ | $p < 0.05$ | N/S[c] | $p < 0.05$ |

[a] = standard deviation n = 5, 6
[b] = Mann-Whitney U test.
[c] = no significant difference
[d] = Diphtheria Toxoid
[e] = formalin killed Porphyromonas gingivalis strain 33277

EXAMPLE 3

(1) Synthesis of Peptide Antigens and Multiple Constructs

The peptides of Table 1 were synthesized using standard Fmoc or tBoc synthesis strategies and multipeptide constructs were synthesized using the strategies outlined in FIGS. 1-5.

(2) Preparation of Antibodies

Serum antibodies were obtained by immunising horses, rabbits, sheep or dairy cows.

Immunizations were carried out using standard procedures. The initial immunisation was with a mixture of the antigen and Freund's incomplete adjuvant. The antibodies could be recovered from the animals serum or milk using standard procedures.

EXAMPLE 4

Methods for Using Antigenic Peptides in Diagnostic Immunoassays.

The *P. gingivalis* peptide antigens described herein can be synthesized for use as immunogens in vaccine formulations; and as antigens for diagnostic assays or for generating *P. gingivalis* -specific antisera of therapeutic and/or diagnostic value.

The peptides disclosed in Table 1 can be synthesized individually or chemically-linked using any one of a number of strategies well known in the art. Examples of some strategies which can be used are set out in FIGS. 1-5. The peptides can be synthesized using one of the several methods of peptide synthesis known in the art including standard solid phase peptide synthesis using tertbutyloxycarbonyl amino acids (Mitchell et al., 1978, *J. Org. Chem.* 43:2845-2852), using 9-fluorenylmethyloxycarbonyl amino acids on a polyamide support (Dryland et al., 1986, *J. Chem. So. Perkin Trans.* I, 125-137); by pepscan synthesis (Geysen et al., 1987, *J. Immunol. Methods* 03:259; 1984, *Proc. Natl. Acad. Sci. USA* 81:3998); or by standard liquid phase peptide synthesis. Modification of the peptides or oligopeptides, such as by deletion and substitution of amino acids (and including extensions and additions to amino acids) and in other ways, maybe made so as to not substantially detract from the inmunological properties of the peptide or oligopeptide. In particular, the amino acid sequences of the antigens described herein, may be altered by replacing one or more amino acids with functionally equivalent amino acids resulting in an alteration which is silent in terms of an observed difference in the physicochemical behaviour of the peptide, or oligopeptide or chimera. Functionally equivalent amino acids are known in the art as amino acids which are related and/or have similar polarity or charge. Thus, an amino acid sequence which is substantially that of the amino acid sequences depicted in the Sequence Listing herein, refers to an amino acid sequence that contains substitutions with functionally equivalent amino acids without changing the primary biological function of the peptide, oligopeptide or chimera.

Purified synthetic peptides may be used as antigens in immunoassays for the detection of *P. gingivalis*-specific antisera present in the body fluid of an individual suspected of having an infection caused by *P. gingivalis*. The detection of antigens or related peptides in immunoassays, includes any immunoassay known in the art including, but not limited to, radioimmunoassay, enzyme-linked immunosorbent assay (ELISA), "sandwich" assay, precipitin reaction, agglutination assay, fluorescent immunoassay, and chemiluminescence-based immunoassay.

EXAMPLE 5

Methods and Compounds for Vaccine Formulations Related to Synthetic Peptide Antigens and Multipeptide Constructs.

This embodiment of the present invention is to provide peptide antigens of Table 1 to be used as immunogens in a prophylactic and/or therapeutic vaccine for active immunization to protect against or treat infections caused by *P. gingivalis*. For vaccine purposes, an antigen of *P. gingivalis* comprising a synthetic peptide construct should be immunogenic, and induce functional antibodies directed to one or more surface-exposed epitopes on intact bacteria, wherein the epitope(s) are conserved amongst strains of *P. gingivalis*.

In one illustration of the invention, the dipeptide PAS1-PAS2 construct (FIG. 4) having the properties desirable of a vaccine antigen, the dipeptide construct can be synthesized using the method described herein in Example 3.

The synthetic peptide is included as the relevant immunogenic material in the vaccine formulation, and in therapeutically effective amounts, to induce an immune response. Many methods are known for the introduction of a vaccine formulation into the human or animal to be vaccinated. These include, but are not limited to, intradermal, intramuscular, intraperitoneal, intravenous, subcutaneous, ocular, intranasal, and oral administration. The vaccine may further comprise a physiological carrier such as a solution, a polymer or liposomes; and an adjuvant, or a combination thereof.

Various adjuvants are used in conjunction with vaccine formulations. The adjuvants aid by modulating the immune response and in attaining a more durable and higher level of immunity using smaller amounts of vaccine antigen or fewer doses than if the vaccine antigen were administered alone. Examples of adjuvants include incomplete Freund's adjuvant (ISA). Adjuvant 65 (containing peanut oil, mannide monooleate and aluminum monostrearate), oil emulsions, Ribi adjuvant, the pluronic polyols, polyamines, Avridine, Quil A, saponin. MPL, QS-21, and mineral gels such as aluminum hydroxide, aluminum phosphate, etc.

Another embodiment of this mode of the invention involves the production of antigen-specific amino acid sequences as a hapten, i.e. a molecule which cannot by itself elicit an immune response. In such case, the hapten may be covalently bound to a carrier or other immunogenic molecule which will confer immunogenicity to the coupled hapten when exposed to the immune system. Thus, such a antigen-specific hapten linked to a carrier molecule may be the immunogen in a vaccine formulation.

As an alternative to active immunization, immunization may be passive. i.e. immunization comprising administration of purified immunoglobulin containing antibody against synthetic peptides.

EXAMPLE 6

The following is an example of a proposed toothpaste formulation containing anti-peptide antibodies.

| Ingredient | % w/w |
|---|---|
| Dicalcium phosphate dihydrate | 50.0 |
| Glycerol | 20.0 |
| Sodium carboxymethyl cellulose | 1.0 |
| Sodium lauryl sulphate | 1.5 |
| Sodium lauroyl sarconisate | 0.5 |

-continued

| Ingredient | % w/w |
|---|---|
| Flavour | 1.0 |
| Sodium saccharin | 0.1 |
| Chlorhexidine gluconate | 0.01 |
| Dextranase | 0.01 |
| Goat serum containing anti-peptide Abs | 0.2 |
| Water | balance |

EXAMPLE 7

The following is an example of a proposed toothpaste formulation.

| Ingredient | % w/w |
|---|---|
| Dicalcium phosphate dihydrate | 50.0 |
| Sorbitol | 10.0 |
| Glycerol | 10.0 |
| Sodium carboxymethyl cellulose | 1.0 |
| Sodium lauryl sulphate | 1.5 |
| Flavour | 1.0 |
| Sodium saccharin | 0.1 |
| Sodium monofluorophosphate | 0.3 |
| Chlorhexidine gluconate | 0.01 |
| Dextranase | 0.01 |
| Bovine serum containing anti-peptide Abs | 0.2 |
| Water | balance |

EXAMPLE 8

The following is an example of a proposed toothpaste formulation.

| Ingredient | % w/w |
|---|---|
| Dicalcium phosphate dihydrate | 50.0 |
| Sorbitol | 10.0 |
| Glycerol | 10.0 |
| Sodium carboxymethyl cellulose | 1.0 |
| Lauroyl diethanolamide | 1.0 |
| Sucrose monolaurate | 2.0 |
| Flavour | 1.0 |
| Sodium saccharin | 0.1 |
| Sodium monofluorophosphate | 0.3 |
| Chlorhexidine gluconate | 0.01 |
| Dextranase | 0.01 |
| Bovine milk 1 g containing anti-peptide Abs | 0.1 |
| Water | balance |

EXAMPLE 9

The following is an example of a proposed toothpaste formulation.

| Ingredient | % w/w |
|---|---|
| Sorbitol | 22.0 |
| Irish moss | 1.0 |
| Sodium Hydroxide (50%) | 1.0 |
| Gantrez | 19.0 |
| Water (deionised) | 2.69 |

-continued

| Ingredient | % w/w |
|---|---|
| Sodium Monofluorophosphate | 0.76 |
| Sodium saccharine | 0.3 |
| Pyrophosphate | 2.0 |
| Hydrated alumina | 48.0 |
| Flavour oil | 0.95 |
| anti-peptide mouse monoclonal | 0.3 |
| sodium lauryl sulphate | 2.00 |

EXAMPLE 10

The following is an example of a proposed liquid toothpaste formulation.

| Ingredient | % w/w |
|---|---|
| Sodium polyacrylate | 50.0 |
| Sorbitol | 10.0 |
| Glycerol | 20.0 |
| Flavour | 1.0 |
| Sodium saccharin | 0.1 |
| Sodium monofluorophosphate | 0.3 |
| Chlorhexidine gluconate | 0.01 |
| Ethanol | 3.0 |
| Equine Ig containing anti-peptide Ab | 0.2 |
| Linolic acid | 0.05 |
| Water | balance |

EXAMPLE 11

The following is an example of a proposed mouthwash formulation.

| Ingredient | % w/w |
|---|---|
| Ethanol | 20.0 |
| Flavour | 1.0 |
| Sodium saccharin | 0.1 |
| Sodium monofluorophosphate | 0.3 |
| Chlorhexidine gluconate | 0.01 |
| Lauroyl diethanolamide | 0.3 |
| Rabbit Ig containing anti-peptide-Ab | 0.2 |
| Water | balance |

EXAMPLE 12

The following is an example of a proposed mouthwash formulation.

| Ingredient | % w/w |
|---|---|
| Gantrez S-97 | 2.5 |
| Glycerine | 10.0 |
| Flavour oil | 0.4 |
| Sodium monofluorophosphate | 0.05 |
| Chlorhexidine gluconate | 0.01 |
| Lauroyl diethanolamide | 0.2 |
| Mouse anti-peptide monoclonal | 0.3 |
| Water | balance |

EXAMPLE 13

The following is an example of a proposed lozenge formulation.

| Ingredient | % w/w |
|---|---|
| Sugar | 75–80 |
| Corn syrup | 1–20 |
| Flavour oil | 1–2 |
| NaF | 0.01–0.05 |
| Mouse anti-peptide monoclonal | 0.3 |
| Mg stearate | 1–5 |
| Water | balance |

EXAMPLE 14

The following is an example of a proposed gingival massage cream

| Ingredient | % w/w |
|---|---|
| White petrolatum | 8.0 |
| Propylene glycol | 4.0 |
| Stearyl alcohol | 8.0 |
| Polyethylene Glycol 4000 | 25.0 |
| Polyethylene Glycol 400 | 37.0 |
| Sucrose monostearate | 0.5 |
| Chlorohexidine gluconate | 0.1 |
| Mouse anti-peptide monoclonal | 0.3 |
| Water | balance |

EXAMPLE 15

The following is an example of a proposed chewing gum formulation.

| Ingredient | % w/w |
|---|---|
| Gum base | 30.0 |
| Calcium carbonate | 2.0 |
| Crystalline sorbitol | 53.0 |
| Glycerine | 0.5 |
| Flavour oil | 0.1 |
| Mouse anti-peptide monoclonals | 0.3 |
| Water | balance |

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

Alexander, J., Sidney, J., Southwood, S., et al (1994). "Development of high potentcy universal DR-restricted helper epitopes by modification of high affinity DR-blocking peptides." *Immunity* 1: 751-761.

Bhogal, P. S., Slakeski, N. & Reynolds, E. C. (1997). Characterization of a cell-associated, protein complex of *Porphyromonas gingivalis* W50 containing Arg- and Lys-specific cysteine proteinases and adhesins. *Microbiology* 143, 2485-2495.

Canne, L. E., Ferre-D'Amare, A. R., Burley, S. K., and Kent, S. B. H. (1995). "Total chemical synthesis of a unique transcription factor-related protein: cMyc-Max." *J. A. Chem. Soc.* 117: 2998-3001.

Druland, et. al. (1986). *J. Chem. Soc. Perkin Trans.* 1: 125-137.

Duncan, R., and Kopececk, J. (1980). "Degradation of side chains of N-(2-hydroxypropyl)methacrylamide copolymers by lysosomal enzymes." *Biochem. Biophys. Res. Commun.* 94: 284-290.

Geysen, H. M., Meleon, R. H., and Barteling, S. J. (1984). "Use of peptide synthesis to probe viral antigens for epitopes to a resolution of a single amino acid." *Proc. Natl. Acad. Sci. USA.* 81: 3998.

Geysen, H. M., Rodda, S. J., Mason, T. J., et al. (1987). "Strategies for epitope mapping using peptide synthesis." *J. Immunol. Methods.* 102: 259.

Hammer, J., Valsasnini, P., Tolba, K., Bolin, D., Higelin, J., Takacs, B., and Sinigaglia, F. (1993). "Promiscuous and allele-specific anchors in HLA-DR-binding peptides." *Cell* 74: 197-203.

Kaumaya. P. T. P., Kobs-Conrad. S., and DiGeorge, A. M. (1994). Synthetic peptide vaccines: Misconceptions and problems, strategies and prospects *Innovation and Perspectives in Solid Phase Synthesis*. R. Epton. Kingswinford, Mayflower: 279-292.

Liu, C. F. a. T., J. P. (1994). "Peptide ligation strategy without use of protectecing groups." *Proc. Natl. Acad. Sci. USA* 91: 6584-6588.

Lu, Y. A., Clavijo, P., Galantino, M., Shen, Z. Y., and Tam, J. P. (1991). "Chemically unambiguous peptide immunogen: Preparation, orientation and antigenicity of purified peptide cinjugated to the multiple antigen peptide system." *Mol. Immunol.* 28(6): 623-630.

Mitchell., e. a. (1978). *J. Org. Chem.* 43: 2845-2852.

Nakayama, K. (1997). Domain-specific rearrangement between the two Arg-gingipain-encoding genes in *Porphyromonas gingivalis*: possible involvement of nonreciprocal recombination. *Microbiol Immunol* 48, 185-196.

O'Brien-Simpson. N. M., Ede, N. J., Brown, L. E., Swan, J., and Jackson, D. C. (1997). "Polymerisation of unprotected synthetic peptides: a view towards a synthetic peptide vaccines." *J. Am. Chem. Soc.* 117(6).

O'Sullivan, D., Arrhenius, T., Sidney, J., et al (1991). "On the interaction of promiscuous antigenic peptides with different DR alleles. Indentification of common structural motifs." *J. Immunol* 147(8): 2663-2669.

Rose, K. (1994). "Facile synthesis of homogeneous artificial proteins." *J. Am. Chem. Soc.* 116: 30-33.

Rose, J., Zeng, W., Regamey, P. O., Chernusheivich, I. V., Standing, K. G., and Gaertner, H. F. (1996). "Natural peptides as building blocks for the synthesis of large protein-like molecules with hydrazone and oxime linkages." *Bioconjugate Chem.* 7(5): 552-556.

Shao, J., and Tam, J. P. (1995). *J. Am. Chem. Soc.* 117: 3893-3899.

Slakeski. N., Cleal, S. M. & Reynolds, E. C. (1996). Characterization of a *Porphyromonas gingivalis* gene prtR that encodes an arginine-specific thiol proteinase and multiple adhesins. *Biochem Biophys Res Comm* 224, 605-610.

Spetzler, J. C. a. T., J. P. (1994). A general approach for the synthesis of branched peptides for synthetic vaccines: Synthesis of multiple antigen peptides using unprotected segments. *Innovation and Perspectives in Solid Phase Synthesis*. R. Epton. Kingswinford, Mayflower: 293-300.

van Noort, J. M., and van der Drift, A. C. M. (1989). "The selectivity of cathepsin D suggeste an involvement of the enzyme in the generation of T-cell epitopes." *J. Biol. Chem.* 264(24): 14159-14164.

The invention claimed:

1. An isolated and purified peptide consisting of the sequence FNGGISLANYTGHGSETAWGT (SEQ ID NO:1).

2. A method of detecting the presence of *P. gingivalis*-specific antisera, comprising contacting a body fluid from an individual with the peptide of claim 1 and detecting antibodies present in said body fluid that bind to said peptide.

3. The method of claim 2, wherein the detection method is selected from the group consisting of: radioimmunoassay, enzyme-linked immunosorbent assay (ELISA), sandwich assay, precipitin reaction, agglutination assay, fluorescent immunoassay, and chemiluminescence-based immunoassay.

4. A composition for use in raising an immune response against *Porphyromonas gingivalis*, comprising the isolated and purified peptide of claim 1, wherein the peptide of claim 1, consist of the sequence depicted in SEQ ID NO:1, and a suitable adjuvant and/or acceptable carrier or excipient.

5. A method of inducing an immune response in a subject against *PorphyromoAas gingivalis*, comprising administering to said subject an amount of a composition according to claim 4 sufficient to induce an immune response to the peptide consisting of the sequence depicted in SEQ ID NO:1.

6. A method according to claim 5, wherein said composition is administered nasally, orally, or by injection.

7. A composition comprising the isolated and purified peptide of claim 1, wherein the peptide of claim 1 consists of the sequence depicted in SEQ ID NO:1, and at least one additional *Porphyromonas gingivalis* peptide.

8. An isolated and purified peptide consisting of the sequence LNTGVSFANYTAHGSETAWADP (SEQ ID NO:2).

9. A composition for use in raising an immune response against *Porphyromonas gingivalis*, comprising the isolated and purified peptide of claim 8, wherein the peptide of claim 8, consists of the sequence depicted in SEQ ID NO:2 and a suitable adjuvant and/or acceptable carrier or excipient.

10. A method of inducing an immune response in a subject against *Porphyromonas gingivalis*, comprising administering to said subject an amount of a composition according to claim 9 sufficient to induce an immune response to the peptide consisting of the sequence depicted in SEQ ID NO:2.

11. A method according to claim 10, wherein said composition is administered nasally, orally, or by injection.

12. A composition comprising the isolated and purified peptide of claim 8, wherein the peptide of claim 8 consists of the sequence depicted in SEQ ID NO:2, and at least one additional *Porphyromonas gingivalis* peptide.

13. A method of detecting the presence of *P. gingivalis*-specific antisera, comprising contacting a body fluid from an individual with the peptide of claim 8 and detecting antibodies present in said body fluid that bind to said peptide.

14. The method of claim 13, wherein the detection method is selected from the group consisting of:

radioimmunoassay, enzyme-linked immunosorbent assay (ELISA), sandwich assay, precipitin reaction, agglutination assay, fluorescent immunoassay, and chemiluminescence-based immunoassay.

* * * * *